United States Patent
Clardy et al.

(10) Patent No.: US 6,532,437 B1
(45) Date of Patent: *Mar. 11, 2003

(54) CRYSTALLINE FRAP COMPLEX

(75) Inventors: Jon C. Clardy, Ithaca, NY (US); Jungwon Choi, Seoul (KR)

(73) Assignee: Cornell Research Foundation, Inc., Ithaca, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/735,848

(22) Filed: Oct. 23, 1996

(51) Int. Cl.$^7$ ............................................... G06F 15/46
(52) U.S. Cl. ........................................ 703/11; 364/496
(58) Field of Search ...................... 364/496, 497–499, 364/578; 702/19, 27; 703/11, 12

(56) References Cited

U.S. PATENT DOCUMENTS

| | | | |
|---|---|---|---|
| 4,881,175 A | * 11/1989 | Ladner | 702/138 |
| 5,265,030 A | * 11/1993 | Skolnick et al. | 703/11 |
| 5,353,236 A | * 10/1994 | Subbiah | 364/496 X |
| 5,555,366 A | * 9/1996 | Teig et al. | 364/496 X |
| 5,557,535 A | * 9/1996 | Srinivasan et al. | 364/496 |
| 5,978,740 A | * 11/1999 | Armistead et al. | 702/19 |

FOREIGN PATENT DOCUMENTS

| | | |
|---|---|---|
| EP | A0676471 | 10/1995 |
| WO | WO94/25860 | 11/1994 |

OTHER PUBLICATIONS

Zheng et al., "TOR Kinase Domains are Required for Two Distinct Functions, Only One of which is Inhibited by Rapamycin" Cell, v. 82, p. 121–130, Jul. 14, 1995.*

Chen, "Identification of an 11kDa FKBP12–Rapamycin Binding Domain within the 289kDa FKBP12–Rapamycin Associated Protein and Characterization of a Critical Serine Residue" Proc. Natl. Acad. Sci. v. 92 pp. 4947–4951, May 1995.*

Wilson et al., "An Atomic Structure of FKBP12–Rapamycin" entry in http://www.pdb.bnl.gov/, Aug. 18, 1995.*

Chen, J. et al., "Identification of an 11–kDa FKBP12–rapamycin–binding domain within the 289–kDa FKBP12–rapamycin–associated protein and characterization of a critical serine residue", Proceedings of the National Academy of Science, 92:4947–4951, May 1995.

Brown, E.J. et al., "A mammalian protein targeted by G1–arresting rapamycin–receptor complex", Nature, 369:756–758, Jun. 30, 1994.

Van Duyne, G.D. et al., "Atomic Structures of the Human Immunophilin FKBP–12 Complexes with FK506 and Rapamycin", Journal of Molecular Biology, 229(1):105–124, 1993.

Griffith, J.P. et al., X–Ray Structure of Calcineurin Inhibited by the Immunophilin–Immunosuppressant FKBP12–FK506 Complex, Cell, 82:507–522, Aug. 11, 1995.

Choi, J. et al., "Structure of the FKBP12–Rapamycin Complex Interacting with the Binding Domain of Human FRAP", Science, 273:239–242, Jul. 12, 1996.

* cited by examiner

*Primary Examiner*—Kyle J. Choi
(74) *Attorney, Agent, or Firm*—Ropes & Gray

(57) ABSTRACT

The invention relates to the human protein FRAP, and in particular to the FKBP12-rapamycin binding domain thereof and to the ternary complex formed by the FRB domain, rapamycin and FKBP12. A new crystalline composition comprising the ternary complex, coordinates defining its three dimensional structure in atomic detail, and uses thereof are disclosed.

18 Claims, 47 Drawing Sheets

Figure 4: A-1

| | | | | | | | | | | |
|---|---|---|---|---|---|---|---|---|---|---|
| ATOM | 1 | C | GLY | 1 | 4.588 | 25.968 | 49.843 | 1.00 | 12.34 | FKBP |
| ATOM | 2 | O | GLY | 1 | 3.587 | 26.690 | 49.931 | 1.00 | 3.24 | FKBP |
| ATOM | 3 | HT1 | GLY | 1 | 5.460 | 28.281 | 50.881 | 0.00 | 0.00 | FKBP |
| ATOM | 4 | HT2 | GLY | 1 | 5.463 | 28.482 | 49.221 | 0.00 | 0.00 | FKBP |
| ATOM | 5 | N | GLY | 1 | 5.987 | 28.058 | 50.014 | 1.00 | 24.95 | FKBP |
| ATOM | 6 | HT3 | GLY | 1 | 6.961 | 28.429 | 50.048 | 0.00 | 0.00 | FKBP |
| ATOM | 7 | CA | GLY | 1 | 5.986 | 26.568 | 49.849 | 1.00 | 14.30 | FKBP |
| ATOM | 8 | N | VAL | 2 | 4.539 | 24.648 | 49.684 | 1.00 | 9.85 | FKBP |
| ATOM | 9 | H | VAL | 2 | 5.366 | 24.143 | 49.539 | 0.00 | 0.00 | FKBP |
| ATOM | 10 | CA | VAL | 2 | 3.311 | 23.862 | 49.748 | 1.00 | 11.89 | FKBP |
| ATOM | 11 | CB | VAL | 2 | 2.889 | 23.360 | 48.318 | 1.00 | 9.17 | FKBP |
| ATOM | 12 | CG1 | VAL | 2 | 4.114 | 23.006 | 47.492 | 1.00 | 14.93 | FKBP |
| ATOM | 13 | CG2 | VAL | 2 | 1.975 | 22.155 | 48.411 | 1.00 | 2.00 | FKBP |
| ATOM | 14 | C | VAL | 2 | 3.549 | 22.668 | 50.692 | 1.00 | 15.67 | FKBP |
| ATOM | 15 | O | VAL | 2 | 4.576 | 21.989 | 50.605 | 1.00 | 16.61 | FKBP |
| ATOM | 16 | N | GLN | 3 | 2.643 | 22.482 | 51.646 | 1.00 | 17.91 | FKBP |
| ATOM | 17 | H | GLN | 3 | 1.852 | 23.045 | 51.649 | 0.00 | 0.00 | FKBP |
| ATOM | 18 | CA | GLN | 3 | 2.789 | 21.445 | 52.664 | 1.00 | 20.42 | FKBP |
| ATOM | 19 | CB | GLN | 3 | 2.600 | 22.065 | 54.056 | 1.00 | 26.51 | FKBP |
| ATOM | 20 | CG | GLN | 3 | 2.416 | 21.064 | 55.181 | 1.00 | 34.77 | FKBP |
| ATOM | 21 | CD | GLN | 3 | 3.718 | 20.451 | 55.660 | 1.00 | 41.28 | FKBP |
| ATOM | 22 | OE1 | GLN | 3 | 4.754 | 20.581 | 55.015 | 1.00 | 44.41 | FKBP |
| ATOM | 23 | NE2 | GLN | 3 | 3.665 | 19.760 | 56.792 | 1.00 | 42.31 | FKBP |
| ATOM | 24 | HE21 | GLN | 3 | 2.812 | 19.651 | 57.241 | 0.00 | 0.00 | FKBP |
| ATOM | 25 | HE22 | GLN | 3 | 4.510 | 19.373 | 57.085 | 0.00 | 0.00 | FKBP |
| ATOM | 26 | C | GLN | 3 | 1.817 | 20.280 | 52.454 | 1.00 | 17.06 | FKBP |
| ATOM | 27 | O | GLN | 3 | 0.608 | 20.466 | 52.367 | 1.00 | 17.79 | FKBP |
| ATOM | 28 | N | VAL | 4 | 2.363 | 19.082 | 52.313 | 1.00 | 14.50 | FKBP |
| ATOM | 29 | H | VAL | 4 | 3.336 | 19.008 | 52.381 | 0.00 | 0.00 | FKBP |
| ATOM | 30 | CA | VAL | 4 | 1.540 | 17.890 | 52.127 | 1.00 | 13.12 | FKBP |
| ATOM | 31 | CB | VAL | 4 | 2.054 | 17.030 | 50.930 | 1.00 | 10.68 | FKBP |
| ATOM | 32 | CG1 | VAL | 4 | 0.924 | 16.172 | 50.364 | 1.00 | 7.51 | FKBP |
| ATOM | 33 | CG2 | VAL | 4 | 2.630 | 17.930 | 49.842 | 1.00 | 9.85 | FKBP |
| ATOM | 34 | C | VAL | 4 | 1.544 | 17.037 | 53.401 | 1.00 | 12.15 | FKBP |
| ATOM | 35 | O | VAL | 4 | 2.600 | 16.705 | 53.947 | 1.00 | 15.65 | FKBP |
| ATOM | 36 | N | GLU | 5 | 0.363 | 16.733 | 53.914 | 1.00 | 6.97 | FKBP |
| ATOM | 37 | H | GLU | 5 | -0.430 | 17.182 | 53.551 | 0.00 | 0.00 | FKBP |
| ATOM | 38 | CA | GLU | 5 | 0.275 | 15.856 | 55.071 | 1.00 | 5.19 | FKBP |
| ATOM | 39 | CB | GLU | 5 | -0.096 | 16.664 | 56.308 | 1.00 | 8.81 | FKBP |
| ATOM | 40 | CG | GLU | 5 | 0.621 | 17.998 | 56.389 | 1.00 | 13.30 | FKBP |
| ATOM | 41 | CD | GLU | 5 | 0.346 | 18.726 | 57.674 | 1.00 | 15.76 | FKBP |
| ATOM | 42 | OE1 | GLU | 5 | 1.188 | 18.629 | 58.586 | 1.00 | 22.97 | FKBP |
| ATOM | 43 | OE2 | GLU | 5 | -0.710 | 19.385 | 57.778 | 1.00 | 22.20 | FKBP |
| ATOM | 44 | C | GLU | 5 | -0.743 | 14.752 | 54.848 | 1.00 | 3.46 | FKBP |
| ATOM | 45 | O | GLU | 5 | -1.937 | 15.023 | 54.745 | 1.00 | 4.04 | FKBP |
| ATOM | 46 | N | THR | 6 | -0.271 | 13.511 | 54.805 | 1.00 | 2.00 | FKBP |
| ATOM | 47 | H | THR | 6 | 0.666 | 13.372 | 55.050 | 0.00 | 0.00 | FKBP |
| ATOM | 48 | CA | THR | 6 | -1.125 | 12.365 | 54.508 | 1.00 | 5.26 | FKBP |
| ATOM | 49 | CB | THR | 6 | -0.337 | 11.045 | 54.575 | 1.00 | 3.67 | FKBP |
| ATOM | 50 | OG1 | THR | 6 | 0.881 | 11.178 | 53.836 | 1.00 | 13.50 | FKBP |

Figure 4: A-2

| ATOM | 51 | HG1 | THR | 6 | 1.493 | 10.508 | 54.158 | 0.00 | 0.00 | FKBP |
|---|---|---|---|---|---|---|---|---|---|---|
| ATOM | 52 | CG2 | THR | 6 | -1.132 | 9.919 | 53.972 | 1.00 | 2.01 | FKBP |
| ATOM | 53 | C | THR | 6 | -2.355 | 12.240 | 55.415 | 1.00 | 9.57 | FKBP |
| ATOM | 54 | O | THR | 6 | -2.281 | 12.454 | 56.629 | 1.00 | 15.36 | FKBP |
| ATOM | 55 | N | ILE | 7 | -3.509 | 12.099 | 54.772 | 1.00 | 8.03 | FKBP |
| ATOM | 56 | H | ILE | 7 | -3.506 | 12.334 | 53.824 | 0.00 | 0.00 | FKBP |
| ATOM | 57 | CA | ILE | 7 | -4.755 | 11.709 | 55.423 | 1.00 | 7.62 | FKBP |
| ATOM | 58 | CB | ILE | 7 | -5.965 | 12.465 | 54.799 | 1.00 | 5.96 | FKBP |
| ATOM | 59 | CG2 | ILE | 7 | -7.275 | 11.841 | 55.244 | 1.00 | 2.71 | FKBP |
| ATOM | 60 | CG1 | ILE | 7 | -5.918 | 13.947 | 55.170 | 1.00 | 2.00 | FKBP |
| ATOM | 61 | CD1 | ILE | 7 | -7.008 | 14.764 | 54.527 | 1.00 | 2.01 | FKBP |
| ATOM | 62 | C | ILE | 7 | -4.979 | 10.199 | 55.249 | 1.00 | 11.96 | FKBP |
| ATOM | 63 | O | ILE | 7 | -5.686 | 9.576 | 56.034 | 1.00 | 17.57 | FKBP |
| ATOM | 64 | N | SER | 8 | -4.469 | 9.648 | 54.151 | 1.00 | 12.78 | FKBP |
| ATOM | 65 | H | SER | 8 | -4.039 | 10.240 | 53.499 | 0.00 | 0.00 | FKBP |
| ATOM | 66 | CA | SER | 8 | -4.629 | 8.226 | 53.842 | 1.00 | 12.24 | FKBP |
| ATOM | 67 | CB | SER | 8 | -6.079 | 7.930 | 53.450 | 1.00 | 6.63 | FKBP |
| ATOM | 68 | OG | SER | 8 | -6.236 | 6.581 | 53.064 | 1.00 | 12.33 | FKBP |
| ATOM | 69 | HG | SER | 8 | -7.179 | 6.384 | 53.022 | 0.00 | 0.00 | FKBP |
| ATOM | 70 | C | SER | 8 | -3.685 | 7.798 | 52.707 | 1.00 | 19.11 | FKBP |
| ATOM | 71 | O | SER | 8 | -3.607 | 8.454 | 51.664 | 1.00 | 17.14 | FKBP |
| ATOM | 72 | N | PRO | 9 | -2.830 | 6.798 | 52.965 | 1.00 | 23.27 | FKBP |
| ATOM | 73 | CD | PRO | 9 | -2.665 | 6.076 | 54.238 | 1.00 | 22.82 | FKBP |
| ATOM | 74 | CA | PRO | 9 | -1.706 | 6.548 | 52.055 | 1.00 | 25.68 | FKBP |
| ATOM | 75 | CB | PRO | 9 | -0.709 | 5.793 | 52.932 | 1.00 | 25.08 | FKBP |
| ATOM | 76 | CG | PRO | 9 | -1.572 | 5.093 | 53.920 | 1.00 | 26.18 | FKBP |
| ATOM | 77 | C | PRO | 9 | -2.056 | 5.766 | 50.778 | 1.00 | 28.63 | FKBP |
| ATOM | 78 | O | PRO | 9 | -3.034 | 5.014 | 50.737 | 1.00 | 30.17 | FKBP |
| ATOM | 79 | N | GLY | 10 | -1.272 | 5.988 | 49.728 | 1.00 | 28.78 | FKBP |
| ATOM | 80 | H | GLY | 10 | -0.602 | 6.696 | 49.796 | 0.00 | 0.00 | FKBP |
| ATOM | 81 | CA | GLY | 10 | -1.373 | 5.168 | 48.531 | 1.00 | 32.81 | FKBP |
| ATOM | 82 | C | GLY | 10 | -0.241 | 4.154 | 48.412 | 1.00 | 34.72 | FKBP |
| ATOM | 83 | O | GLY | 10 | 0.479 | 3.916 | 49.386 | 1.00 | 37.49 | FKBP |
| ATOM | 84 | N | ASP | 11 | -0.018 | 3.626 | 47.208 | 1.00 | 30.71 | FKBP |
| ATOM | 85 | H | ASP | 11 | -0.664 | 3.846 | 46.504 | 0.00 | 0.00 | FKBP |
| ATOM | 86 | CA | ASP | 11 | 0.992 | 2.585 | 47.006 | 1.00 | 28.23 | FKBP |
| ATOM | 87 | CB | ASP | 11 | 0.767 | 1.862 | 45.675 | 1.00 | 23.26 | FKBP |
| ATOM | 88 | CG | ASP | 11 | 0.713 | 2.804 | 44.493 | 1.00 | 21.83 | FKBP |
| ATOM | 89 | OD1 | ASP | 11 | 1.591 | 3.686 | 44.377 | 1.00 | 13.66 | FKBP |
| ATOM | 90 | OD2 | ASP | 11 | -0.204 | 2.635 | 43.659 | 1.00 | 23.38 | FKBP |
| ATOM | 91 | C | ASP | 11 | 2.438 | 3.073 | 47.085 | 1.00 | 29.86 | FKBP |
| ATOM | 92 | O | ASP | 11 | 3.364 | 2.273 | 47.190 | 1.00 | 31.65 | FKBP |
| ATOM | 93 | N | GLY | 12 | 2.637 | 4.372 | 46.898 | 1.00 | 31.53 | FKBP |
| ATOM | 94 | H | GLY | 12 | 1.858 | 4.932 | 46.696 | 0.00 | 0.00 | FKBP |
| ATOM | 95 | CA | GLY | 12 | 3.958 | 4.948 | 47.081 | 1.00 | 34.79 | FKBP |
| ATOM | 96 | C | GLY | 12 | 4.976 | 4.585 | 46.015 | 1.00 | 37.89 | FKBP |
| ATOM | 97 | O | GLY | 12 | 6.183 | 4.621 | 46.262 | 1.00 | 38.20 | FKBP |
| ATOM | 98 | N | ARG | 13 | 4.488 | 4.222 | 44.833 | 1.00 | 40.35 | FKBP |
| ATOM | 99 | H | ARG | 13 | 3.572 | 3.918 | 44.840 | 0.00 | 0.00 | FKBP |
| ATOM | 100 | CA | ARG | 13 | 5.357 | 4.030 | 43.667 | 1.00 | 43.98 | FKBP |

Figure 4: A-3

| ATOM | 101 | CB   | ARG | 13 | 5.756 | 2.552  | 43.526 | 1.00 | 48.12 | FKBP |
|------|-----|------|-----|----|-------|--------|--------|------|-------|------|
| ATOM | 102 | CG   | ARG | 13 | 4.624 | 1.555  | 43.724 | 1.00 | 56.08 | FKBP |
| ATOM | 103 | CD   | ARG | 13 | 5.130 | 0.296  | 44.418 | 1.00 | 64.50 | FKBP |
| ATOM | 104 | NE   | ARG | 13 | 4.963 | 0.361  | 45.870 | 1.00 | 70.55 | FKBP |
| ATOM | 105 | HE   | ARG | 13 | 5.508 | 1.005  | 46.370 | 0.00 | 0.00  | FKBP |
| ATOM | 106 | CZ   | ARG | 13 | 4.154 | -0.435 | 46.567 | 1.00 | 73.54 | FKBP |
| ATOM | 107 | NH1  | ARG | 13 | 4.023 | -0.266 | 47.877 | 1.00 | 74.82 | FKBP |
| ATOM | 108 | HH11 | ARG | 13 | 4.540 | 0.450  | 48.341 | 0.00 | 0.00  | FKBP |
| ATOM | 109 | HH12 | ARG | 13 | 3.414 | -0.864 | 48.399 | 0.00 | 0.00  | FKBP |
| ATOM | 110 | NH2  | ARG | 13 | 3.490 | -1.415 | 45.961 | 1.00 | 75.14 | FKBP |
| ATOM | 111 | HH21 | ARG | 13 | 3.595 | -1.557 | 44.977 | 0.00 | 0.00  | FKBP |
| ATOM | 112 | HH22 | ARG | 13 | 2.873 | -2.001 | 46.485 | 0.00 | 0.00  | FKBP |
| ATOM | 113 | C    | ARG | 13 | 4.720 | 4.537  | 42.369 | 1.00 | 40.88 | FKBP |
| ATOM | 114 | O    | ARG | 13 | 5.414 | 4.995  | 41.459 | 1.00 | 41.05 | FKBP |
| ATOM | 115 | N    | THR | 14 | 3.392 | 4.531  | 42.328 | 1.00 | 36.51 | FKBP |
| ATOM | 116 | H    | THR | 14 | 2.944 | 3.906  | 42.915 | 0.00 | 0.00  | FKBP |
| ATOM | 117 | CA   | THR | 14 | 2.654 | 5.085  | 41.199 | 1.00 | 31.82 | FKBP |
| ATOM | 118 | CB   | THR | 14 | 1.296 | 4.362  | 41.010 | 1.00 | 34.22 | FKBP |
| ATOM | 119 | OG1  | THR | 14 | 1.477 | 2.945  | 41.172 | 1.00 | 31.38 | FKBP |
| ATOM | 120 | HG1  | THR | 14 | 0.659 | 2.484  | 40.952 | 0.00 | 0.00  | FKBP |
| ATOM | 121 | CG2  | THR | 14 | 0.722 | 4.651  | 39.621 | 1.00 | 29.70 | FKBP |
| ATOM | 122 | C    | THR | 14 | 2.416 | 6.589  | 41.356 | 1.00 | 28.19 | FKBP |
| ATOM | 123 | O    | THR | 14 | 1.373 | 7.023  | 41.846 | 1.00 | 25.30 | FKBP |
| ATOM | 124 | N    | PHE | 15 | 3.430 | 7.364  | 41.000 | 1.00 | 27.12 | FKBP |
| ATOM | 125 | H    | PHE | 15 | 4.257 | 6.922  | 40.707 | 0.00 | 0.00  | FKBP |
| ATOM | 126 | CA   | PHE | 15 | 3.354 | 8.822  | 40.970 | 1.00 | 30.73 | FKBP |
| ATOM | 127 | CB   | PHE | 15 | 4.725 | 9.405  | 41.330 | 1.00 | 30.56 | FKBP |
| ATOM | 128 | CG   | PHE | 15 | 5.202 | 9.018  | 42.701 | 1.00 | 31.81 | FKBP |
| ATOM | 129 | CD1  | PHE | 15 | 5.046 | 9.885  | 43.775 | 1.00 | 31.26 | FKBP |
| ATOM | 130 | CD2  | PHE | 15 | 5.732 | 7.756  | 42.936 | 1.00 | 31.84 | FKBP |
| ATOM | 131 | CE1  | PHE | 15 | 5.400 | 9.499  | 45.062 | 1.00 | 28.40 | FKBP |
| ATOM | 132 | CE2  | PHE | 15 | 6.089 | 7.363  | 44.218 | 1.00 | 31.05 | FKBP |
| ATOM | 133 | CZ   | PHE | 15 | 5.919 | 8.237  | 45.283 | 1.00 | 31.16 | FKBP |
| ATOM | 134 | C    | PHE | 15 | 2.902 | 9.358  | 39.596 | 1.00 | 34.59 | FKBP |
| ATOM | 135 | O    | PHE | 15 | 3.176 | 8.739  | 38.557 | 1.00 | 32.29 | FKBP |
| ATOM | 136 | N    | PRO | 16 | 2.232 | 10.532 | 39.571 | 1.00 | 35.21 | FKBP |
| ATOM | 137 | CD   | PRO | 16 | 2.068 | 11.493 | 40.671 | 1.00 | 32.43 | FKBP |
| ATOM | 138 | CA   | PRO | 16 | 1.814 | 11.122 | 38.296 | 1.00 | 36.14 | FKBP |
| ATOM | 139 | CB   | PRO | 16 | 0.852 | 12.243 | 38.710 | 1.00 | 33.90 | FKBP |
| ATOM | 140 | CG   | PRO | 16 | 0.905 | 12.310 | 40.215 | 1.00 | 34.16 | FKBP |
| ATOM | 141 | C    | PRO | 16 | 2.998 | 11.672 | 37.512 | 1.00 | 38.59 | FKBP |
| ATOM | 142 | O    | PRO | 16 | 3.580 | 12.683 | 37.895 | 1.00 | 40.62 | FKBP |
| ATOM | 143 | N    | LYS | 17 | 3.408 | 10.958 | 36.467 | 1.00 | 44.97 | FKBP |
| ATOM | 144 | H    | LYS | 17 | 3.044 | 10.054 | 36.366 | 0.00 | 0.00  | FKBP |
| ATOM | 145 | CA   | LYS | 17 | 4.463 | 11.441 | 35.572 | 1.00 | 49.95 | FKBP |
| ATOM | 146 | CB   | LYS | 17 | 4.856 | 10.356 | 34.563 | 1.00 | 53.22 | FKBP |
| ATOM | 147 | CG   | LYS | 17 | 5.973 | 9.427  | 35.030 | 1.00 | 61.47 | FKBP |
| ATOM | 148 | CD   | LYS | 17 | 5.425 | 8.075  | 35.497 | 1.00 | 69.15 | FKBP |
| ATOM | 149 | CE   | LYS | 17 | 6.545 | 7.050  | 35.721 | 1.00 | 73.13 | FKBP |
| ATOM | 150 | NZ   | LYS | 17 | 6.050 | 5.706  | 36.174 | 1.00 | 72.77 | FKBP |

Figure 4: A-4

| | | | | | | | | | | |
|---|---|---|---|---|---|---|---|---|---|---|
| ATOM | 151 | HZ1  | LYS | 17 | 5.395 | 5.316 | 35.466 | 0.00 | 0.00 | FKBP |
| ATOM | 152 | HZ2  | LYS | 17 | 5.550 | 5.803 | 37.081 | 0.00 | 0.00 | FKBP |
| ATOM | 153 | HZ3  | LYS | 17 | 6.857 | 5.061 | 36.292 | 0.00 | 0.00 | FKBP |
| ATOM | 154 | C    | LYS | 17 | 4.031 | 12.703 | 34.823 | 1.00 | 50.23 | FKBP |
| ATOM | 155 | O    | LYS | 17 | 2.882 | 12.813 | 34.389 | 1.00 | 51.36 | FKBP |
| ATOM | 156 | N    | ARG | 18 | 4.938 | 13.672 | 34.718 | 1.00 | 48.43 | FKBP |
| ATOM | 157 | H    | ARG | 18 | 5.782 | 13.553 | 35.190 | 0.00 | 0.00 | FKBP |
| ATOM | 158 | CA   | ARG | 18 | 4.666 | 14.908 | 33.986 | 1.00 | 46.13 | FKBP |
| ATOM | 159 | CB   | ARG | 18 | 5.968 | 15.671 | 33.732 | 1.00 | 47.22 | FKBP |
| ATOM | 160 | CG   | ARG | 18 | 5.755 | 17.034 | 33.092 | 1.00 | 53.52 | FKBP |
| ATOM | 161 | CD   | ARG | 18 | 7.030 | 17.572 | 32.467 | 1.00 | 60.93 | FKBP |
| ATOM | 162 | NE   | ARG | 18 | 8.005 | 18.008 | 33.466 | 1.00 | 68.56 | FKBP |
| ATOM | 163 | HE   | ARG | 18 | 8.698 | 17.375 | 33.748 | 0.00 | 0.00 | FKBP |
| ATOM | 164 | CZ   | ARG | 18 | 7.995 | 19.201 | 34.054 | 1.00 | 71.82 | FKBP |
| ATOM | 165 | NH1  | ARG | 18 | 8.954 | 19.528 | 34.910 | 1.00 | 73.41 | FKBP |
| ATOM | 166 | HH11 | ARG | 18 | 9.674 | 18.876 | 35.143 | 0.00 | 0.00 | FKBP |
| ATOM | 167 | HH12 | ARG | 18 | 8.923 | 20.425 | 35.358 | 0.00 | 0.00 | FKBP |
| ATOM | 168 | NH2  | ARG | 18 | 7.000 | 20.052 | 33.826 | 1.00 | 74.07 | FKBP |
| ATOM | 169 | HH21 | ARG | 18 | 6.256 | 19.798 | 33.207 | 0.00 | 0.00 | FKBP |
| ATOM | 170 | HH22 | ARG | 18 | 6.994 | 20.950 | 34.267 | 0.00 | 0.00 | FKBP |
| ATOM | 171 | C    | ARG | 18 | 3.965 | 14.637 | 32.652 | 1.00 | 44.43 | FKBP |
| ATOM | 172 | O    | ARG | 18 | 4.440 | 13.832 | 31.844 | 1.00 | 44.85 | FKBP |
| ATOM | 173 | N    | GLY | 19 | 2.775 | 15.209 | 32.491 | 1.00 | 41.63 | FKBP |
| ATOM | 174 | H    | GLY | 19 | 2.437 | 15.781 | 33.210 | 0.00 | 0.00 | FKBP |
| ATOM | 175 | CA   | GLY | 19 | 2.037 | 15.058 | 31.246 | 1.00 | 36.64 | FKBP |
| ATOM | 176 | C    | GLY | 19 | 0.878 | 14.072 | 31.281 | 1.00 | 33.71 | FKBP |
| ATOM | 177 | O    | GLY | 19 | 0.242 | 13.821 | 30.256 | 1.00 | 31.30 | FKBP |
| ATOM | 178 | N    | GLN | 20 | 0.603 | 13.509 | 32.454 | 1.00 | 31.51 | FKBP |
| ATOM | 179 | H    | GLN | 20 | 1.278 | 13.579 | 33.162 | 0.00 | 0.00 | FKBP |
| ATOM | 180 | CA   | GLN | 20 | -0.571 | 12.655 | 32.647 | 1.00 | 27.89 | FKBP |
| ATOM | 181 | CB   | GLN | 20 | -0.290 | 11.586 | 33.702 | 1.00 | 27.47 | FKBP |
| ATOM | 182 | CG   | GLN | 20 | 0.907 | 10.723 | 33.416 | 1.00 | 29.05 | FKBP |
| ATOM | 183 | CD   | GLN | 20 | 0.945 | 9.516 | 34.305 | 1.00 | 28.73 | FKBP |
| ATOM | 184 | OE1  | GLN | 20 | 1.852 | 9.355 | 35.112 | 1.00 | 29.95 | FKBP |
| ATOM | 185 | NE2  | GLN | 20 | -0.064 | 8.672 | 34.191 | 1.00 | 29.76 | FKBP |
| ATOM | 186 | HE21 | GLN | 20 | -0.781 | 8.854 | 33.542 | 0.00 | 0.00 | FKBP |
| ATOM | 187 | HE22 | GLN | 20 | -0.025 | 7.895 | 34.776 | 0.00 | 0.00 | FKBP |
| ATOM | 188 | C    | GLN | 20 | -1.784 | 13.458 | 33.096 | 1.00 | 26.36 | FKBP |
| ATOM | 189 | O    | GLN | 20 | -1.641 | 14.558 | 33.652 | 1.00 | 23.69 | FKBP |
| ATOM | 190 | N    | THR | 21 | -2.957 | 12.836 | 32.994 | 1.00 | 23.74 | FKBP |
| ATOM | 191 | H    | THR | 21 | -2.993 | 11.964 | 32.525 | 0.00 | 0.00 | FKBP |
| ATOM | 192 | CA   | THR | 21 | -4.185 | 13.406 | 33.551 | 1.00 | 19.78 | FKBP |
| ATOM | 193 | CB   | THR | 21 | -5.398 | 13.137 | 32.648 | 1.00 | 18.09 | FKBP |
| ATOM | 194 | OG1  | THR | 21 | -5.103 | 13.576 | 31.319 | 1.00 | 25.65 | FKBP |
| ATOM | 195 | HG1  | THR | 21 | -4.667 | 12.831 | 30.862 | 0.00 | 0.00 | FKBP |
| ATOM | 196 | CG2  | THR | 21 | -6.624 | 13.882 | 33.159 | 1.00 | 15.30 | FKBP |
| ATOM | 197 | C    | THR | 21 | -4.502 | 12.869 | 34.945 | 1.00 | 19.51 | FKBP |
| ATOM | 198 | O    | THR | 21 | -4.895 | 11.707 | 35.112 | 1.00 | 21.36 | FKBP |
| ATOM | 199 | N    | CYS | 22 | -4.390 | 13.744 | 35.939 | 1.00 | 15.33 | FKBP |
| ATOM | 200 | H    | CYS | 22 | -4.044 | 14.636 | 35.726 | 0.00 | 0.00 | FKBP |

Figure 4: A-5

```
ATOM    201  CA   CYS  22    -4.794  13.421  37.302  1.00   7.92    FKBP
ATOM    202  CB   CYS  22    -4.056  14.322  38.281  1.00   4.88    FKBP
ATOM    203  SG   CYS  22    -2.300  14.464  37.959  1.00   9.58    FKBP
ATOM    204  C    CYS  22    -6.301  13.589  37.492  1.00   7.02    FKBP
ATOM    205  O    CYS  22    -6.840  14.676  37.284  1.00   8.66    FKBP
ATOM    206  N    VAL  23    -6.991  12.485  37.760  1.00   4.33    FKBP
ATOM    207  H    VAL  23    -6.547  11.617  37.634  0.00   0.00    FKBP
ATOM    208  CA   VAL  23    -8.371  12.542  38.232  1.00   6.31    FKBP
ATOM    209  CB   VAL  23    -9.180  11.314  37.743  1.00   3.87    FKBP
ATOM    210  CG1  VAL  23   -10.658  11.483  38.043  1.00   2.00    FKBP
ATOM    211  CG2  VAL  23    -8.972  11.121  36.264  1.00   5.84    FKBP
ATOM    212  C    VAL  23    -8.353  12.579  39.770  1.00  11.82    FKBP
ATOM    213  O    VAL  23    -7.678  11.765  40.416  1.00  17.38    FKBP
ATOM    214  N    VAL  24    -8.946  13.622  40.342  1.00  10.13    FKBP
ATOM    215  H    VAL  24    -9.395  14.274  39.762  0.00   0.00    FKBP
ATOM    216  CA   VAL  24    -8.896  13.840  41.782  1.00   5.89    FKBP
ATOM    217  CB   VAL  24    -7.806  14.883  42.170  1.00   3.59    FKBP
ATOM    218  CG1  VAL  24    -6.481  14.535  41.524  1.00   2.00    FKBP
ATOM    219  CG2  VAL  24    -8.238  16.276  41.784  1.00   2.66    FKBP
ATOM    220  C    VAL  24   -10.237  14.309  42.333  1.00   7.13    FKBP
ATOM    221  O    VAL  24   -11.078  14.804  41.583  1.00   8.15    FKBP
ATOM    222  N    HIS  25   -10.481  14.041  43.617  1.00   8.15    FKBP
ATOM    223  H    HIS  25    -9.837  13.454  44.074  0.00   0.00    FKBP
ATOM    224  CA   HIS  25   -11.588  14.671  44.346  1.00   5.84    FKBP
ATOM    225  CB   HIS  25   -12.462  13.611  45.015  1.00   2.00    FKBP
ATOM    226  CG   HIS  25   -13.789  13.412  44.351  1.00   2.00    FKBP
ATOM    227  CD2  HIS  25   -14.625  12.348  44.335  1.00   2.01    FKBP
ATOM    228  ND1  HIS  25   -14.420  14.398  43.625  1.00   6.75    FKBP
ATOM    229  HD1  HIS  25   -13.990  15.194  43.216  0.00   0.00    FKBP
ATOM    230  CE1  HIS  25   -15.591  13.959  43.204  1.00   2.00    FKBP
ATOM    231  NE2  HIS  25   -15.738  12.715  43.619  1.00   2.00    FKBP
ATOM    232  HE2  HIS  25   -16.532  12.146  43.449  0.00   0.00    FKBP
ATOM    233  C    HIS  25   -11.013  15.611  45.409  1.00   5.86    FKBP
ATOM    234  O    HIS  25   -10.085  15.233  46.125  1.00   8.08    FKBP
ATOM    235  N    TYR  26   -11.456  16.867  45.414  1.00   2.00    FKBP
ATOM    236  H    TYR  26   -12.071  17.155  44.712  0.00   0.00    FKBP
ATOM    237  CA   TYR  26   -10.956  17.840  46.389  1.00   2.00    FKBP
ATOM    238  CB   TYR  26    -9.950  18.827  45.770  1.00   3.39    FKBP
ATOM    239  CG   TYR  26   -10.570  19.839  44.824  1.00   8.68    FKBP
ATOM    240  CD1  TYR  26   -11.017  21.080  45.279  1.00   7.15    FKBP
ATOM    241  CE1  TYR  26   -11.725  21.939  44.434  1.00  11.31    FKBP
ATOM    242  CD2  TYR  26   -10.831  19.497  43.495  1.00  11.88    FKBP
ATOM    243  CE2  TYR  26   -11.536  20.342  42.651  1.00   8.71    FKBP
ATOM    244  CZ   TYR  26   -11.982  21.551  43.122  1.00   9.36    FKBP
ATOM    245  OH   TYR  26   -12.704  22.348  42.274  1.00   9.02    FKBP
ATOM    246  HH   TYR  26   -12.792  21.935  41.411  0.00   0.00    FKBP
ATOM    247  C    TYR  26   -12.057  18.638  47.045  1.00   2.60    FKBP
ATOM    248  O    TYR  26   -13.162  18.746  46.515  1.00   2.96    FKBP
ATOM    249  N    THR  27   -11.778  19.056  48.276  1.00   8.98    FKBP
ATOM    250  H    THR  27   -11.030  18.611  48.735  0.00   0.00    FKBP
```

Figure 4: A-6

| ATOM | 251 | CA  | THR | 27 | -12.469 | 20.164 | 48.924 | 1.00 | 3.70  | FKBP |
|------|-----|-----|-----|----|---------|--------|--------|------|-------|------|
| ATOM | 252 | CB  | THR | 27 | -13.138 | 19.737 | 50.219 | 1.00 | 3.82  | FKBP |
| ATOM | 253 | OG1 | THR | 27 | -13.987 | 18.606 | 49.972 | 1.00 | 5.37  | FKBP |
| ATOM | 254 | HG1 | THR | 27 | -13.409 | 17.851 | 49.785 | 0.00 | 0.00  | FKBP |
| ATOM | 255 | CG2 | THR | 27 | -13.957 | 20.891 | 50.779 | 1.00 | 2.73  | FKBP |
| ATOM | 256 | C   | THR | 27 | -11.436 | 21.213 | 49.273 | 1.00 | 2.00  | FKBP |
| ATOM | 257 | O   | THR | 27 | -10.365 | 20.891 | 49.784 | 1.00 | 2.00  | FKBP |
| ATOM | 258 | N   | GLY | 28 | -11.664 | 22.419 | 48.779 | 1.00 | 5.64  | FKBP |
| ATOM | 259 | H   | GLY | 28 | -12.274 | 22.498 | 48.038 | 0.00 | 0.00  | FKBP |
| ATOM | 260 | CA  | GLY | 28 | -10.813 | 23.538 | 49.128 | 1.00 | 8.04  | FKBP |
| ATOM | 261 | C   | GLY | 28 | -11.438 | 24.437 | 50.175 | 1.00 | 8.15  | FKBP |
| ATOM | 262 | O   | GLY | 28 | -12.646 | 24.729 | 50.131 | 1.00 | 9.73  | FKBP |
| ATOM | 263 | N   | MET | 29 | -10.619 | 24.887 | 51.117 | 1.00 | 4.38  | FKBP |
| ATOM | 264 | H   | MET | 29 | -9.683  | 24.601 | 51.122 | 0.00 | 0.00  | FKBP |
| ATOM | 265 | CA  | MET | 29 | -11.091 | 25.812 | 52.138 | 1.00 | 6.14  | FKBP |
| ATOM | 266 | CB  | MET | 29 | -11.512 | 25.047 | 53.404 | 1.00 | 11.72 | FKBP |
| ATOM | 267 | CG  | MET | 29 | -10.445 | 24.128 | 53.999 | 1.00 | 14.88 | FKBP |
| ATOM | 268 | SD  | MET | 29 | -11.065 | 22.500 | 54.510 | 1.00 | 7.90  | FKBP |
| ATOM | 269 | CE  | MET | 29 | -12.824 | 22.854 | 54.721 | 1.00 | 5.60  | FKBP |
| ATOM | 270 | C   | MET | 29 | -10.033 | 26.845 | 52.477 | 1.00 | 6.50  | FKBP |
| ATOM | 271 | O   | MET | 29 | -8.847  | 26.630 | 52.242 | 1.00 | 5.89  | FKBP |
| ATOM | 272 | N   | LEU | 30 | -10.477 | 28.013 | 52.923 | 1.00 | 11.28 | FKBP |
| ATOM | 273 | H   | LEU | 30 | -11.444 | 28.168 | 52.902 | 0.00 | 0.00  | FKBP |
| ATOM | 274 | CA  | LEU | 30 | -9.561  | 29.028 | 53.443 | 1.00 | 14.74 | FKBP |
| ATOM | 275 | CB  | LEU | 30 | -10.281 | 30.379 | 53.572 | 1.00 | 12.99 | FKBP |
| ATOM | 276 | CG  | LEU | 30 | -10.887 | 30.967 | 52.292 | 1.00 | 10.36 | FKBP |
| ATOM | 277 | CD1 | LEU | 30 | -12.064 | 31.842 | 52.668 | 1.00 | 12.99 | FKBP |
| ATOM | 278 | CD2 | LEU | 30 | -9.848  | 31.761 | 51.510 | 1.00 | 3.34  | FKBP |
| ATOM | 279 | C   | LEU | 30 | -9.042  | 28.573 | 54.805 | 1.00 | 14.12 | FKBP |
| ATOM | 280 | O   | LEU | 30 | -9.664  | 27.732 | 55.453 | 1.00 | 16.16 | FKBP |
| ATOM | 281 | N   | GLU | 31 | -7.944  | 29.169 | 55.262 | 1.00 | 14.66 | FKBP |
| ATOM | 282 | H   | GLU | 31 | -7.506  | 29.828 | 54.682 | 0.00 | 0.00  | FKBP |
| ATOM | 283 | CA  | GLU | 31 | -7.266  | 28.722 | 56.483 | 1.00 | 17.28 | FKBP |
| ATOM | 284 | CB  | GLU | 31 | -6.294  | 29.799 | 56.962 | 1.00 | 14.61 | FKBP |
| ATOM | 285 | CG  | GLU | 31 | -5.818  | 29.586 | 58.382 | 1.00 | 22.25 | FKBP |
| ATOM | 286 | CD  | GLU | 31 | -4.510  | 30.284 | 58.698 | 1.00 | 26.77 | FKBP |
| ATOM | 287 | OE1 | GLU | 31 | -4.245  | 31.362 | 58.107 | 1.00 | 21.74 | FKBP |
| ATOM | 288 | OE2 | GLU | 31 | -3.774  | 29.762 | 59.576 | 1.00 | 23.08 | FKBP |
| ATOM | 289 | C   | GLU | 31 | -8.187  | 28.313 | 57.642 | 1.00 | 18.96 | FKBP |
| ATOM | 290 | O   | GLU | 31 | -8.008  | 27.258 | 58.262 | 1.00 | 18.93 | FKBP |
| ATOM | 291 | N   | ASP | 32 | -9.238  | 29.090 | 57.855 | 1.00 | 17.34 | FKBP |
| ATOM | 292 | H   | ASP | 32 | -9.405  | 29.814 | 57.223 | 0.00 | 0.00  | FKBP |
| ATOM | 293 | CA  | ASP | 32 | -10.116 | 28.866 | 58.996 | 1.00 | 19.84 | FKBP |
| ATOM | 294 | CB  | ASP | 32 | -10.894 | 30.142 | 59.308 | 1.00 | 27.98 | FKBP |
| ATOM | 295 | CG  | ASP | 32 | -11.601 | 30.704 | 58.090 | 1.00 | 34.72 | FKBP |
| ATOM | 296 | OD1 | ASP | 32 | -12.727 | 30.254 | 57.801 | 1.00 | 32.49 | FKBP |
| ATOM | 297 | OD2 | ASP | 32 | -11.023 | 31.588 | 57.415 | 1.00 | 43.34 | FKBP |
| ATOM | 298 | C   | ASP | 32 | -11.096 | 27.713 | 58.816 | 1.00 | 18.08 | FKBP |
| ATOM | 299 | O   | ASP | 32 | -11.986 | 27.541 | 59.638 | 1.00 | 17.85 | FKBP |
| ATOM | 300 | N   | GLY | 33 | -10.994 | 26.998 | 57.697 | 1.00 | 18.90 | FKBP |

Figure 4: A-7

| ATOM | 301 | H   | GLY | 33 | -10.204 | 27.111 | 57.137 | 0.00 | 0.00  | FKBP |
|------|-----|-----|-----|----|---------|--------|--------|------|-------|------|
| ATOM | 302 | CA  | GLY | 33 | -11.909 | 25.896 | 57.417 | 1.00 | 14.65 | FKBP |
| ATOM | 303 | C   | GLY | 33 | -13.146 | 26.270 | 56.616 | 1.00 | 10.95 | FKBP |
| ATOM | 304 | O   | GLY | 33 | -14.020 | 25.437 | 56.370 | 1.00 | 11.28 | FKBP |
| ATOM | 305 | N   | LYS | 34 | -13.235 | 27.536 | 56.230 | 1.00 | 5.53  | FKBP |
| ATOM | 306 | H   | LYS | 34 | -12.565 | 28.159 | 56.564 | 0.00 | 0.00  | FKBP |
| ATOM | 307 | CA  | LYS | 34 | -14.320 | 27.999 | 55.379 | 1.00 | 7.65  | FKBP |
| ATOM | 308 | CB  | LYS | 34 | -14.270 | 29.521 | 55.255 | 1.00 | 15.91 | FKBP |
| ATOM | 309 | CG  | LYS | 34 | -15.468 | 30.131 | 54.554 | 1.00 | 23.47 | FKBP |
| ATOM | 310 | CD  | LYS | 34 | -15.360 | 31.646 | 54.513 | 1.00 | 34.71 | FKBP |
| ATOM | 311 | CE  | LYS | 34 | -15.213 | 32.245 | 55.918 | 1.00 | 38.38 | FKBP |
| ATOM | 312 | NZ  | LYS | 34 | -13.805 | 32.635 | 56.227 | 1.00 | 41.83 | FKBP |
| ATOM | 313 | HZ1 | LYS | 34 | -13.475 | 33.324 | 55.520 | 0.00 | 0.00  | FKBP |
| ATOM | 314 | HZ2 | LYS | 34 | -13.196 | 31.792 | 56.185 | 0.00 | 0.00  | FKBP |
| ATOM | 315 | HZ3 | LYS | 34 | -13.749 | 33.055 | 57.176 | 0.00 | 0.00  | FKBP |
| ATOM | 316 | C   | LYS | 34 | -14.222 | 27.369 | 53.991 | 1.00 | 7.56  | FKBP |
| ATOM | 317 | O   | LYS | 34 | -13.290 | 27.653 | 53.232 | 1.00 | 3.26  | FKBP |
| ATOM | 318 | N   | LYS | 35 | -15.067 | 26.371 | 53.757 | 1.00 | 8.73  | FKBP |
| ATOM | 319 | H   | LYS | 35 | -15.554 | 26.012 | 54.530 | 0.00 | 0.00  | FKBP |
| ATOM | 320 | CA  | LYS | 35 | -15.178 | 25.719 | 52.459 | 1.00 | 8.15  | FKBP |
| ATOM | 321 | CB  | LYS | 35 | -16.269 | 24.657 | 52.511 | 1.00 | 2.40  | FKBP |
| ATOM | 322 | CG  | LYS | 35 | -16.379 | 23.854 | 51.249 | 1.00 | 7.41  | FKBP |
| ATOM | 323 | CD  | LYS | 35 | -17.142 | 22.573 | 51.484 | 1.00 | 11.33 | FKBP |
| ATOM | 324 | CE  | LYS | 35 | -18.637 | 22.803 | 51.464 | 1.00 | 15.67 | FKBP |
| ATOM | 325 | NZ  | LYS | 35 | -19.352 | 21.501 | 51.304 | 1.00 | 20.77 | FKBP |
| ATOM | 326 | HZ1 | LYS | 35 | -19.180 | 20.892 | 52.129 | 0.00 | 0.00  | FKBP |
| ATOM | 327 | HZ2 | LYS | 35 | -19.004 | 21.025 | 50.450 | 0.00 | 0.00  | FKBP |
| ATOM | 328 | HZ3 | LYS | 35 | -20.373 | 21.681 | 51.212 | 0.00 | 0.00  | FKBP |
| ATOM | 329 | C   | LYS | 35 | -15.520 | 26.736 | 51.378 | 1.00 | 13.32 | FKBP |
| ATOM | 330 | O   | LYS | 35 | -16.387 | 27.596 | 51.587 | 1.00 | 16.59 | FKBP |
| ATOM | 331 | N   | PHE | 36 | -14.796 | 26.690 | 50.257 | 1.00 | 12.19 | FKBP |
| ATOM | 332 | H   | PHE | 36 | -13.981 | 26.149 | 50.278 | 0.00 | 0.00  | FKBP |
| ATOM | 333 | CA  | PHE | 36 | -15.167 | 27.504 | 49.098 | 1.00 | 8.93  | FKBP |
| ATOM | 334 | CB  | PHE | 36 | -14.077 | 28.541 | 48.753 | 1.00 | 4.86  | FKBP |
| ATOM | 335 | CG  | PHE | 36 | -12.728 | 27.959 | 48.415 | 1.00 | 3.36  | FKBP |
| ATOM | 336 | CD1 | PHE | 36 | -11.660 | 28.108 | 49.295 | 1.00 | 4.33  | FKBP |
| ATOM | 337 | CD2 | PHE | 36 | -12.470 | 27.442 | 47.151 | 1.00 | 7.57  | FKBP |
| ATOM | 338 | CE1 | PHE | 36 | -10.350 | 27.758 | 48.916 | 1.00 | 5.11  | FKBP |
| ATOM | 339 | CE2 | PHE | 36 | -11.167 | 27.092 | 46.766 | 1.00 | 5.95  | FKBP |
| ATOM | 340 | CZ  | PHE | 36 | -10.110 | 27.250 | 47.648 | 1.00 | 2.00  | FKBP |
| ATOM | 341 | C   | PHE | 36 | -15.553 | 26.696 | 47.861 | 1.00 | 11.24 | FKBP |
| ATOM | 342 | O   | PHE | 36 | -16.499 | 27.050 | 47.152 | 1.00 | 9.15  | FKBP |
| ATOM | 343 | N   | ASP | 37 | -14.972 | 25.507 | 47.738 | 1.00 | 11.21 | FKBP |
| ATOM | 344 | H   | ASP | 37 | -14.365 | 25.202 | 48.445 | 0.00 | 0.00  | FKBP |
| ATOM | 345 | CA  | ASP | 37 | -15.201 | 24.672 | 46.568 | 1.00 | 8.81  | FKBP |
| ATOM | 346 | CB  | ASP | 37 | -14.340 | 25.220 | 45.416 | 1.00 | 12.70 | FKBP |
| ATOM | 347 | CG  | ASP | 37 | -14.583 | 24.518 | 44.091 | 1.00 | 11.57 | FKBP |
| ATOM | 348 | OD1 | ASP | 37 | -15.679 | 23.968 | 43.855 | 1.00 | 7.88  | FKBP |
| ATOM | 349 | OD2 | ASP | 37 | -13.665 | 24.565 | 43.254 | 1.00 | 15.66 | FKBP |
| ATOM | 350 | C   | ASP | 37 | -14.874 | 23.199 | 46.864 | 1.00 | 2.00  | FKBP |

Figure 4: A-8

```
ATOM    351  O    ASP    37     -13.905   22.904   47.545  1.00   2.01      FKBP
ATOM    352  N    SER    38     -15.751   22.291   46.450  1.00   2.52      FKBP
ATOM    353  H    SER    38     -16.607   22.613   46.095  0.00   0.00      FKBP
ATOM    354  CA   SER    38     -15.461   20.850   46.493  1.00   2.33      FKBP
ATOM    355  CB   SER    38     -15.954   20.223   47.800  1.00  12.19      FKBP
ATOM    356  OG   SER    38     -15.979   18.804   47.722  1.00   9.54      FKBP
ATOM    357  HG   SER    38     -15.613   18.490   48.571  0.00   0.00      FKBP
ATOM    358  C    SER    38     -16.108   20.110   45.349  1.00   2.00      FKBP
ATOM    359  O    SER    38     -17.313   20.210   45.168  1.00   2.31      FKBP
ATOM    360  N    SER    39     -15.339   19.252   44.684  1.00   2.00      FKBP
ATOM    361  H    SER    39     -14.397   19.223   44.967  0.00   0.00      FKBP
ATOM    362  CA   SER    39     -15.840   18.414   43.584  1.00   3.72      FKBP
ATOM    363  CB   SER    39     -14.682   17.758   42.825  1.00   3.50      FKBP
ATOM    364  OG   SER    39     -13.861   16.976   43.683  1.00   3.28      FKBP
ATOM    365  HG   SER    39     -14.195   17.054   44.589  0.00   0.00      FKBP
ATOM    366  C    SER    39     -16.762   17.317   44.088  1.00   9.63      FKBP
ATOM    367  O    SER    39     -17.547   16.751   43.324  1.00   6.74      FKBP
ATOM    368  N    ARG    40     -16.624   16.994   45.376  1.00  13.48      FKBP
ATOM    369  H    ARG    40     -16.027   17.536   45.944  0.00   0.00      FKBP
ATOM    370  CA   ARG    40     -17.441   15.972   46.025  1.00  12.15      FKBP
ATOM    371  CB   ARG    40     -16.800   15.538   47.345  1.00   4.43      FKBP
ATOM    372  CG   ARG    40     -15.385   15.003   47.220  1.00   2.00      FKBP
ATOM    373  CD   ARG    40     -14.978   14.243   48.484  1.00   3.29      FKBP
ATOM    374  NE   ARG    40     -13.546   13.940   48.561  1.00   4.66      FKBP
ATOM    375  HE   ARG    40     -12.924   14.683   48.660  0.00   0.00      FKBP
ATOM    376  CZ   ARG    40     -13.031   12.714   48.497  1.00   2.00      FKBP
ATOM    377  NH1  ARG    40     -11.727   12.527   48.631  1.00   2.00      FKBP
ATOM    378  HH11 ARG    40     -11.112   13.308   48.782  0.00   0.00      FKBP
ATOM    379  HH12 ARG    40     -11.374   11.597   48.585  0.00   0.00      FKBP
ATOM    380  NH2  ARG    40     -13.812   11.673   48.262  1.00   2.00      FKBP
ATOM    381  HH21 ARG    40     -14.794   11.785   48.128  0.00   0.00      FKBP
ATOM    382  HH22 ARG    40     -13.417   10.752   48.214  0.00   0.00      FKBP
ATOM    383  C    ARG    40     -18.883   16.433   46.270  1.00  17.11      FKBP
ATOM    384  O    ARG    40     -19.798   15.612   46.350  1.00  17.06      FKBP
ATOM    385  N    ASP    41     -19.085   17.746   46.370  1.00  20.79      FKBP
ATOM    386  H    ASP    41     -18.307   18.340   46.438  0.00   0.00      FKBP
ATOM    387  CA   ASP    41     -20.435   18.315   46.454  1.00  26.68      FKBP
ATOM    388  CB   ASP    41     -20.375   19.784   46.879  1.00  26.55      FKBP
ATOM    389  CG   ASP    41     -19.641   19.993   48.195  1.00  34.97      FKBP
ATOM    390  OD1  ASP    41     -19.251   19.001   48.852  1.00  38.14      FKBP
ATOM    391  OD2  ASP    41     -19.426   21.167   48.559  1.00  36.52      FKBP
ATOM    392  C    ASP    41     -21.187   18.206   45.124  1.00  30.48      FKBP
ATOM    393  O    ASP    41     -22.416   18.085   45.106  1.00  31.53      FKBP
ATOM    394  N    ARG    42     -20.447   18.307   44.018  1.00  31.99      FKBP
ATOM    395  H    ARG    42     -19.519   18.595   44.120  0.00   0.00      FKBP
ATOM    396  CA   ARG    42     -21.006   18.124   42.676  1.00  26.25      FKBP
ATOM    397  CB   ARG    42     -20.168   18.865   41.625  1.00  22.17      FKBP
ATOM    398  CG   ARG    42     -19.815   20.302   41.976  1.00  26.16      FKBP
ATOM    399  CD   ARG    42     -18.697   20.840   41.089  1.00  29.95      FKBP
ATOM    400  NE   ARG    42     -17.703   19.814   40.769  1.00  40.62      FKBP
```

Figure 4: A-9

| | | | | | | | | | | |
|---|---|---|---|---|---|---|---|---|---|---|
| ATOM | 401 | HE | ARG | 42 | -17.911 | 18.869 | 40.922 | 0.00 | 0.00 | FKBP |
| ATOM | 402 | CZ | ARG | 42 | -16.491 | 20.058 | 40.273 | 1.00 | 44.80 | FKBP |
| ATOM | 403 | NH1 | ARG | 42 | -15.684 | 19.045 | 39.978 | 1.00 | 43.55 | FKBP |
| ATOM | 404 | HH11 | ARG | 42 | -16.002 | 18.108 | 40.125 | 0.00 | 0.00 | FKBP |
| ATOM | 405 | HH12 | ARG | 42 | -14.773 | 19.213 | 39.600 | 0.00 | 0.00 | FKBP |
| ATOM | 406 | NH2 | ARG | 42 | -16.070 | 21.306 | 40.089 | 1.00 | 47.04 | FKBP |
| ATOM | 407 | HH21 | ARG | 42 | -16.655 | 22.080 | 40.328 | 0.00 | 0.00 | FKBP |
| ATOM | 408 | HH22 | ARG | 42 | -15.156 | 21.465 | 39.719 | 0.00 | 0.00 | FKBP |
| ATOM | 409 | C | ARG | 42 | -21.051 | 16.642 | 42.320 | 1.00 | 25.62 | FKBP |
| ATOM | 410 | O | ARG | 42 | -21.679 | 16.252 | 41.338 | 1.00 | 29.04 | FKBP |
| ATOM | 411 | N | ASN | 43 | -20.302 | 15.832 | 43.064 | 1.00 | 20.94 | FKBP |
| ATOM | 412 | H | ASN | 43 | -19.786 | 16.217 | 43.793 | 0.00 | 0.00 | FKBP |
| ATOM | 413 | CA | ASN | 43 | -20.290 | 14.392 | 42.840 | 1.00 | 21.52 | FKBP |
| ATOM | 414 | CB | ASN | 43 | -21.724 | 13.852 | 42.869 | 1.00 | 23.52 | FKBP |
| ATOM | 415 | CG | ASN | 43 | -21.808 | 12.455 | 43.431 | 1.00 | 28.90 | FKBP |
| ATOM | 416 | OD1 | ASN | 43 | -20.789 | 11.802 | 43.662 | 1.00 | 28.67 | FKBP |
| ATOM | 417 | ND2 | ASN | 43 | -23.025 | 11.987 | 43.662 | 1.00 | 33.33 | FKBP |
| ATOM | 418 | HD21 | ASN | 43 | -23.786 | 12.557 | 43.466 | 0.00 | 0.00 | FKBP |
| ATOM | 419 | HD22 | ASN | 43 | -23.041 | 11.094 | 44.043 | 0.00 | 0.00 | FKBP |
| ATOM | 420 | C | ASN | 43 | -19.628 | 14.078 | 41.498 | 1.00 | 20.93 | FKBP |
| ATOM | 421 | O | ASN | 43 | -20.087 | 13.228 | 40.740 | 1.00 | 21.51 | FKBP |
| ATOM | 422 | N | LYS | 44 | -18.475 | 14.696 | 41.275 | 1.00 | 20.83 | FKBP |
| ATOM | 423 | H | LYS | 44 | -18.152 | 15.288 | 41.984 | 0.00 | 0.00 | FKBP |
| ATOM | 424 | CA | LYS | 44 | -17.874 | 14.757 | 39.947 | 1.00 | 19.75 | FKBP |
| ATOM | 425 | CB | LYS | 44 | -18.554 | 15.879 | 39.148 | 1.00 | 24.43 | FKBP |
| ATOM | 426 | CG | LYS | 44 | -18.478 | 15.755 | 37.638 | 1.00 | 23.61 | FKBP |
| ATOM | 427 | CD | LYS | 44 | -18.796 | 17.084 | 36.965 | 1.00 | 29.64 | FKBP |
| ATOM | 428 | CE | LYS | 44 | -20.212 | 17.565 | 37.282 | 1.00 | 34.29 | FKBP |
| ATOM | 429 | NZ | LYS | 44 | -20.543 | 18.848 | 36.583 | 1.00 | 38.07 | FKBP |
| ATOM | 430 | HZ1 | LYS | 44 | -20.497 | 18.697 | 35.555 | 0.00 | 0.00 | FKBP |
| ATOM | 431 | HZ2 | LYS | 44 | -19.853 | 19.580 | 36.854 | 0.00 | 0.00 | FKBP |
| ATOM | 432 | HZ3 | LYS | 44 | -21.496 | 19.168 | 36.846 | 0.00 | 0.00 | FKBP |
| ATOM | 433 | C | LYS | 44 | -16.361 | 15.014 | 40.049 | 1.00 | 17.91 | FKBP |
| ATOM | 434 | O | LYS | 44 | -15.928 | 16.029 | 40.596 | 1.00 | 21.43 | FKBP |
| ATOM | 435 | N | PRO | 45 | -15.545 | 14.014 | 39.695 | 1.00 | 16.30 | FKBP |
| ATOM | 436 | CD | PRO | 45 | -15.909 | 12.612 | 39.438 | 1.00 | 17.34 | FKBP |
| ATOM | 437 | CA | PRO | 45 | -14.093 | 14.182 | 39.830 | 1.00 | 17.48 | FKBP |
| ATOM | 438 | CB | PRO | 45 | -13.539 | 12.779 | 39.557 | 1.00 | 14.90 | FKBP |
| ATOM | 439 | CG | PRO | 45 | -14.679 | 11.871 | 39.886 | 1.00 | 19.40 | FKBP |
| ATOM | 440 | C | PRO | 45 | -13.496 | 15.228 | 38.887 | 1.00 | 15.55 | FKBP |
| ATOM | 441 | O | PRO | 45 | -13.942 | 15.399 | 37.753 | 1.00 | 17.90 | FKBP |
| ATOM | 442 | N | PHE | 46 | -12.501 | 15.942 | 39.389 | 1.00 | 11.92 | FKBP |
| ATOM | 443 | H | PHE | 46 | -12.151 | 15.695 | 40.268 | 0.00 | 0.00 | FKBP |
| ATOM | 444 | CA | PHE | 46 | -11.825 | 16.989 | 38.637 | 1.00 | 10.26 | FKBP |
| ATOM | 445 | CB | PHE | 46 | -11.346 | 18.068 | 39.615 | 1.00 | 7.26 | FKBP |
| ATOM | 446 | CG | PHE | 46 | -10.549 | 19.165 | 38.980 | 1.00 | 2.00 | FKBP |
| ATOM | 447 | CD1 | PHE | 46 | -9.192 | 19.284 | 39.246 | 1.00 | 2.00 | FKBP |
| ATOM | 448 | CD2 | PHE | 46 | -11.180 | 20.149 | 38.222 | 1.00 | 2.00 | FKBP |
| ATOM | 449 | CE1 | PHE | 46 | -8.472 | 20.369 | 38.779 | 1.00 | 2.30 | FKBP |
| ATOM | 450 | CE2 | PHE | 46 | -10.475 | 21.243 | 37.749 | 1.00 | 2.00 | FKBP |

Figure 4: A-10

| | | | | | | | | | | |
|---|---|---|---|---|---|---|---|---|---|---|
| ATOM | 451 | CZ | PHE | 46 | -9.117 | 21.357 | 38.030 | 1.00 | 5.96 | FKBP |
| ATOM | 452 | C | PHE | 46 | -10.644 | 16.371 | 37.898 | 1.00 | 10.45 | FKBP |
| ATOM | 453 | O | PHE | 46 | -9.984 | 15.479 | 38.421 | 1.00 | 16.71 | FKBP |
| ATOM | 454 | N | LYS | 47 | -10.421 | 16.782 | 36.655 | 1.00 | 9.72 | FKBP |
| ATOM | 455 | H | LYS | 47 | -11.004 | 17.458 | 36.253 | 0.00 | 0.00 | FKBP |
| ATOM | 456 | CA | LYS | 47 | -9.293 | 16.255 | 35.893 | 1.00 | 4.83 | FKBP |
| ATOM | 457 | CB | LYS | 47 | -9.770 | 15.421 | 34.700 | 1.00 | 5.22 | FKBP |
| ATOM | 458 | CG | LYS | 47 | -10.510 | 14.147 | 35.058 | 1.00 | 8.65 | FKBP |
| ATOM | 459 | CD | LYS | 47 | -11.587 | 13.853 | 34.032 | 1.00 | 11.93 | FKBP |
| ATOM | 460 | CE | LYS | 47 | -11.326 | 12.543 | 33.312 | 1.00 | 10.86 | FKBP |
| ATOM | 461 | NZ | LYS | 47 | -11.608 | 11.397 | 34.216 | 1.00 | 15.06 | FKBP |
| ATOM | 462 | HZ1 | LYS | 47 | -12.594 | 11.462 | 34.542 | 0.00 | 0.00 | FKBP |
| ATOM | 463 | HZ2 | LYS | 47 | -10.981 | 11.442 | 35.042 | 0.00 | 0.00 | FKBP |
| ATOM | 464 | HZ3 | LYS | 47 | -11.471 | 10.498 | 33.712 | 0.00 | 0.00 | FKBP |
| ATOM | 465 | C | LYS | 47 | -8.435 | 17.389 | 35.395 | 1.00 | 2.00 | FKBP |
| ATOM | 466 | O | LYS | 47 | -8.943 | 18.449 | 35.061 | 1.00 | 2.00 | FKBP |
| ATOM | 467 | N | PHE | 48 | -7.125 | 17.205 | 35.472 | 1.00 | 2.00 | FKBP |
| ATOM | 468 | H | PHE | 48 | -6.799 | 16.438 | 35.994 | 0.00 | 0.00 | FKBP |
| ATOM | 469 | CA | PHE | 48 | -6.191 | 18.157 | 34.896 | 1.00 | 6.26 | FKBP |
| ATOM | 470 | CB | PHE | 48 | -5.964 | 19.323 | 35.875 | 1.00 | 2.45 | FKBP |
| ATOM | 471 | CG | PHE | 48 | -4.948 | 19.036 | 36.942 | 1.00 | 4.20 | FKBP |
| ATOM | 472 | CD1 | PHE | 48 | -5.254 | 18.188 | 38.005 | 1.00 | 2.00 | FKBP |
| ATOM | 473 | CD2 | PHE | 48 | -3.650 | 19.548 | 36.837 | 1.00 | 2.00 | FKBP |
| ATOM | 474 | CE1 | PHE | 48 | -4.282 | 17.837 | 38.936 | 1.00 | 2.00 | FKBP |
| ATOM | 475 | CE2 | PHE | 48 | -2.664 | 19.200 | 37.769 | 1.00 | 2.59 | FKBP |
| ATOM | 476 | CZ | PHE | 48 | -2.983 | 18.340 | 38.817 | 1.00 | 2.53 | FKBP |
| ATOM | 477 | C | PHE | 48 | -4.866 | 17.469 | 34.538 | 1.00 | 10.81 | FKBP |
| ATOM | 478 | O | PHE | 48 | -4.480 | 16.476 | 35.159 | 1.00 | 16.65 | FKBP |
| ATOM | 479 | N | MET | 49 | -4.181 | 17.984 | 33.526 | 1.00 | 13.39 | FKBP |
| ATOM | 480 | H | MET | 49 | -4.543 | 18.774 | 33.084 | 0.00 | 0.00 | FKBP |
| ATOM | 481 | CA | MET | 49 | -2.892 | 17.437 | 33.113 | 1.00 | 16.66 | FKBP |
| ATOM | 482 | CB | MET | 49 | -2.690 | 17.663 | 31.614 | 1.00 | 22.76 | FKBP |
| ATOM | 483 | CG | MET | 49 | -1.538 | 16.885 | 31.016 | 1.00 | 32.61 | FKBP |
| ATOM | 484 | SD | MET | 49 | -0.985 | 17.585 | 29.454 | 1.00 | 46.48 | FKBP |
| ATOM | 485 | CE | MET | 49 | -0.812 | 16.105 | 28.435 | 1.00 | 45.16 | FKBP |
| ATOM | 486 | C | MET | 49 | -1.768 | 18.109 | 33.898 | 1.00 | 16.05 | FKBP |
| ATOM | 487 | O | MET | 49 | -1.749 | 19.332 | 34.046 | 1.00 | 17.38 | FKBP |
| ATOM | 488 | N | LEU | 50 | -0.852 | 17.314 | 34.433 | 1.00 | 16.03 | FKBP |
| ATOM | 489 | H | LEU | 50 | -0.925 | 16.348 | 34.258 | 0.00 | 0.00 | FKBP |
| ATOM | 490 | CA | LEU | 50 | 0.166 | 17.848 | 35.336 | 1.00 | 16.25 | FKBP |
| ATOM | 491 | CB | LEU | 50 | 0.587 | 16.777 | 36.350 | 1.00 | 16.08 | FKBP |
| ATOM | 492 | CG | LEU | 50 | 1.737 | 17.151 | 37.290 | 1.00 | 15.77 | FKBP |
| ATOM | 493 | CD1 | LEU | 50 | 1.189 | 17.731 | 38.587 | 1.00 | 17.22 | FKBP |
| ATOM | 494 | CD2 | LEU | 50 | 2.591 | 15.923 | 37.561 | 1.00 | 17.09 | FKBP |
| ATOM | 495 | C | LEU | 50 | 1.398 | 18.380 | 34.606 | 1.00 | 18.27 | FKBP |
| ATOM | 496 | O | LEU | 50 | 2.130 | 17.629 | 33.962 | 1.00 | 17.62 | FKBP |
| ATOM | 497 | N | GLY | 51 | 1.659 | 19.671 | 34.773 | 1.00 | 24.68 | FKBP |
| ATOM | 498 | H | GLY | 51 | 1.071 | 20.196 | 35.347 | 0.00 | 0.00 | FKBP |
| ATOM | 499 | CA | GLY | 51 | 2.832 | 20.281 | 34.163 | 1.00 | 28.29 | FKBP |
| ATOM | 500 | C | GLY | 51 | 2.511 | 21.451 | 33.246 | 1.00 | 30.06 | FKBP |

Figure 4: A-11

```
ATOM    501  O    GLY   51       3.312   22.367   33.092  1.00 31.10      FKBP
ATOM    502  N    LYS   52       1.283   21.482   32.739  1.00 31.85      FKBP
ATOM    503  H    LYS   52       0.651   20.805   33.051  0.00  0.00      FKBP
ATOM    504  CA   LYS   52       0.883   22.452   31.724  1.00 30.54      FKBP
ATOM    505  CB   LYS   52      -0.281   21.887   30.899  1.00 33.91      FKBP
ATOM    506  CG   LYS   52      -0.110   20.427   30.479  1.00 38.74      FKBP
ATOM    507  CD   LYS   52       1.015   20.263   29.458  1.00 44.12      FKBP
ATOM    508  CE   LYS   52       1.708   18.913   29.584  1.00 44.68      FKBP
ATOM    509  NZ   LYS   52       2.954   18.849   28.767  1.00 46.84      FKBP
ATOM    510  HZ1  LYS   52       3.632   19.546   29.134  0.00  0.00      FKBP
ATOM    511  HZ2  LYS   52       2.732   19.066   27.773  0.00  0.00      FKBP
ATOM    512  HZ3  LYS   52       3.361   17.895   28.831  0.00  0.00      FKBP
ATOM    513  C    LYS   52       0.475   23.795   32.323  1.00 27.06      FKBP
ATOM    514  O    LYS   52      -0.349   24.498   31.741  1.00 30.79      FKBP
ATOM    515  N    GLN   53       1.025   24.130   33.490  1.00 21.58      FKBP
ATOM    516  H    GLN   53       1.847   23.671   33.747  0.00  0.00      FKBP
ATOM    517  CA   GLN   53       0.572   25.282   34.279  1.00 18.83      FKBP
ATOM    518  CB   GLN   53       1.219   26.571   33.768  1.00 25.35      FKBP
ATOM    519  CG   GLN   53       2.599   26.848   34.333  1.00 34.50      FKBP
ATOM    520  CD   GLN   53       3.585   25.737   34.025  1.00 42.12      FKBP
ATOM    521  OE1  GLN   53       3.854   25.432   32.865  1.00 46.61      FKBP
ATOM    522  NE2  GLN   53       4.096   25.098   35.067  1.00 46.53      FKBP
ATOM    523  HE21 GLN   53       3.837   25.352   35.970  0.00  0.00      FKBP
ATOM    524  HE22 GLN   53       4.723   24.391   34.821  0.00  0.00      FKBP
ATOM    525  C    GLN   53      -0.950   25.457   34.313  1.00 15.57      FKBP
ATOM    526  O    GLN   53      -1.456   26.570   34.380  1.00 17.17      FKBP
ATOM    527  N    GLU   54      -1.672   24.344   34.338  1.00 12.00      FKBP
ATOM    528  H    GLU   54      -1.188   23.505   34.304  0.00  0.00      FKBP
ATOM    529  CA   GLU   54      -3.126   24.378   34.306  1.00  6.49      FKBP
ATOM    530  CB   GLU   54      -3.666   23.022   33.878  1.00  6.66      FKBP
ATOM    531  CG   GLU   54      -4.296   23.020   32.516  1.00  4.63      FKBP
ATOM    532  CD   GLU   54      -4.414   21.628   31.960  1.00 11.57      FKBP
ATOM    533  OE1  GLU   54      -3.543   21.242   31.157  1.00 18.19      FKBP
ATOM    534  OE2  GLU   54      -5.339   20.896   32.368  1.00 10.83      FKBP
ATOM    535  C    GLU   54      -3.741   24.762   35.642  1.00  5.69      FKBP
ATOM    536  O    GLU   54      -4.873   25.238   35.696  1.00  4.44      FKBP
ATOM    537  N    VAL   55      -3.035   24.444   36.722  1.00  4.70      FKBP
ATOM    538  H    VAL   55      -2.142   24.084   36.580  0.00  0.00      FKBP
ATOM    539  CA   VAL   55      -3.513   24.731   38.071  1.00  6.95      FKBP
ATOM    540  CB   VAL   55      -3.774   23.446   38.849  1.00  3.43      FKBP
ATOM    541  CG1  VAL   55      -4.995   22.759   38.309  1.00  9.22      FKBP
ATOM    542  CG2  VAL   55      -2.573   22.538   38.761  1.00  2.21      FKBP
ATOM    543  C    VAL   55      -2.500   25.559   38.849  1.00  9.75      FKBP
ATOM    544  O    VAL   55      -1.369   25.737   38.408  1.00  9.34      FKBP
ATOM    545  N    ILE   56      -2.887   26.026   40.031  1.00 12.04      FKBP
ATOM    546  H    ILE   56      -3.799   25.844   40.322  0.00  0.00      FKBP
ATOM    547  CA   ILE   56      -1.964   26.785   40.869  1.00 10.94      FKBP
ATOM    548  CB   ILE   56      -2.674   27.365   42.123  1.00  9.38      FKBP
ATOM    549  CG2  ILE   56      -3.665   28.449   41.701  1.00  9.44      FKBP
ATOM    550  CG1  ILE   56      -3.377   26.263   42.920  1.00  4.02      FKBP
```

Figure 4: A-12

| | | | | | | | | | | |
|---|---|---|---|---|---|---|---|---|---|---|
| ATOM | 551 | CD1 | ILE | 56 | -4.003 | 26.756 | 44.206 | 1.00 | 2.00 | FKBP |
| ATOM | 552 | C | ILE | 56 | -0.734 | 25.962 | 41.286 | 1.00 | 12.55 | FKBP |
| ATOM | 553 | O | ILE | 56 | -0.759 | 24.729 | 41.270 | 1.00 | 15.13 | FKBP |
| ATOM | 554 | N | ARG | 57 | 0.353 | 26.651 | 41.615 | 1.00 | 10.58 | FKBP |
| ATOM | 555 | H | ARG | 57 | 0.284 | 27.627 | 41.637 | 0.00 | 0.00 | FKBP |
| ATOM | 556 | CA | ARG | 57 | 1.648 | 26.013 | 41.850 | 1.00 | 12.39 | FKBP |
| ATOM | 557 | CB | ARG | 57 | 2.707 | 27.091 | 42.058 | 1.00 | 13.28 | FKBP |
| ATOM | 558 | CG | ARG | 57 | 4.115 | 26.573 | 42.013 | 1.00 | 16.07 | FKBP |
| ATOM | 559 | CD | ARG | 57 | 5.090 | 27.708 | 42.068 | 1.00 | 18.63 | FKBP |
| ATOM | 560 | NE | ARG | 57 | 6.447 | 27.196 | 42.189 | 1.00 | 29.56 | FKBP |
| ATOM | 561 | HE | ARG | 57 | 6.567 | 26.228 | 42.278 | 0.00 | 0.00 | FKBP |
| ATOM | 562 | CZ | ARG | 57 | 7.535 | 27.957 | 42.208 | 1.00 | 29.74 | FKBP |
| ATOM | 563 | NH1 | ARG | 57 | 8.728 | 27.390 | 42.332 | 1.00 | 34.84 | FKBP |
| ATOM | 564 | HH11 | ARG | 57 | 8.794 | 26.398 | 42.443 | 0.00 | 0.00 | FKBP |
| ATOM | 565 | HH12 | ARG | 57 | 9.551 | 27.954 | 42.380 | 0.00 | 0.00 | FKBP |
| ATOM | 566 | NH2 | ARG | 57 | 7.430 | 29.277 | 42.124 | 1.00 | 24.22 | FKBP |
| ATOM | 567 | HH21 | ARG | 57 | 6.534 | 29.712 | 42.038 | 0.00 | 0.00 | FKBP |
| ATOM | 568 | HH22 | ARG | 57 | 8.258 | 29.836 | 42.149 | 0.00 | 0.00 | FKBP |
| ATOM | 569 | C | ARG | 57 | 1.700 | 25.006 | 43.014 | 1.00 | 15.27 | FKBP |
| ATOM | 570 | O | ARG | 57 | 2.321 | 23.946 | 42.901 | 1.00 | 16.77 | FKBP |
| ATOM | 571 | N | GLY | 58 | 1.084 | 25.349 | 44.142 | 1.00 | 13.48 | FKBP |
| ATOM | 572 | H | GLY | 58 | 0.719 | 26.253 | 44.227 | 0.00 | 0.00 | FKBP |
| ATOM | 573 | CA | GLY | 58 | 0.973 | 24.402 | 45.240 | 1.00 | 12.25 | FKBP |
| ATOM | 574 | C | GLY | 58 | 0.326 | 23.080 | 44.849 | 1.00 | 9.23 | FKBP |
| ATOM | 575 | O | GLY | 58 | 0.633 | 22.043 | 45.438 | 1.00 | 8.04 | FKBP |
| ATOM | 576 | N | TRP | 59 | -0.567 | 23.124 | 43.856 | 1.00 | 6.52 | FKBP |
| ATOM | 577 | H | TRP | 59 | -0.838 | 24.004 | 43.525 | 0.00 | 0.00 | FKBP |
| ATOM | 578 | CA | TRP | 59 | -1.177 | 21.927 | 43.269 | 1.00 | 2.00 | FKBP |
| ATOM | 579 | CB | TRP | 59 | -2.399 | 22.294 | 42.443 | 1.00 | 2.00 | FKBP |
| ATOM | 580 | CG | TRP | 59 | -3.672 | 22.138 | 43.172 | 1.00 | 2.87 | FKBP |
| ATOM | 581 | CD2 | TRP | 59 | -4.707 | 21.189 | 42.889 | 1.00 | 4.49 | FKBP |
| ATOM | 582 | CE2 | TRP | 59 | -5.725 | 21.386 | 43.843 | 1.00 | 5.98 | FKBP |
| ATOM | 583 | CE3 | TRP | 59 | -4.874 | 20.193 | 41.921 | 1.00 | 2.00 | FKBP |
| ATOM | 584 | CD1 | TRP | 59 | -4.093 | 22.857 | 44.252 | 1.00 | 2.00 | FKBP |
| ATOM | 585 | NE1 | TRP | 59 | -5.327 | 22.413 | 44.659 | 1.00 | 4.48 | FKBP |
| ATOM | 586 | HE1 | TRP | 59 | -5.830 | 22.768 | 45.422 | 0.00 | 0.00 | FKBP |
| ATOM | 587 | CZ2 | TRP | 59 | -6.897 | 20.615 | 43.859 | 1.00 | 7.28 | FKBP |
| ATOM | 588 | CZ3 | TRP | 59 | -6.043 | 19.433 | 41.939 | 1.00 | 4.10 | FKBP |
| ATOM | 589 | CH2 | TRP | 59 | -7.033 | 19.648 | 42.900 | 1.00 | 2.01 | FKBP |
| ATOM | 590 | C | TRP | 59 | -0.215 | 21.196 | 42.365 | 1.00 | 3.20 | FKBP |
| ATOM | 591 | O | TRP | 59 | -0.186 | 19.969 | 42.345 | 1.00 | 9.79 | FKBP |
| ATOM | 592 | N | GLU | 60 | 0.507 | 21.955 | 41.550 | 1.00 | 3.19 | FKBP |
| ATOM | 593 | H | GLU | 60 | 0.323 | 22.919 | 41.539 | 0.00 | 0.00 | FKBP |
| ATOM | 594 | CA | GLU | 60 | 1.484 | 21.388 | 40.636 | 1.00 | 5.73 | FKBP |
| ATOM | 595 | CB | GLU | 60 | 2.142 | 22.502 | 39.819 | 1.00 | 10.18 | FKBP |
| ATOM | 596 | CG | GLU | 60 | 2.585 | 22.086 | 38.415 | 1.00 | 13.55 | FKBP |
| ATOM | 597 | CD | GLU | 60 | 1.463 | 22.147 | 37.398 | 1.00 | 16.71 | FKBP |
| ATOM | 598 | OE1 | GLU | 60 | 1.649 | 22.793 | 36.348 | 1.00 | 22.45 | FKBP |
| ATOM | 599 | OE2 | GLU | 60 | 0.393 | 21.551 | 37.640 | 1.00 | 19.83 | FKBP |
| ATOM | 600 | C | GLU | 60 | 2.538 | 20.587 | 41.395 | 1.00 | 8.89 | FKBP |

Figure 4: A-13

| | | | | | | | | | | |
|---|---|---|---|---|---|---|---|---|---|---|
| ATOM | 601 | O    | GLU | 60 | 2.703  | 19.395 | 41.150 | 1.00 | 14.67 | FKBP |
| ATOM | 602 | N    | GLU | 61 | 3.116  | 21.189 | 42.428 | 1.00 | 11.93 | FKBP |
| ATOM | 603 | H    | GLU | 61 | 2.859  | 22.117 | 42.606 | 0.00 | 0.00  | FKBP |
| ATOM | 604 | CA   | GLU | 61 | 4.123  | 20.510 | 43.249 | 1.00 | 15.22 | FKBP |
| ATOM | 605 | CB   | GLU | 61 | 5.053  | 21.533 | 43.916 | 1.00 | 18.18 | FKBP |
| ATOM | 606 | CG   | GLU | 61 | 5.177  | 22.868 | 43.171 | 1.00 | 28.20 | FKBP |
| ATOM | 607 | CD   | GLU | 61 | 6.615  | 23.314 | 42.926 | 1.00 | 31.43 | FKBP |
| ATOM | 608 | OE1  | GLU | 61 | 7.478  | 23.101 | 43.807 | 1.00 | 35.07 | FKBP |
| ATOM | 609 | OE2  | GLU | 61 | 6.865  | 23.933 | 41.867 | 1.00 | 34.62 | FKBP |
| ATOM | 610 | C    | GLU | 61 | 3.519  | 19.581 | 44.315 | 1.00 | 14.96 | FKBP |
| ATOM | 611 | O    | GLU | 61 | 4.101  | 18.558 | 44.663 | 1.00 | 21.59 | FKBP |
| ATOM | 612 | N    | GLY | 62 | 2.355  | 19.938 | 44.840 | 1.00 | 16.29 | FKBP |
| ATOM | 613 | H    | GLY | 62 | 1.970  | 20.809 | 44.617 | 0.00 | 0.00  | FKBP |
| ATOM | 614 | CA   | GLY | 62 | 1.687  | 19.077 | 45.801 | 1.00 | 12.82 | FKBP |
| ATOM | 615 | C    | GLY | 62 | 1.281  | 17.734 | 45.219 | 1.00 | 12.55 | FKBP |
| ATOM | 616 | O    | GLY | 62 | 1.782  | 16.697 | 45.639 | 1.00 | 12.58 | FKBP |
| ATOM | 617 | N    | VAL | 63 | 0.438  | 17.764 | 44.190 | 1.00 | 12.60 | FKBP |
| ATOM | 618 | H    | VAL | 63 | 0.172  | 18.639 | 43.830 | 0.00 | 0.00  | FKBP |
| ATOM | 619 | CA   | VAL | 63 | -0.092 | 16.550 | 43.570 | 1.00 | 12.62 | FKBP |
| ATOM | 620 | CB   | VAL | 63 | -1.164 | 16.899 | 42.511 | 1.00 | 7.73  | FKBP |
| ATOM | 621 | CG1  | VAL | 63 | -1.788 | 15.628 | 41.954 | 1.00 | 7.25  | FKBP |
| ATOM | 622 | CG2  | VAL | 63 | -2.234 | 17.780 | 43.122 | 1.00 | 3.26  | FKBP |
| ATOM | 623 | C    | VAL | 63 | 0.996  | 15.674 | 42.921 | 1.00 | 15.97 | FKBP |
| ATOM | 624 | O    | VAL | 63 | 0.927  | 14.446 | 42.958 | 1.00 | 18.69 | FKBP |
| ATOM | 625 | N    | ALA | 64 | 2.048  | 16.305 | 42.416 | 1.00 | 15.67 | FKBP |
| ATOM | 626 | H    | ALA | 64 | 2.009  | 17.279 | 42.315 | 0.00 | 0.00  | FKBP |
| ATOM | 627 | CA   | ALA | 64 | 3.196  | 15.570 | 41.905 | 1.00 | 14.59 | FKBP |
| ATOM | 628 | CB   | ALA | 64 | 4.201  | 16.542 | 41.338 | 1.00 | 13.86 | FKBP |
| ATOM | 629 | C    | ALA | 64 | 3.856  | 14.687 | 42.976 | 1.00 | 16.87 | FKBP |
| ATOM | 630 | O    | ALA | 64 | 4.548  | 13.726 | 42.656 | 1.00 | 19.52 | FKBP |
| ATOM | 631 | N    | GLN | 65 | 3.657  | 15.026 | 44.245 | 1.00 | 16.81 | FKBP |
| ATOM | 632 | H    | GLN | 65 | 3.161  | 15.844 | 44.449 | 0.00 | 0.00  | FKBP |
| ATOM | 633 | CA   | GLN | 65 | 4.202  | 14.233 | 45.353 | 1.00 | 14.57 | FKBP |
| ATOM | 634 | CB   | GLN | 65 | 4.359  | 15.097 | 46.606 | 1.00 | 15.78 | FKBP |
| ATOM | 635 | CG   | GLN | 65 | 5.473  | 16.118 | 46.542 | 1.00 | 27.03 | FKBP |
| ATOM | 636 | CD   | GLN | 65 | 5.524  | 16.996 | 47.782 | 1.00 | 35.69 | FKBP |
| ATOM | 637 | OE1  | GLN | 65 | 5.543  | 16.500 | 48.910 | 1.00 | 39.86 | FKBP |
| ATOM | 638 | NE2  | GLN | 65 | 5.516  | 18.307 | 47.580 | 1.00 | 36.82 | FKBP |
| ATOM | 639 | HE21 | GLN | 65 | 5.428  | 18.638 | 46.667 | 0.00 | 0.00  | FKBP |
| ATOM | 640 | HE22 | GLN | 65 | 5.596  | 18.845 | 48.387 | 0.00 | 0.00  | FKBP |
| ATOM | 641 | C    | GLN | 65 | 3.325  | 13.037 | 45.706 | 1.00 | 11.92 | FKBP |
| ATOM | 642 | O    | GLN | 65 | 3.694  | 12.226 | 46.553 | 1.00 | 12.99 | FKBP |
| ATOM | 643 | N    | MET | 66 | 2.094  | 13.034 | 45.210 | 1.00 | 8.83  | FKBP |
| ATOM | 644 | H    | MET | 66 | 1.872  | 13.655 | 44.491 | 0.00 | 0.00  | FKBP |
| ATOM | 645 | CA   | MET | 66 | 1.119  | 12.044 | 45.646 | 1.00 | 9.40  | FKBP |
| ATOM | 646 | CB   | MET | 66 | -0.286 | 12.651 | 45.616 | 1.00 | 5.56  | FKBP |
| ATOM | 647 | CG   | MET | 66 | -0.487 | 13.766 | 46.628 | 1.00 | 3.07  | FKBP |
| ATOM | 648 | SD   | MET | 66 | -2.084 | 14.610 | 46.495 | 1.00 | 12.38 | FKBP |
| ATOM | 649 | CE   | MET | 66 | -3.186 | 13.301 | 46.911 | 1.00 | 12.15 | FKBP |
| ATOM | 650 | C    | MET | 66 | 1.186  | 10.788 | 44.774 | 1.00 | 13.38 | FKBP |

Figure 4: A-14

| ATOM | 651 | O    | MET | 66 | 1.705   | 10.831 | 43.660 | 1.00 | 16.22 | FKBP |
|------|-----|------|-----|----|---------|--------|--------|------|-------|------|
| ATOM | 652 | N    | SER | 67 | 0.832   | 9.643  | 45.346 | 1.00 | 13.44 | FKBP |
| ATOM | 653 | H    | SER | 67 | 0.710   | 9.638  | 46.319 | 0.00 | 0.00  | FKBP |
| ATOM | 654 | CA   | SER | 67 | 0.727   | 8.409  | 44.565 | 1.00 | 11.42 | FKBP |
| ATOM | 655 | CB   | SER | 67 | 1.649   | 7.317  | 45.134 | 1.00 | 7.60  | FKBP |
| ATOM | 656 | OG   | SER | 67 | 1.250   | 6.897  | 46.427 | 1.00 | 7.91  | FKBP |
| ATOM | 657 | HG   | SER | 67 | 1.986   | 7.045  | 47.038 | 0.00 | 0.00  | FKBP |
| ATOM | 658 | C    | SER | 67 | -0.721  | 7.926  | 44.518 | 1.00 | 12.45 | FKBP |
| ATOM | 659 | O    | SER | 67 | -1.556  | 8.364  | 45.309 | 1.00 | 14.85 | FKBP |
| ATOM | 660 | N    | VAL | 68 | -1.055  | 7.115  | 43.523 | 1.00 | 12.38 | FKBP |
| ATOM | 661 | H    | VAL | 68 | -0.361  | 6.855  | 42.883 | 0.00 | 0.00  | FKBP |
| ATOM | 662 | CA   | VAL | 68 | -2.457  | 6.756  | 43.314 | 1.00 | 10.06 | FKBP |
| ATOM | 663 | CB   | VAL | 68 | -2.647  | 5.854  | 42.067 | 1.00 | 5.10  | FKBP |
| ATOM | 664 | CG1  | VAL | 68 | -4.130  | 5.630  | 41.800 | 1.00 | 5.86  | FKBP |
| ATOM | 665 | CG2  | VAL | 68 | -2.010  | 6.489  | 40.874 | 1.00 | 2.65  | FKBP |
| ATOM | 666 | C    | VAL | 68 | -3.080  | 6.069  | 44.532 | 1.00 | 9.51  | FKBP |
| ATOM | 667 | O    | VAL | 68 | -2.603  | 5.033  | 44.999 | 1.00 | 13.72 | FKBP |
| ATOM | 668 | N    | GLY | 69 | -4.190  | 6.630  | 44.992 | 1.00 | 7.92  | FKBP |
| ATOM | 669 | H    | GLY | 69 | -4.587  | 7.362  | 44.469 | 0.00 | 0.00  | FKBP |
| ATOM | 670 | CA   | GLY | 69 | -4.872  | 6.114  | 46.162 | 1.00 | 8.54  | FKBP |
| ATOM | 671 | C    | GLY | 69 | -4.755  | 7.061  | 47.344 | 1.00 | 7.63  | FKBP |
| ATOM | 672 | O    | GLY | 69 | -5.649  | 7.132  | 48.185 | 1.00 | 12.92 | FKBP |
| ATOM | 673 | N    | GLN | 70 | -3.694  | 7.859  | 47.354 | 1.00 | 3.17  | FKBP |
| ATOM | 674 | H    | GLN | 70 | -3.135  | 7.917  | 46.548 | 0.00 | 0.00  | FKBP |
| ATOM | 675 | CA   | GLN | 70 | -3.357  | 8.660  | 48.515 | 1.00 | 2.00  | FKBP |
| ATOM | 676 | CB   | GLN | 70 | -1.927  | 9.161  | 48.395 | 1.00 | 2.57  | FKBP |
| ATOM | 677 | CG   | GLN | 70 | -1.483  | 10.064 | 49.524 | 1.00 | 10.26 | FKBP |
| ATOM | 678 | CD   | GLN | 70 | -0.066  | 10.555 | 49.331 | 1.00 | 10.61 | FKBP |
| ATOM | 679 | OE1  | GLN | 70 | 0.673   | 10.028 | 48.505 | 1.00 | 18.69 | FKBP |
| ATOM | 680 | NE2  | GLN | 70 | 0.310   | 11.586 | 50.067 | 1.00 | 11.45 | FKBP |
| ATOM | 681 | HE21 | GLN | 70 | -0.298  | 11.997 | 50.702 | 0.00 | 0.00  | FKBP |
| ATOM | 682 | HE22 | GLN | 70 | 1.237   | 11.850 | 49.896 | 0.00 | 0.00  | FKBP |
| ATOM | 683 | C    | GLN | 70 | -4.299  | 9.830  | 48.671 | 1.00 | 2.00  | FKBP |
| ATOM | 684 | O    | GLN | 70 | -4.749  | 10.400 | 47.691 | 1.00 | 3.88  | FKBP |
| ATOM | 685 | N    | ARG | 71 | -4.711  | 10.082 | 49.904 | 1.00 | 5.36  | FKBP |
| ATOM | 686 | H    | ARG | 71 | -4.639  | 9.362  | 50.543 | 0.00 | 0.00  | FKBP |
| ATOM | 687 | CA   | ARG | 71 | -5.486  | 11.274 | 50.246 | 1.00 | 5.53  | FKBP |
| ATOM | 688 | CB   | ARG | 71 | -6.753  | 10.873 | 50.997 | 1.00 | 2.00  | FKBP |
| ATOM | 689 | CG   | ARG | 71 | -7.697  | 12.010 | 51.228 | 1.00 | 2.00  | FKBP |
| ATOM | 690 | CD   | ARG | 71 | -9.066  | 11.504 | 51.639 | 1.00 | 3.25  | FKBP |
| ATOM | 691 | NE   | ARG | 71 | -9.812  | 12.542 | 52.347 | 1.00 | 8.85  | FKBP |
| ATOM | 692 | HE   | ARG | 71 | -9.309  | 13.289 | 52.735 | 0.00 | 0.00  | FKBP |
| ATOM | 693 | CZ   | ARG | 71 | -11.134 | 12.564 | 52.475 | 1.00 | 18.29 | FKBP |
| ATOM | 694 | NH1  | ARG | 71 | -11.708 | 13.525 | 53.183 | 1.00 | 25.79 | FKBP |
| ATOM | 695 | HH11 | ARG | 71 | -11.149 | 14.237 | 53.609 | 0.00 | 0.00  | FKBP |
| ATOM | 696 | HH12 | ARG | 71 | -12.702 | 13.542 | 53.282 | 0.00 | 0.00  | FKBP |
| ATOM | 697 | NH2  | ARG | 71 | -11.888 | 11.640 | 51.890 | 1.00 | 23.05 | FKBP |
| ATOM | 698 | HH21 | ARG | 71 | -11.460 | 10.906 | 51.361 | 0.00 | 0.00  | FKBP |
| ATOM | 699 | HH22 | ARG | 71 | -12.879 | 11.654 | 52.011 | 0.00 | 0.00  | FKBP |
| ATOM | 700 | C    | ARG | 71 | -4.650  | 12.208 | 51.114 | 1.00 | 3.03  | FKBP |

Figure 4: A-15

```
ATOM    701  O    ARG    71      -4.006   11.764   52.060   1.00   4.39       FKBP
ATOM    702  N    ALA    72      -4.628   13.489   50.774   1.00   2.46       FKBP
ATOM    703  H    ALA    72      -5.218   13.805   50.054   0.00   0.00       FKBP
ATOM    704  CA   ALA    72      -3.725   14.428   51.425   1.00   2.00       FKBP
ATOM    705  CB   ALA    72      -2.456   14.557   50.636   1.00   2.00       FKBP
ATOM    706  C    ALA    72      -4.326   15.803   51.654   1.00   4.21       FKBP
ATOM    707  O    ALA    72      -5.376   16.145   51.119   1.00  10.57       FKBP
ATOM    708  N    LYS    73      -3.766   16.490   52.632   1.00   8.68       FKBP
ATOM    709  H    LYS    73      -3.101   16.042   53.199   0.00   0.00       FKBP
ATOM    710  CA   LYS    73      -4.121   17.861   52.917   1.00   4.13       FKBP
ATOM    711  CB   LYS    73      -4.387   18.018   54.410   1.00   6.40       FKBP
ATOM    712  CG   LYS    73      -4.104   19.408   54.956   1.00  13.82       FKBP
ATOM    713  CD   LYS    73      -4.807   19.628   56.287   1.00  15.85       FKBP
ATOM    714  CE   LYS    73      -4.136   20.729   57.086   1.00  18.32       FKBP
ATOM    715  NZ   LYS    73      -5.033   21.240   58.148   1.00  22.33       FKBP
ATOM    716  HZ1  LYS    73      -5.238   20.469   58.817   0.00   0.00       FKBP
ATOM    717  HZ2  LYS    73      -5.920   21.583   57.728   0.00   0.00       FKBP
ATOM    718  HZ3  LYS    73      -4.569   22.019   58.657   0.00   0.00       FKBP
ATOM    719  C    LYS    73      -2.943   18.713   52.488   1.00   4.72       FKBP
ATOM    720  O    LYS    73      -1.794   18.396   52.814   1.00   6.20       FKBP
ATOM    721  N    LEU    74      -3.212   19.628   51.566   1.00   6.47       FKBP
ATOM    722  H    LEU    74      -4.064   19.565   51.121   0.00   0.00       FKBP
ATOM    723  CA   LEU    74      -2.218   20.582   51.082   1.00   8.06       FKBP
ATOM    724  CB   LEU    74      -2.303   20.706   49.560   1.00  12.85       FKBP
ATOM    725  CG   LEU    74      -1.440   19.791   48.695   1.00  11.86       FKBP
ATOM    726  CD1  LEU    74      -1.789   18.330   48.947   1.00  11.50       FKBP
ATOM    727  CD2  LEU    74      -1.663   20.157   47.241   1.00  12.57       FKBP
ATOM    728  C    LEU    74      -2.403   21.962   51.695   1.00   8.90       FKBP
ATOM    729  O    LEU    74      -3.449   22.600   51.515   1.00  14.56       FKBP
ATOM    730  N    THR    75      -1.385   22.431   52.405   1.00   7.32       FKBP
ATOM    731  H    THR    75      -0.717   21.784   52.717   0.00   0.00       FKBP
ATOM    732  CA   THR    75      -1.383   23.796   52.913   1.00   6.76       FKBP
ATOM    733  CB   THR    75      -0.905   23.830   54.397   1.00   6.87       FKBP
ATOM    734  OG1  THR    75      -1.957   23.327   55.227   1.00   2.01       FKBP
ATOM    735  HG1  THR    75      -2.720   23.901   55.117   0.00   0.00       FKBP
ATOM    736  CG2  THR    75      -0.556   25.238   54.861   1.00   3.73       FKBP
ATOM    737  C    THR    75      -0.513   24.654   52.000   1.00   6.27       FKBP
ATOM    738  O    THR    75       0.683   24.416   51.846   1.00   5.48       FKBP
ATOM    739  N    ILE    76      -1.180   25.508   51.234   1.00  10.43       FKBP
ATOM    740  H    ILE    76      -2.141   25.633   51.388   0.00   0.00       FKBP
ATOM    741  CA   ILE    76      -0.542   26.284   50.167   1.00  11.16       FKBP
ATOM    742  CB   ILE    76      -1.326   26.090   48.830   1.00   6.31       FKBP
ATOM    743  CG2  ILE    76      -0.653   26.827   47.719   1.00   9.44       FKBP
ATOM    744  CG1  ILE    76      -1.388   24.601   48.459   1.00   5.62       FKBP
ATOM    745  CD1  ILE    76      -2.630   24.205   47.691   1.00   2.00       FKBP
ATOM    746  C    ILE    76      -0.454   27.788   50.522   1.00  12.21       FKBP
ATOM    747  O    ILE    76      -1.476   28.460   50.752   1.00  13.89       FKBP
ATOM    748  N    SER    77       0.768   28.287   50.692   1.00  10.50       FKBP
ATOM    749  H    SER    77       1.535   27.692   50.566   0.00   0.00       FKBP
ATOM    750  CA   SER    77       0.947   29.700   51.009   1.00  11.73       FKBP
```

Figure 4: A-16

| | | | | | | | | | |
|---|---|---|---|---|---|---|---|---|---|
| ATOM | 751 | CB | SER | 77 | 2.354 | 29.978 | 51.571 | 1.00 11.33 | FKBP |
| ATOM | 752 | OG | SER | 77 | 3.405 | 29.669 | 50.667 | 1.00 18.57 | FKBP |
| ATOM | 753 | HG | SER | 77 | 4.140 | 30.103 | 51.109 | 0.00  0.00 | FKBP |
| ATOM | 754 | C | SER | 77 | 0.681 | 30.566 | 49.790 | 1.00 12.45 | FKBP |
| ATOM | 755 | O | SER | 77 | 0.922 | 30.149 | 48.662 | 1.00 15.48 | FKBP |
| ATOM | 756 | N | PRO | 78 | 0.151 | 31.778 | 49.998 | 1.00 14.32 | FKBP |
| ATOM | 757 | CD | PRO | 78 | 0.192 | 32.544 | 51.251 | 1.00 18.10 | FKBP |
| ATOM | 758 | CA | PRO | 78 | -0.362 | 32.607 | 48.906 | 1.00 14.95 | FKBP |
| ATOM | 759 | CB | PRO | 78 | -0.594 | 33.957 | 49.573 | 1.00 15.74 | FKBP |
| ATOM | 760 | CG | PRO | 78 | 0.309 | 33.944 | 50.759 | 1.00 15.85 | FKBP |
| ATOM | 761 | C | PRO | 78 | 0.574 | 32.728 | 47.710 | 1.00 15.21 | FKBP |
| ATOM | 762 | O | PRO | 78 | 0.109 | 32.790 | 46.576 | 1.00 20.63 | FKBP |
| ATOM | 763 | N | ASP | 79 | 1.882 | 32.698 | 47.956 | 1.00 13.60 | FKBP |
| ATOM | 764 | H | ASP | 79 | 2.162 | 32.697 | 48.889 | 0.00  0.00 | FKBP |
| ATOM | 765 | CA | ASP | 79 | 2.877 | 32.679 | 46.874 | 1.00 19.42 | FKBP |
| ATOM | 766 | CB | ASP | 79 | 4.305 | 32.510 | 47.424 | 1.00 28.97 | FKBP |
| ATOM | 767 | CG | ASP | 79 | 4.599 | 33.401 | 48.629 | 1.00 37.43 | FKBP |
| ATOM | 768 | OD1 | ASP | 79 | 5.657 | 33.195 | 49.270 | 1.00 39.71 | FKBP |
| ATOM | 769 | OD2 | ASP | 79 | 3.792 | 34.306 | 48.939 | 1.00 45.91 | FKBP |
| ATOM | 770 | C | ASP | 79 | 2.616 | 31.548 | 45.877 | 1.00 17.87 | FKBP |
| ATOM | 771 | O | ASP | 79 | 2.547 | 31.777 | 44.676 | 1.00 20.31 | FKBP |
| ATOM | 772 | N | TYR | 80 | 2.442 | 30.335 | 46.392 | 1.00 15.45 | FKBP |
| ATOM | 773 | H | TYR | 80 | 2.347 | 30.254 | 47.356 | 0.00  0.00 | FKBP |
| ATOM | 774 | CA | TYR | 80 | 2.142 | 29.178 | 45.557 | 1.00 12.31 | FKBP |
| ATOM | 775 | CB | TYR | 80 | 2.611 | 27.897 | 46.234 | 1.00 10.17 | FKBP |
| ATOM | 776 | CG | TYR | 80 | 4.082 | 27.626 | 46.070 | 1.00  9.13 | FKBP |
| ATOM | 777 | CD1 | TYR | 80 | 5.022 | 28.600 | 46.373 | 1.00  5.08 | FKBP |
| ATOM | 778 | CE1 | TYR | 80 | 6.373 | 28.303 | 46.419 | 1.00  6.16 | FKBP |
| ATOM | 779 | CD2 | TYR | 80 | 4.536 | 26.347 | 45.781 | 1.00 12.62 | FKBP |
| ATOM | 780 | CE2 | TYR | 80 | 5.889 | 26.037 | 45.827 | 1.00 15.72 | FKBP |
| ATOM | 781 | CZ | TYR | 80 | 6.801 | 27.021 | 46.159 | 1.00 13.97 | FKBP |
| ATOM | 782 | OH | TYR | 80 | 8.124 | 26.683 | 46.343 | 1.00 19.55 | FKBP |
| ATOM | 783 | HH | TYR | 80 | 8.729 | 27.408 | 46.126 | 0.00  0.00 | FKBP |
| ATOM | 784 | C | TYR | 80 | 0.657 | 29.033 | 45.227 | 1.00  9.68 | FKBP |
| ATOM | 785 | O | TYR | 80 | 0.194 | 27.936 | 44.907 | 1.00  9.28 | FKBP |
| ATOM | 786 | N | ALA | 81 | -0.104 | 30.115 | 45.344 | 1.00  9.06 | FKBP |
| ATOM | 787 | H | ALA | 81 | 0.347 | 31.010 | 45.423 | 0.00  0.00 | FKBP |
| ATOM | 788 | CA | ALA | 81 | -1.536 | 30.071 | 45.028 | 1.00  8.94 | FKBP |
| ATOM | 789 | CB | ALA | 81 | -2.362 | 29.899 | 46.312 | 1.00 10.95 | FKBP |
| ATOM | 790 | C | ALA | 81 | -1.973 | 31.342 | 44.290 | 1.00 11.59 | FKBP |
| ATOM | 791 | O | ALA | 81 | -1.507 | 31.630 | 43.192 | 1.00 14.63 | FKBP |
| ATOM | 792 | N | TYR | 82 | -2.886 | 32.106 | 44.874 | 1.00 13.59 | FKBP |
| ATOM | 793 | H | TYR | 82 | -3.142 | 32.049 | 45.838 | 0.00  0.00 | FKBP |
| ATOM | 794 | CA | TYR | 82 | -3.462 | 33.239 | 44.147 | 1.00 15.87 | FKBP |
| ATOM | 795 | CB | TYR | 82 | -4.982 | 33.249 | 44.324 | 1.00 15.49 | FKBP |
| ATOM | 796 | CG | TYR | 82 | -5.676 | 32.084 | 43.658 | 1.00 19.64 | FKBP |
| ATOM | 797 | CD1 | TYR | 82 | -6.283 | 31.091 | 44.415 | 1.00 18.02 | FKBP |
| ATOM | 798 | CE1 | TYR | 82 | -6.918 | 30.013 | 43.804 | 1.00 16.50 | FKBP |
| ATOM | 799 | CD2 | TYR | 82 | -5.724 | 31.975 | 42.262 | 1.00 19.36 | FKBP |
| ATOM | 800 | CE2 | TYR | 82 | -6.357 | 30.904 | 41.648 | 1.00 12.44 | FKBP |

Figure 4: A-17

```
ATOM    801  CZ   TYR    82      -6.946  29.930  42.425  1.00 12.60      FKBP
ATOM    802  OH   TYR    82      -7.546  28.871  41.800  1.00 12.06      FKBP
ATOM    803  HH   TYR    82      -7.818  28.255  42.478  0.00  0.00      FKBP
ATOM    804  C    TYR    82      -2.869  34.591  44.552  1.00 15.70      FKBP
ATOM    805  O    TYR    82      -3.388  35.646  44.183  1.00 15.54      FKBP
ATOM    806  N    GLY    83      -1.763  34.539  45.288  1.00 17.13      FKBP
ATOM    807  H    GLY    83      -1.475  33.662  45.571  0.00  0.00      FKBP
ATOM    808  CA   GLY    83      -0.972  35.719  45.566  1.00 15.64      FKBP
ATOM    809  C    GLY    83      -1.681  36.878  46.233  1.00 20.32      FKBP
ATOM    810  O    GLY    83      -2.708  36.728  46.910  1.00 23.74      FKBP
ATOM    811  N    ALA    84      -1.099  38.055  46.055  1.00 19.06      FKBP
ATOM    812  H    ALA    84      -0.306  38.078  45.480  0.00  0.00      FKBP
ATOM    813  CA   ALA    84      -1.639  39.270  46.628  1.00 15.70      FKBP
ATOM    814  CB   ALA    84      -0.640  40.394  46.455  1.00 19.93      FKBP
ATOM    815  C    ALA    84      -2.965  39.637  45.982  1.00 13.85      FKBP
ATOM    816  O    ALA    84      -3.823  40.230  46.618  1.00 14.46      FKBP
ATOM    817  N    THR    85      -3.131  39.247  44.726  1.00 17.88      FKBP
ATOM    818  H    THR    85      -2.470  38.659  44.303  0.00  0.00      FKBP
ATOM    819  CA   THR    85      -4.308  39.623  43.934  1.00 24.03      FKBP
ATOM    820  CB   THR    85      -4.036  39.482  42.419  1.00 21.29      FKBP
ATOM    821  OG1  THR    85      -3.482  38.185  42.150  1.00 28.80      FKBP
ATOM    822  HG1  THR    85      -4.132  37.483  42.316  0.00  0.00      FKBP
ATOM    823  CG2  THR    85      -3.054  40.541  41.956  1.00 16.23      FKBP
ATOM    824  C    THR    85      -5.537  38.787  44.254  1.00 24.35      FKBP
ATOM    825  O    THR    85      -6.660  39.189  43.954  1.00 27.70      FKBP
ATOM    826  N    GLY    86      -5.304  37.579  44.761  1.00 25.09      FKBP
ATOM    827  H    GLY    86      -4.382  37.292  44.914  0.00  0.00      FKBP
ATOM    828  CA   GLY    86      -6.388  36.655  45.020  1.00 19.79      FKBP
ATOM    829  C    GLY    86      -7.151  36.310  43.759  1.00 21.57      FKBP
ATOM    830  O    GLY    86      -6.589  36.200  42.659  1.00 18.32      FKBP
ATOM    831  N    HIS    87      -8.454  36.149  43.930  1.00 21.72      FKBP
ATOM    832  H    HIS    87      -8.780  36.318  44.827  0.00  0.00      FKBP
ATOM    833  CA   HIS    87      -9.355  35.858  42.828  1.00 24.25      FKBP
ATOM    834  CB   HIS    87      -9.432  34.350  42.568  1.00 25.61      FKBP
ATOM    835  CG   HIS    87     -10.134  33.994  41.292  1.00 29.60      FKBP
ATOM    836  CD2  HIS    87     -11.360  33.466  41.064  1.00 27.65      FKBP
ATOM    837  ND1  HIS    87      -9.564  34.185  40.050  1.00 31.39      FKBP
ATOM    838  HD1  HIS    87      -8.690  34.592  39.843  0.00  0.00      FKBP
ATOM    839  CE1  HIS    87     -10.405  33.783  39.115  1.00 32.76      FKBP
ATOM    840  NE2  HIS    87     -11.503  33.347  39.703  1.00 30.12      FKBP
ATOM    841  HE2  HIS    87     -12.329  33.167  39.202  0.00  0.00      FKBP
ATOM    842  C    HIS    87     -10.727  36.387  43.212  1.00 22.13      FKBP
ATOM    843  O    HIS    87     -11.356  35.891  44.152  1.00 27.18      FKBP
ATOM    844  N    PRO    88     -11.105  37.531  42.639  1.00 19.63      FKBP
ATOM    845  CD   PRO    88     -10.357  38.290  41.620  1.00 20.36      FKBP
ATOM    846  CA   PRO    88     -11.989  38.403  43.410  1.00 18.79      FKBP
ATOM    847  CB   PRO    88     -11.946  39.707  42.626  1.00 18.51      FKBP
ATOM    848  CG   PRO    88     -10.550  39.713  42.059  1.00 16.30      FKBP
ATOM    849  C    PRO    88     -13.399  37.848  43.580  1.00 18.22      FKBP
ATOM    850  O    PRO    88     -13.974  37.286  42.650  1.00 21.77      FKBP
```

Figure 4: A-18

| | | | | | | | | | | |
|---|---|---|---|---|---|---|---|---|---|---|
| ATOM | 851 | N | GLY | 89 | -13.851 | 37.819 | 44.828 | 1.00 | 15.16 | FKBP |
| ATOM | 852 | H | GLY | 89 | -13.303 | 38.201 | 45.539 | 0.00 | 0.00 | FKBP |
| ATOM | 853 | CA | GLY | 89 | -15.160 | 37.271 | 45.120 | 1.00 | 12.28 | FKBP |
| ATOM | 854 | C | GLY | 89 | -15.116 | 35.891 | 45.749 | 1.00 | 13.88 | FKBP |
| ATOM | 855 | O | GLY | 89 | -16.142 | 35.385 | 46.211 | 1.00 | 13.05 | FKBP |
| ATOM | 856 | N | ILE | 90 | -13.932 | 35.289 | 45.812 | 1.00 | 12.11 | FKBP |
| ATOM | 857 | H | ILE | 90 | -13.164 | 35.742 | 45.410 | 0.00 | 0.00 | FKBP |
| ATOM | 858 | CA | ILE | 90 | -13.831 | 33.928 | 46.328 | 1.00 | 17.75 | FKBP |
| ATOM | 859 | CB | ILE | 90 | -13.950 | 32.875 | 45.177 | 1.00 | 23.54 | FKBP |
| ATOM | 860 | CG2 | ILE | 90 | -13.063 | 33.252 | 44.007 | 1.00 | 24.28 | FKBP |
| ATOM | 861 | CG1 | ILE | 90 | -13.590 | 31.478 | 45.688 | 1.00 | 28.28 | FKBP |
| ATOM | 862 | CD1 | ILE | 90 | -14.036 | 30.361 | 44.764 | 1.00 | 34.25 | FKBP |
| ATOM | 863 | C | ILE | 90 | -12.577 | 33.670 | 47.150 | 1.00 | 14.47 | FKBP |
| ATOM | 864 | O | ILE | 90 | -12.663 | 33.134 | 48.247 | 1.00 | 15.69 | FKBP |
| ATOM | 865 | N | ILE | 91 | -11.416 | 34.013 | 46.600 | 1.00 | 12.99 | FKBP |
| ATOM | 866 | H | ILE | 91 | -11.413 | 34.380 | 45.696 | 0.00 | 0.00 | FKBP |
| ATOM | 867 | CA | ILE | 91 | -10.150 | 33.915 | 47.328 | 1.00 | 9.92 | FKBP |
| ATOM | 868 | CB | ILE | 91 | -9.091 | 33.085 | 46.559 | 1.00 | 6.38 | FKBP |
| ATOM | 869 | CG2 | ILE | 91 | -7.873 | 32.881 | 47.428 | 1.00 | 2.00 | FKBP |
| ATOM | 870 | CG1 | ILE | 91 | -9.681 | 31.762 | 46.041 | 1.00 | 4.55 | FKBP |
| ATOM | 871 | CD1 | ILE | 91 | -10.163 | 30.821 | 47.084 | 1.00 | 3.68 | FKBP |
| ATOM | 872 | C | ILE | 91 | -9.584 | 35.324 | 47.520 | 1.00 | 15.34 | FKBP |
| ATOM | 873 | O | ILE | 91 | -9.285 | 36.025 | 46.539 | 1.00 | 13.98 | FKBP |
| ATOM | 874 | N | PRO | 92 | -9.520 | 35.797 | 48.781 | 1.00 | 17.29 | FKBP |
| ATOM | 875 | CD | PRO | 92 | -9.964 | 35.110 | 50.011 | 1.00 | 14.17 | FKBP |
| ATOM | 876 | CA | PRO | 92 | -9.007 | 37.143 | 49.062 | 1.00 | 12.40 | FKBP |
| ATOM | 877 | CB | PRO | 92 | -9.421 | 37.381 | 50.514 | 1.00 | 10.67 | FKBP |
| ATOM | 878 | CG | PRO | 92 | -9.477 | 36.019 | 51.107 | 1.00 | 11.96 | FKBP |
| ATOM | 879 | C | PRO | 92 | -7.492 | 37.264 | 48.855 | 1.00 | 14.30 | FKBP |
| ATOM | 880 | O | PRO | 92 | -6.815 | 36.290 | 48.516 | 1.00 | 17.48 | FKBP |
| ATOM | 881 | N | PRO | 93 | -6.966 | 38.493 | 48.923 | 1.00 | 15.65 | FKBP |
| ATOM | 882 | CD | PRO | 93 | -7.700 | 39.762 | 48.785 | 1.00 | 18.15 | FKBP |
| ATOM | 883 | CA | PRO | 93 | -5.518 | 38.704 | 48.833 | 1.00 | 16.50 | FKBP |
| ATOM | 884 | CB | PRO | 93 | -5.380 | 40.217 | 48.941 | 1.00 | 17.10 | FKBP |
| ATOM | 885 | CG | PRO | 93 | -6.629 | 40.717 | 48.308 | 1.00 | 22.16 | FKBP |
| ATOM | 886 | C | PRO | 93 | -4.743 | 37.999 | 49.933 | 1.00 | 16.97 | FKBP |
| ATOM | 887 | O | PRO | 93 | -5.160 | 37.971 | 51.090 | 1.00 | 20.11 | FKBP |
| ATOM | 888 | N | HIS | 94 | -3.609 | 37.424 | 49.563 | 1.00 | 15.46 | FKBP |
| ATOM | 889 | H | HIS | 94 | -3.476 | 37.286 | 48.598 | 0.00 | 0.00 | FKBP |
| ATOM | 890 | CA | HIS | 94 | -2.701 | 36.830 | 50.538 | 1.00 | 14.40 | FKBP |
| ATOM | 891 | CB | HIS | 94 | -2.366 | 37.855 | 51.608 | 1.00 | 12.10 | FKBP |
| ATOM | 892 | CG | HIS | 94 | -1.762 | 39.103 | 51.061 | 1.00 | 15.95 | FKBP |
| ATOM | 893 | CD2 | HIS | 94 | -2.313 | 40.308 | 50.781 | 1.00 | 16.10 | FKBP |
| ATOM | 894 | ND1 | HIS | 94 | -0.455 | 39.165 | 50.621 | 1.00 | 16.58 | FKBP |
| ATOM | 895 | HD1 | HIS | 94 | 0.241 | 38.484 | 50.761 | 0.00 | 0.00 | FKBP |
| ATOM | 896 | CE1 | HIS | 94 | -0.230 | 40.351 | 50.086 | 1.00 | 20.16 | FKBP |
| ATOM | 897 | NE2 | HIS | 94 | -1.342 | 41.063 | 50.171 | 1.00 | 21.63 | FKBP |
| ATOM | 898 | HE2 | HIS | 94 | -1.470 | 41.979 | 49.833 | 0.00 | 0.00 | FKBP |
| ATOM | 899 | C | HIS | 94 | -3.176 | 35.531 | 51.202 | 1.00 | 13.30 | FKBP |
| ATOM | 900 | O | HIS | 94 | -2.380 | 34.843 | 51.836 | 1.00 | 16.61 | FKBP |

Figure 4: A-19

| | | | | | | | | | | |
|---|---|---|---|---|---|---|---|---|---|---|
| ATOM | 901 | N   | ALA | 95  | -4.403 | 35.112 | 50.915 | 1.00 | 6.56  | FKBP |
| ATOM | 902 | H   | ALA | 95  | -4.911 | 35.568 | 50.215 | 0.00 | 0.00  | FKBP |
| ATOM | 903 | CA  | ALA | 95  | -4.982 | 33.954 | 51.576 | 1.00 | 7.81  | FKBP |
| ATOM | 904 | CB  | ALA | 95  | -6.365 | 33.676 | 51.026 | 1.00 | 2.72  | FKBP |
| ATOM | 905 | C   | ALA | 95  | -4.132 | 32.683 | 51.516 | 1.00 | 10.01 | FKBP |
| ATOM | 906 | O   | ALA | 95  | -3.691 | 32.260 | 50.456 | 1.00 | 10.42 | FKBP |
| ATOM | 907 | N   | THR | 96  | -3.801 | 32.165 | 52.691 | 1.00 | 12.98 | FKBP |
| ATOM | 908 | H   | THR | 96  | -3.847 | 32.758 | 53.468 | 0.00 | 0.00  | FKBP |
| ATOM | 909 | CA  | THR | 96  | -3.319 | 30.797 | 52.831 | 1.00 | 12.92 | FKBP |
| ATOM | 910 | CB  | THR | 96  | -2.740 | 30.568 | 54.254 | 1.00 | 9.93  | FKBP |
| ATOM | 911 | OG1 | THR | 96  | -1.655 | 31.480 | 54.472 | 1.00 | 11.98 | FKBP |
| ATOM | 912 | HG1 | THR | 96  | -1.236 | 31.644 | 53.620 | 0.00 | 0.00  | FKBP |
| ATOM | 913 | CG2 | THR | 96  | -2.240 | 29.139 | 54.430 | 1.00 | 3.68  | FKBP |
| ATOM | 914 | C   | THR | 96  | -4.501 | 29.852 | 52.600 | 1.00 | 14.35 | FKBP |
| ATOM | 915 | O   | THR | 96  | -5.569 | 30.025 | 53.212 | 1.00 | 14.86 | FKBP |
| ATOM | 916 | N   | LEU | 97  | -4.349 | 28.937 | 51.642 | 1.00 | 8.43  | FKBP |
| ATOM | 917 | H   | LEU | 97  | -3.495 | 28.902 | 51.157 | 0.00 | 0.00  | FKBP |
| ATOM | 918 | CA  | LEU | 97  | -5.406 | 27.976 | 51.332 | 1.00 | 3.80  | FKBP |
| ATOM | 919 | CB  | LEU | 97  | -5.672 | 27.930 | 49.826 | 1.00 | 3.61  | FKBP |
| ATOM | 920 | CG  | LEU | 97  | -5.948 | 29.193 | 49.011 | 1.00 | 6.56  | FKBP |
| ATOM | 921 | CD1 | LEU | 97  | -5.831 | 28.841 | 47.534 | 1.00 | 2.62  | FKBP |
| ATOM | 922 | CD2 | LEU | 97  | -7.326 | 29.758 | 49.318 | 1.00 | 6.52  | FKBP |
| ATOM | 923 | C   | LEU | 97  | -5.083 | 26.557 | 51.814 | 1.00 | 5.71  | FKBP |
| ATOM | 924 | O   | LEU | 97  | -3.926 | 26.123 | 51.815 | 1.00 | 7.74  | FKBP |
| ATOM | 925 | N   | VAL | 98  | -6.121 | 25.814 | 52.167 | 1.00 | 2.33  | FKBP |
| ATOM | 926 | H   | VAL | 98  | -7.012 | 26.221 | 52.183 | 0.00 | 0.00  | FKBP |
| ATOM | 927 | CA  | VAL | 98  | -5.968 | 24.407 | 52.476 | 1.00 | 3.09  | FKBP |
| ATOM | 928 | CB  | VAL | 98  | -6.461 | 24.079 | 53.900 | 1.00 | 4.96  | FKBP |
| ATOM | 929 | CG1 | VAL | 98  | -6.144 | 22.638 | 54.230 | 1.00 | 2.00  | FKBP |
| ATOM | 930 | CG2 | VAL | 98  | -5.824 | 25.011 | 54.917 | 1.00 | 2.00  | FKBP |
| ATOM | 931 | C   | VAL | 98  | -6.801 | 23.602 | 51.491 | 1.00 | 7.78  | FKBP |
| ATOM | 932 | O   | VAL | 98  | -8.012 | 23.836 | 51.346 | 1.00 | 8.13  | FKBP |
| ATOM | 933 | N   | PHE | 99  | -6.166 | 22.622 | 50.853 | 1.00 | 7.58  | FKBP |
| ATOM | 934 | H   | PHE | 99  | -5.202 | 22.540 | 50.970 | 0.00 | 0.00  | FKBP |
| ATOM | 935 | CA  | PHE | 99  | -6.877 | 21.677 | 49.996 | 1.00 | 6.62  | FKBP |
| ATOM | 936 | CB  | PHE | 99  | -6.303 | 21.728 | 48.578 | 1.00 | 2.00  | FKBP |
| ATOM | 937 | CG  | PHE | 99  | -6.824 | 22.873 | 47.763 | 1.00 | 4.66  | FKBP |
| ATOM | 938 | CD1 | PHE | 99  | -6.115 | 24.070 | 47.687 | 1.00 | 4.09  | FKBP |
| ATOM | 939 | CD2 | PHE | 99  | -8.069 | 22.787 | 47.138 | 1.00 | 2.68  | FKBP |
| ATOM | 940 | CE1 | PHE | 99  | -6.638 | 25.166 | 47.008 | 1.00 | 2.00  | FKBP |
| ATOM | 941 | CE2 | PHE | 99  | -8.598 | 23.874 | 46.462 | 1.00 | 2.00  | FKBP |
| ATOM | 942 | CZ  | PHE | 99  | -7.879 | 25.068 | 46.399 | 1.00 | 2.00  | FKBP |
| ATOM | 943 | C   | PHE | 99  | -6.849 | 20.239 | 50.519 | 1.00 | 5.20  | FKBP |
| ATOM | 944 | O   | PHE | 99  | -5.796 | 19.718 | 50.860 | 1.00 | 5.24  | FKBP |
| ATOM | 945 | N   | ASP | 100 | -8.014 | 19.613 | 50.627 | 1.00 | 3.90  | FKBP |
| ATOM | 946 | H   | ASP | 100 | -8.834 | 20.147 | 50.593 | 0.00 | 0.00  | FKBP |
| ATOM | 947 | CA  | ASP | 100 | -8.070 | 18.167 | 50.830 | 1.00 | 7.59  | FKBP |
| ATOM | 948 | CB  | ASP | 100 | -9.205 | 17.817 | 51.804 | 1.00 | 6.95  | FKBP |
| ATOM | 949 | CG  | ASP | 100 | -9.424 | 16.310 | 51.966 | 1.00 | 7.89  | FKBP |
| ATOM | 950 | OD1 | ASP | 100 | -8.564 | 15.494 | 51.568 | 1.00 | 14.35 | FKBP |

Figure 4: A-20

| ATOM | 951 | OD2 | ASP | 100 | -10.480 | 15.937 | 52.511 | 1.00 | 12.55 | FKBP |
|------|-----|-----|-----|-----|---------|--------|--------|------|-------|------|
| ATOM | 952 | C | ASP | 100 | -8.280 | 17.463 | 49.482 | 1.00 | 9.31 | FKBP |
| ATOM | 953 | O | ASP | 100 | -9.379 | 17.490 | 48.934 | 1.00 | 10.21 | FKBP |
| ATOM | 954 | N | VAL | 101 | -7.232 | 16.832 | 48.954 | 1.00 | 9.09 | FKBP |
| ATOM | 955 | H | VAL | 101 | -6.416 | 16.741 | 49.499 | 0.00 | 0.00 | FKBP |
| ATOM | 956 | CA | VAL | 101 | -7.306 | 16.202 | 47.633 | 1.00 | 11.24 | FKBP |
| ATOM | 957 | CB | VAL | 101 | -6.417 | 16.956 | 46.557 | 1.00 | 7.24 | FKBP |
| ATOM | 958 | CG1 | VAL | 101 | -6.122 | 18.380 | 47.014 | 1.00 | 5.62 | FKBP |
| ATOM | 959 | CG2 | VAL | 101 | -5.118 | 16.208 | 46.278 | 1.00 | 3.42 | FKBP |
| ATOM | 960 | C | VAL | 101 | -6.957 | 14.711 | 47.652 | 1.00 | 12.17 | FKBP |
| ATOM | 961 | O | VAL | 101 | -5.962 | 14.296 | 48.251 | 1.00 | 12.83 | FKBP |
| ATOM | 962 | N | GLU | 102 | -7.796 | 13.913 | 47.001 | 1.00 | 11.69 | FKBP |
| ATOM | 963 | H | GLU | 102 | -8.591 | 14.307 | 46.611 | 0.00 | 0.00 | FKBP |
| ATOM | 964 | CA | GLU | 102 | -7.527 | 12.490 | 46.813 | 1.00 | 14.51 | FKBP |
| ATOM | 965 | CB | GLU | 102 | -8.697 | 11.660 | 47.356 | 1.00 | 12.86 | FKBP |
| ATOM | 966 | CG | GLU | 102 | -8.562 | 10.171 | 47.074 | 1.00 | 18.32 | FKBP |
| ATOM | 967 | CD | GLU | 102 | -9.681 | 9.340 | 47.666 | 1.00 | 20.79 | FKBP |
| ATOM | 968 | OE1 | GLU | 102 | -10.840 | 9.811 | 47.715 | 1.00 | 26.66 | FKBP |
| ATOM | 969 | OE2 | GLU | 102 | -9.402 | 8.187 | 48.052 | 1.00 | 23.60 | FKBP |
| ATOM | 970 | C | GLU | 102 | -7.266 | 12.132 | 45.336 | 1.00 | 13.17 | FKBP |
| ATOM | 971 | O | GLU | 102 | -8.100 | 12.392 | 44.465 | 1.00 | 15.41 | FKBP |
| ATOM | 972 | N | LEU | 103 | -6.147 | 11.465 | 45.079 | 1.00 | 9.34 | FKBP |
| ATOM | 973 | H | LEU | 103 | -5.600 | 11.178 | 45.846 | 0.00 | 0.00 | FKBP |
| ATOM | 974 | CA | LEU | 103 | -5.763 | 11.096 | 43.722 | 1.00 | 13.72 | FKBP |
| ATOM | 975 | CB | LEU | 103 | -4.226 | 11.024 | 43.593 | 1.00 | 6.09 | FKBP |
| ATOM | 976 | CG | LEU | 103 | -3.643 | 10.842 | 42.180 | 1.00 | 4.19 | FKBP |
| ATOM | 977 | CD1 | LEU | 103 | -4.309 | 11.807 | 41.220 | 1.00 | 8.95 | FKBP |
| ATOM | 978 | CD2 | LEU | 103 | -2.149 | 11.088 | 42.180 | 1.00 | 3.73 | FKBP |
| ATOM | 979 | C | LEU | 103 | -6.404 | 9.767 | 43.302 | 1.00 | 15.75 | FKBP |
| ATOM | 980 | O | LEU | 103 | -5.838 | 8.698 | 43.511 | 1.00 | 16.07 | FKBP |
| ATOM | 981 | N | LEU | 104 | -7.579 | 9.856 | 42.685 | 1.00 | 18.31 | FKBP |
| ATOM | 982 | H | LEU | 104 | -7.915 | 10.758 | 42.502 | 0.00 | 0.00 | FKBP |
| ATOM | 983 | CA | LEU | 104 | -8.342 | 8.680 | 42.257 | 1.00 | 16.33 | FKBP |
| ATOM | 984 | CB | LEU | 104 | -9.664 | 9.120 | 41.633 | 1.00 | 14.17 | FKBP |
| ATOM | 985 | CG | LEU | 104 | -10.547 | 10.017 | 42.500 | 1.00 | 14.18 | FKBP |
| ATOM | 986 | CD1 | LEU | 104 | -11.838 | 10.345 | 41.772 | 1.00 | 13.42 | FKBP |
| ATOM | 987 | CD2 | LEU | 104 | -10.843 | 9.307 | 43.804 | 1.00 | 14.17 | FKBP |
| ATOM | 988 | C | LEU | 104 | -7.594 | 7.786 | 41.266 | 1.00 | 18.03 | FKBP |
| ATOM | 989 | O | LEU | 104 | -7.390 | 6.599 | 41.516 | 1.00 | 18.22 | FKBP |
| ATOM | 990 | N | LYS | 105 | -7.196 | 8.360 | 40.134 | 1.00 | 20.74 | FKBP |
| ATOM | 991 | H | LYS | 105 | -7.343 | 9.323 | 40.023 | 0.00 | 0.00 | FKBP |
| ATOM | 992 | CA | LYS | 105 | -6.510 | 7.603 | 39.086 | 1.00 | 20.67 | FKBP |
| ATOM | 993 | CB | LYS | 105 | -7.529 | 6.806 | 38.263 | 1.00 | 24.07 | FKBP |
| ATOM | 994 | CG | LYS | 105 | -8.765 | 7.605 | 37.853 | 1.00 | 27.58 | FKBP |
| ATOM | 995 | CD | LYS | 105 | -9.733 | 6.771 | 37.027 | 1.00 | 30.34 | FKBP |
| ATOM | 996 | CE | LYS | 105 | -10.994 | 7.557 | 36.684 | 1.00 | 34.49 | FKBP |
| ATOM | 997 | NZ | LYS | 105 | -11.853 | 7.826 | 37.876 | 1.00 | 35.90 | FKBP |
| ATOM | 998 | HZ1 | LYS | 105 | -11.317 | 8.378 | 38.576 | 0.00 | 0.00 | FKBP |
| ATOM | 999 | HZ2 | LYS | 105 | -12.151 | 6.928 | 38.306 | 0.00 | 0.00 | FKBP |
| ATOM | 1000 | HZ3 | LYS | 105 | -12.690 | 8.371 | 37.584 | 0.00 | 0.00 | FKBP |

Figure 4: A-21

| | | | | | | | | | |
|---|---|---|---|---|---|---|---|---|---|
| ATOM | 1001 | C | LYS | 105 | -5.692 | 8.497 | 38.154 | 1.00 19.89 | FKBP |
| ATOM | 1002 | O | LYS | 105 | -5.948 | 9.696 | 38.038 | 1.00 21.43 | FKBP |
| ATOM | 1003 | N | LEU | 106 | -4.664 | 7.927 | 37.545 | 1.00 22.51 | FKBP |
| ATOM | 1004 | H | LEU | 106 | -4.392 | 7.031 | 37.820 | 0.00 0.00 | FKBP |
| ATOM | 1005 | CA | LEU | 106 | -4.015 | 8.575 | 36.411 | 1.00 24.63 | FKBP |
| ATOM | 1006 | CB | LEU | 106 | -2.500 | 8.385 | 36.469 | 1.00 20.64 | FKBP |
| ATOM | 1007 | CG | LEU | 106 | -1.709 | 9.334 | 37.369 | 1.00 25.07 | FKBP |
| ATOM | 1008 | CD1 | LEU | 106 | -2.201 | 10.771 | 37.213 | 1.00 26.33 | FKBP |
| ATOM | 1009 | CD2 | LEU | 106 | -1.853 | 8.891 | 38.791 | 1.00 25.85 | FKBP |
| ATOM | 1010 | C | LEU | 106 | -4.544 | 8.044 | 35.076 | 1.00 27.28 | FKBP |
| ATOM | 1011 | O | LEU | 106 | -4.969 | 6.887 | 34.978 | 1.00 30.28 | FKBP |
| ATOM | 1012 | N | GLU | 107 | -4.660 | 8.946 | 34.108 | 1.00 28.70 | FKBP |
| ATOM | 1013 | H | GLU | 107 | -4.585 | 9.896 | 34.325 | 0.00 0.00 | FKBP |
| ATOM | 1014 | CA | GLU | 107 | -4.910 | 8.585 | 32.718 | 1.00 28.85 | FKBP |
| ATOM | 1015 | CB | GLU | 107 | -6.410 | 8.650 | 32.415 | 1.00 24.83 | FKBP |
| ATOM | 1016 | CG | GLU | 107 | -7.125 | 9.812 | 33.068 | 1.00 28.14 | FKBP |
| ATOM | 1017 | CD | GLU | 107 | -8.428 | 10.140 | 32.379 | 1.00 33.36 | FKBP |
| ATOM | 1018 | OE1 | GLU | 107 | -9.439 | 9.461 | 32.672 | 1.00 26.99 | FKBP |
| ATOM | 1019 | OE2 | GLU | 107 | -8.433 | 11.070 | 31.534 | 1.00 36.01 | FKBP |
| ATOM | 1020 | C | GLU | 107 | -4.122 | 9.520 | 31.789 | 1.00 32.85 | FKBP |
| ATOM | 1021 | O | GLU | 107 | -2.875 | 9.520 | 31.888 | 1.00 37.58 | FKBP |
| ATOM | 1022 | OT | GLU | 107 | -4.739 | 10.301 | 31.034 | 1.00 39.52 | FKBP |
| ATOM | 1023 | O1 | RAPX | 108 | -7.715 | 26.739 | 39.504 | 1.00 6.16 | RAPX |
| ATOM | 1024 | C1 | RAPX | 108 | -6.816 | 26.014 | 40.365 | 1.00 5.94 | RAPX |
| ATOM | 1025 | O2 | RAPX | 108 | -5.659 | 25.863 | 39.953 | 1.00 4.69 | RAPX |
| ATOM | 1026 | C2 | RAPX | 108 | -7.234 | 25.472 | 41.742 | 1.00 2.10 | RAPX |
| ATOM | 1027 | C3 | RAPX | 108 | -6.748 | 24.038 | 41.963 | 1.00 2.00 | RAPX |
| ATOM | 1028 | C4 | RAPX | 108 | -7.531 | 22.968 | 41.204 | 1.00 2.86 | RAPX |
| ATOM | 1029 | C5 | RAPX | 108 | -9.027 | 23.085 | 41.430 | 1.00 2.00 | RAPX |
| ATOM | 1030 | C6 | RAPX | 108 | -9.492 | 24.485 | 41.139 | 1.00 2.08 | RAPX |
| ATOM | 1031 | N7 | RAPX | 108 | -8.685 | 25.389 | 41.985 | 1.00 3.45 | RAPX |
| ATOM | 1032 | C8 | RAPX | 108 | -9.287 | 26.223 | 42.852 | 1.00 2.80 | RAPX |
| ATOM | 1033 | O3 | RAPX | 108 | -8.653 | 27.066 | 43.484 | 1.00 4.16 | RAPX |
| ATOM | 1034 | C9 | RAPX | 108 | -10.645 | 26.309 | 43.120 | 1.00 3.33 | RAPX |
| ATOM | 1035 | O4 | RAPX | 108 | -11.026 | 25.607 | 44.055 | 1.00 2.89 | RAPX |
| ATOM | 1036 | C10 | RAPX | 108 | -11.647 | 27.189 | 42.361 | 1.00 7.35 | RAPX |
| ATOM | 1037 | C11 | RAPX | 108 | -11.102 | 28.623 | 42.177 | 1.00 5.50 | RAPX |
| ATOM | 1038 | C12 | RAPX | 108 | -12.102 | 29.453 | 41.362 | 1.00 2.25 | RAPX |
| ATOM | 1039 | C13 | RAPX | 108 | -12.661 | 28.755 | 40.117 | 1.00 3.81 | RAPX |
| ATOM | 1040 | C14 | RAPX | 108 | -12.744 | 27.225 | 40.197 | 1.00 5.55 | RAPX |
| ATOM | 1041 | O5 | RAPX | 108 | -11.749 | 26.675 | 41.029 | 1.00 5.80 | RAPX |
| ATOM | 1042 | O6 | RAPX | 108 | -12.815 | 27.195 | 43.206 | 1.00 7.04 | RAPX |
| ATOM | 1043 | C43 | RAPX | 108 | -10.856 | 29.287 | 43.527 | 1.00 10.83 | RAPX |
| ATOM | 1044 | C15 | RAPX | 108 | -12.476 | 26.558 | 38.844 | 1.00 6.36 | RAPX |
| ATOM | 1045 | C16 | RAPX | 108 | -13.491 | 26.688 | 37.700 | 1.00 7.22 | RAPX |
| ATOM | 1046 | O7 | RAPX | 108 | -14.764 | 26.288 | 38.070 | 1.00 6.77 | RAPX |
| ATOM | 1047 | C50 | RAPX | 108 | -15.819 | 26.946 | 37.457 | 1.00 2.69 | RAPX |
| ATOM | 1048 | C17 | RAPX | 108 | -13.020 | 25.794 | 36.553 | 1.00 7.17 | RAPX |
| ATOM | 1049 | C44 | RAPX | 108 | -12.882 | 24.304 | 36.817 | 1.00 5.39 | RAPX |
| ATOM | 1050 | C18 | RAPX | 108 | -12.702 | 26.344 | 35.400 | 1.00 12.19 | RAPX |

Figure 4: A-22

```
ATOM   1051  C19  RAPX  108   -12.183  25.694  34.165  1.00  14.38      RAPX
ATOM   1052  C20  RAPX  108   -12.264  26.351  33.003  1.00  13.32      RAPX
ATOM   1053  C21  RAPX  108   -11.719  25.829  31.760  1.00  10.57      RAPX
ATOM   1054  C22  RAPX  108   -10.967  26.472  30.890  1.00   7.17      RAPX
ATOM   1055  C23  RAPX  108   -10.527  25.696  29.671  1.00   3.85      RAPX
ATOM   1056  C45  RAPX  108   -11.166  26.303  28.459  1.00   2.00      RAPX
ATOM   1057  C24  RAPX  108    -9.009  25.760  29.546  1.00   5.00      RAPX
ATOM   1058  C25  RAPX  108    -8.217  25.354  30.783  1.00   6.28      RAPX
ATOM   1059  C46  RAPX  108    -8.066  23.836  30.825  1.00   4.71      RAPX
ATOM   1060  C26  RAPX  108    -6.853  26.023  30.751  1.00   9.09      RAPX
ATOM   1061  O8   RAPX  108    -5.913  25.475  30.185  1.00  17.77      RAPX
ATOM   1062  C27  RAPX  108    -6.684  27.414  31.356  1.00  14.08      RAPX
ATOM   1063  O9   RAPX  108    -5.514  27.884  30.789  1.00  14.20      RAPX
ATOM   1064  C51  RAPX  108    -5.711  28.919  29.903  1.00  21.98      RAPX
ATOM   1065  C28  RAPX  108    -6.426  27.335  32.858  1.00  13.28      RAPX
ATOM   1066  O10  RAPX  108    -5.394  26.369  33.097  1.00  17.10      RAPX
ATOM   1067  C29  RAPX  108    -7.657  26.973  33.703  1.00   7.79      RAPX
ATOM   1068  C47  RAPX  108    -8.663  28.083  33.806  1.00   2.00      RAPX
ATOM   1069  C30  RAPX  108    -7.814  25.804  34.281  1.00   5.36      RAPX
ATOM   1070  C31  RAPX  108    -8.914  25.353  35.171  1.00   5.26      RAPX
ATOM   1071  C48  RAPX  108    -9.109  23.870  34.864  1.00   3.40      RAPX
ATOM   1072  C32  RAPX  108    -8.560  25.557  36.644  1.00   8.61      RAPX
ATOM   1073  O11  RAPX  108    -8.235  24.591  37.334  1.00  12.38      RAPX
ATOM   1074  C33  RAPX  108    -8.639  26.961  37.262  1.00   6.28      RAPX
ATOM   1075  C34  RAPX  108    -7.455  27.273  38.205  1.00   7.20      RAPX
ATOM   1076  C35  RAPX  108    -7.353  28.808  38.512  1.00   4.56      RAPX
ATOM   1077  C49  RAPX  108    -8.736  29.425  38.657  1.00   2.00      RAPX
ATOM   1078  C36  RAPX  108    -6.618  29.542  37.393  1.00   6.95      RAPX
ATOM   1079  C37  RAPX  108    -5.242  29.057  36.926  1.00  11.47      RAPX
ATOM   1080  C38  RAPX  108    -4.839  29.836  35.667  1.00   9.55      RAPX
ATOM   1081  C39  RAPX  108    -3.488  29.508  35.015  1.00  14.00      RAPX
ATOM   1082  O12  RAPX  108    -3.117  30.527  34.126  1.00  21.91      RAPX
ATOM   1083  C52  RAPX  108    -4.002  31.014  33.140  1.00  21.11      RAPX
ATOM   1084  C40  RAPX  108    -2.354  29.491  36.072  1.00  15.37      RAPX
ATOM   1085  O13  RAPX  108    -1.167  28.920  35.507  1.00   6.26      RAPX
ATOM   1086  C41  RAPX  108    -2.766  28.682  37.309  1.00  13.80      RAPX
ATOM   1087  C42  RAPX  108    -4.078  29.130  37.914  1.00   9.01      RAPX
ATOM   1088  H6   RAPX  108   -12.593  27.124  44.143  0.00   0.00      RAPX
ATOM   1089  H10  RAPX  108    -4.969  26.537  33.948  0.00   0.00      RAPX
ATOM   1090  H13  RAPX  108    -0.427  29.516  35.649  0.00   0.00      RAPX
ATOM   1091  CB   ARG   2018  -17.032  35.522   6.831  1.00  40.78      FRAP
ATOM   1092  CG   ARG   2018  -18.205  36.058   7.690  1.00  39.26      FRAP
ATOM   1093  CD   ARG   2018  -18.451  35.201   8.947  1.00  39.90      FRAP
ATOM   1094  NE   ARG   2018  -17.238  35.062   9.755  1.00  40.36      FRAP
ATOM   1095  HE   ARG   2018  -16.986  35.810  10.336  0.00   0.00      FRAP
ATOM   1096  CZ   ARG   2018  -16.466  33.977   9.783  1.00  36.06      FRAP
ATOM   1097  NH1  ARG   2018  -15.238  34.057  10.282  1.00  33.73      FRAP
ATOM   1098  HH11 ARG   2018  -14.887  34.922  10.634  0.00   0.00      FRAP
ATOM   1099  HH12 ARG   2018  -14.676  33.233  10.320  0.00   0.00      FRAP
ATOM   1100  NH2  ARG   2018  -16.931  32.806   9.364  1.00  32.42      FRAP
```

Figure 4: A-23

```
ATOM   1101  HH21 ARG  2018    -17.868  32.729   9.020  0.00   0.00      FRAP
ATOM   1102  HH22 ARG  2018    -16.342  31.999   9.380  0.00   0.00      FRAP
ATOM   1103  C    ARG  2018    -14.580  34.887   6.780  1.00  38.22      FRAP
ATOM   1104  O    ARG  2018    -13.857  35.228   5.840  1.00  36.64      FRAP
ATOM   1105  HT1  ARG  2018    -15.235  37.392   6.027  0.00   0.00      FRAP
ATOM   1106  HT2  ARG  2018    -14.365  37.551   7.457  0.00   0.00      FRAP
ATOM   1107  N    ARG  2018    -15.291  37.286   7.064  1.00  42.10      FRAP
ATOM   1108  HT3  ARG  2018    -16.030  37.925   7.426  0.00   0.00      FRAP
ATOM   1109  CA   ARG  2018    -15.622  35.859   7.359  1.00  39.30      FRAP
ATOM   1110  N    VAL  2019    -14.474  33.705   7.388  1.00  36.94      FRAP
ATOM   1111  H    VAL  2019    -15.146  33.399   8.027  0.00   0.00      FRAP
ATOM   1112  CA   VAL  2019    -13.432  32.725   7.052  1.00  30.21      FRAP
ATOM   1113  CB   VAL  2019    -12.157  32.939   7.942  1.00  32.18      FRAP
ATOM   1114  CG1  VAL  2019    -12.536  32.966   9.417  1.00  26.50      FRAP
ATOM   1115  CG2  VAL  2019    -11.107  31.853   7.679  1.00  32.10      FRAP
ATOM   1116  C    VAL  2019    -13.973  31.314   7.273  1.00  24.65      FRAP
ATOM   1117  O    VAL  2019    -14.934  31.123   8.016  1.00  24.40      FRAP
ATOM   1118  N    ALA  2020    -13.355  30.329   6.635  1.00  22.00      FRAP
ATOM   1119  H    ALA  2020    -12.627  30.546   6.016  0.00   0.00      FRAP
ATOM   1120  CA   ALA  2020    -13.693  28.930   6.883  1.00  22.59      FRAP
ATOM   1121  CB   ALA  2020    -13.356  28.087   5.664  1.00  21.75      FRAP
ATOM   1122  C    ALA  2020    -13.000  28.354   8.125  1.00  22.82      FRAP
ATOM   1123  O    ALA  2020    -11.764  28.295   8.199  1.00  19.38      FRAP
ATOM   1124  N    ILE  2021    -13.805  27.988   9.118  1.00  20.69      FRAP
ATOM   1125  H    ILE  2021    -14.741  28.270   9.101  0.00   0.00      FRAP
ATOM   1126  CA   ILE  2021    -13.312  27.233  10.266  1.00  18.46      FRAP
ATOM   1127  CB   ILE  2021    -12.730  28.173  11.358  1.00  22.76      FRAP
ATOM   1128  CG2  ILE  2021    -13.769  29.208  11.775  1.00  25.54      FRAP
ATOM   1129  CG1  ILE  2021    -12.249  27.351  12.562  1.00  25.06      FRAP
ATOM   1130  CD1  ILE  2021    -11.140  28.005  13.366  1.00  25.45      FRAP
ATOM   1131  C    ILE  2021    -14.413  26.367  10.876  1.00  15.19      FRAP
ATOM   1132  O    ILE  2021    -15.580  26.750  10.885  1.00  15.20      FRAP
ATOM   1133  N    LEU  2022    -14.051  25.164  11.303  1.00  12.39      FRAP
ATOM   1134  H    LEU  2022    -13.191  24.841  10.981  0.00   0.00      FRAP
ATOM   1135  CA   LEU  2022    -14.967  24.324  12.072  1.00  10.94      FRAP
ATOM   1136  CB   LEU  2022    -14.339  22.958  12.314  1.00   4.40      FRAP
ATOM   1137  CG   LEU  2022    -14.001  22.196  11.041  1.00   3.20      FRAP
ATOM   1138  CD1  LEU  2022    -13.224  20.961  11.400  1.00   2.00      FRAP
ATOM   1139  CD2  LEU  2022    -15.279  21.845  10.295  1.00   2.00      FRAP
ATOM   1140  C    LEU  2022    -15.347  24.946  13.414  1.00  11.66      FRAP
ATOM   1141  O    LEU  2022    -14.489  25.468  14.134  1.00  11.57      FRAP
ATOM   1142  N    TRP  2023    -16.628  24.838  13.766  1.00  11.70      FRAP
ATOM   1143  H    TRP  2023    -17.279  24.666  13.058  0.00   0.00      FRAP
ATOM   1144  CA   TRP  2023    -17.128  25.262  15.079  1.00  13.42      FRAP
ATOM   1145  CB   TRP  2023    -18.624  24.943  15.192  1.00   6.83      FRAP
ATOM   1146  CG   TRP  2023    -19.499  25.971  14.562  1.00   2.00      FRAP
ATOM   1147  CD2  TRP  2023    -20.927  26.075  14.671  1.00   2.00      FRAP
ATOM   1148  CE2  TRP  2023    -21.309  27.257  14.015  1.00   2.00      FRAP
ATOM   1149  CE3  TRP  2023    -21.917  25.288  15.267  1.00   2.00      FRAP
ATOM   1150  CD1  TRP  2023    -19.093  27.063  13.854  1.00   2.00      FRAP
```

Figure 4: A-24

```
ATOM   1151  NE1 TRP 2023     -20.169  27.839  13.525  1.00  2.00       FRAP
ATOM   1152  HE1 TRP 2023     -20.112  28.705  13.064  0.00  0.00       FRAP
ATOM   1153  CZ2 TRP 2023     -22.640  27.672  13.937  1.00  2.00       FRAP
ATOM   1154  CZ3 TRP 2023     -23.241  25.706  15.188  1.00  2.00       FRAP
ATOM   1155  CH2 TRP 2023     -23.585  26.881  14.528  1.00  2.00       FRAP
ATOM   1156  C   TRP 2023     -16.359  24.603  16.230  1.00 14.99       FRAP
ATOM   1157  O   TRP 2023     -16.174  25.189  17.292  1.00 20.57       FRAP
ATOM   1158  N   HIS 2024     -15.921  23.373  15.999  1.00 17.48       FRAP
ATOM   1159  H   HIS 2024     -16.377  22.943  15.254  0.00  0.00       FRAP
ATOM   1160  CA  HIS 2024     -14.969  22.689  16.871  1.00 19.39       FRAP
ATOM   1161  CB  HIS 2024     -14.560  21.346  16.234  1.00 25.50       FRAP
ATOM   1162  CG  HIS 2024     -15.693  20.627  15.555  1.00 33.39       FRAP
ATOM   1163  CD2 HIS 2024     -16.181  20.726  14.293  1.00 33.72       FRAP
ATOM   1164  ND1 HIS 2024     -16.571  19.807  16.233  1.00 41.22       FRAP
ATOM   1165  HD1 HIS 2024     -16.490  19.465  17.152  0.00  0.00       FRAP
ATOM   1166  CE1 HIS 2024     -17.559  19.450  15.429  1.00 38.35       FRAP
ATOM   1167  NE2 HIS 2024     -17.347  19.999  14.248  1.00 38.10       FRAP
ATOM   1168  HE2 HIS 2024     -17.975  19.937  13.490  0.00  0.00       FRAP
ATOM   1169  C   HIS 2024     -13.728  23.558  17.158  1.00 19.84       FRAP
ATOM   1170  O   HIS 2024     -13.541  24.012  18.280  1.00 22.62       FRAP
ATOM   1171  N   GLU 2025     -12.963  23.906  16.127  1.00 20.21       FRAP
ATOM   1172  H   GLU 2025     -13.279  23.712  15.223  0.00  0.00       FRAP
ATOM   1173  CA  GLU 2025     -11.732  24.686  16.318  1.00 20.43       FRAP
ATOM   1174  CB  GLU 2025     -10.969  24.846  14.994  1.00 27.02       FRAP
ATOM   1175  CG  GLU 2025     -10.961  23.614  14.089  1.00 41.60       FRAP
ATOM   1176  CD  GLU 2025     -10.550  23.937  12.652  1.00 47.27       FRAP
ATOM   1177  OE1 GLU 2025      -9.330  23.903  12.369  1.00 54.42       FRAP
ATOM   1178  OE2 GLU 2025     -11.440  24.219  11.810  1.00 37.45       FRAP
ATOM   1179  C   GLU 2025     -12.037  26.074  16.875  1.00 17.30       FRAP
ATOM   1180  O   GLU 2025     -11.268  26.641  17.651  1.00 15.80       FRAP
ATOM   1181  N   MET 2026     -13.159  26.625  16.444  1.00 15.93       FRAP
ATOM   1182  H   MET 2026     -13.715  26.119  15.820  0.00  0.00       FRAP
ATOM   1183  CA  MET 2026     -13.552  27.971  16.816  1.00 18.01       FRAP
ATOM   1184  CB  MET 2026     -14.806  28.354  16.021  1.00 21.46       FRAP
ATOM   1185  CG  MET 2026     -15.619  29.490  16.603  1.00 28.72       FRAP
ATOM   1186  SD  MET 2026     -16.931  30.032  15.505  1.00 34.40       FRAP
ATOM   1187  CE  MET 2026     -15.938  30.642  14.095  1.00 36.70       FRAP
ATOM   1188  C   MET 2026     -13.805  28.060  18.325  1.00 18.72       FRAP
ATOM   1189  O   MET 2026     -13.257  28.927  19.012  1.00 18.88       FRAP
ATOM   1190  N   TRP 2027     -14.553  27.092  18.845  1.00 18.28       FRAP
ATOM   1191  H   TRP 2027     -14.929  26.414  18.243  0.00  0.00       FRAP
ATOM   1192  CA  TRP 2027     -14.890  27.047  20.263  1.00 16.52       FRAP
ATOM   1193  CB  TRP 2027     -16.087  26.129  20.481  1.00 14.68       FRAP
ATOM   1194  CG  TRP 2027     -17.381  26.861  20.453  1.00 16.26       FRAP
ATOM   1195  CD2 TRP 2027     -17.870  27.760  21.450  1.00 16.49       FRAP
ATOM   1196  CE2 TRP 2027     -19.120  28.239  21.003  1.00 15.26       FRAP
ATOM   1197  CE3 TRP 2027     -17.373  28.214  22.681  1.00 18.70       FRAP
ATOM   1198  CD1 TRP 2027     -18.322  26.831  19.466  1.00 16.17       FRAP
ATOM   1199  NE1 TRP 2027     -19.370  27.656  19.789  1.00 13.89       FRAP
ATOM   1200  HE1 TRP 2027     -20.150  27.816  19.215  0.00  0.00       FRAP
```

Figure 4: A-25

```
ATOM   1201  CZ2  TRP  2027    -19.886  29.142  21.745  1.00  17.88      FRAP
ATOM   1202  CZ3  TRP  2027    -18.133  29.114  23.421  1.00  17.25      FRAP
ATOM   1203  CH2  TRP  2027    -19.376  29.565  22.950  1.00  21.47      FRAP
ATOM   1204  C    TRP  2027    -13.736  26.609  21.159  1.00  15.61      FRAP
ATOM   1205  O    TRP  2027    -13.561  27.129  22.254  1.00  18.72      FRAP
ATOM   1206  N    HIS  2028    -12.906  25.702  20.665  1.00  11.04      FRAP
ATOM   1207  H    HIS  2028    -13.152  25.290  19.807  0.00   0.00      FRAP
ATOM   1208  CA   HIS  2028    -11.735  25.275  21.412  1.00  10.15      FRAP
ATOM   1209  CB   HIS  2028    -10.920  24.282  20.604  1.00   9.23      FRAP
ATOM   1210  CG   HIS  2028     -9.821  23.642  21.389  1.00  10.39      FRAP
ATOM   1211  CD2  HIS  2028     -9.786  22.484  22.091  1.00   8.51      FRAP
ATOM   1212  ND1  HIS  2028     -8.575  24.215  21.529  1.00  13.26      FRAP
ATOM   1213  HD1  HIS  2028     -8.284  25.084  21.180  0.00   0.00      FRAP
ATOM   1214  CE1  HIS  2028     -7.814  23.433  22.276  1.00  15.69      FRAP
ATOM   1215  NE2  HIS  2028     -8.527  22.377  22.629  1.00  18.29      FRAP
ATOM   1216  HE2  HIS  2028     -8.221  21.579  23.119  0.00   0.00      FRAP
ATOM   1217  C    HIS  2028    -10.827  26.424  21.805  1.00  10.27      FRAP
ATOM   1218  O    HIS  2028    -10.401  26.519  22.941  1.00  10.19      FRAP
ATOM   1219  N    GLU  2029    -10.360  27.167  20.817  1.00  19.72      FRAP
ATOM   1220  H    GLU  2029    -10.688  27.017  19.900  0.00   0.00      FRAP
ATOM   1221  CA   GLU  2029     -9.433  28.257  21.093  1.00  27.56      FRAP
ATOM   1222  CB   GLU  2029     -8.601  28.592  19.843  1.00  34.06      FRAP
ATOM   1223  CG   GLU  2029     -9.401  28.822  18.565  1.00  44.39      FRAP
ATOM   1224  CD   GLU  2029     -8.554  28.678  17.307  1.00  50.63      FRAP
ATOM   1225  OE1  GLU  2029     -8.624  29.570  16.429  1.00  54.55      FRAP
ATOM   1226  OE2  GLU  2029     -7.828  27.664  17.191  1.00  51.32      FRAP
ATOM   1227  C    GLU  2029    -10.133  29.508  21.642  1.00  27.45      FRAP
ATOM   1228  O    GLU  2029     -9.533  30.277  22.392  1.00  29.68      FRAP
ATOM   1229  N    GLY  2030    -11.433  29.634  21.380  1.00  25.66      FRAP
ATOM   1230  H    GLY  2030    -11.843  29.093  20.670  0.00   0.00      FRAP
ATOM   1231  CA   GLY  2030    -12.214  30.696  21.997  1.00  21.35      FRAP
ATOM   1232  C    GLY  2030    -12.307  30.538  23.504  1.00  16.02      FRAP
ATOM   1233  O    GLY  2030    -11.837  31.390  24.257  1.00  17.01      FRAP
ATOM   1234  N    LEU  2031    -12.767  29.368  23.932  1.00  11.25      FRAP
ATOM   1235  H    LEU  2031    -13.130  28.749  23.264  0.00   0.00      FRAP
ATOM   1236  CA   LEU  2031    -12.805  29.012  25.341  1.00   6.54      FRAP
ATOM   1237  CB   LEU  2031    -13.382  27.612  25.511  1.00   2.00      FRAP
ATOM   1238  CG   LEU  2031    -14.869  27.475  25.192  1.00   2.25      FRAP
ATOM   1239  CD1  LEU  2031    -15.347  26.079  25.568  1.00   2.00      FRAP
ATOM   1240  CD2  LEU  2031    -15.656  28.530  25.936  1.00   2.00      FRAP
ATOM   1241  C    LEU  2031    -11.441  29.088  26.024  1.00  10.09      FRAP
ATOM   1242  O    LEU  2031    -11.337  29.538  27.168  1.00  16.95      FRAP
ATOM   1243  N    GLU  2032    -10.386  28.657  25.348  1.00   8.34      FRAP
ATOM   1244  H    GLU  2032    -10.522  28.216  24.483  0.00   0.00      FRAP
ATOM   1245  CA   GLU  2032     -9.068  28.756  25.957  1.00  12.37      FRAP
ATOM   1246  CB   GLU  2032     -8.028  27.986  25.146  1.00  16.26      FRAP
ATOM   1247  CG   GLU  2032     -6.692  27.831  25.861  1.00  23.62      FRAP
ATOM   1248  CD   GLU  2032     -5.792  26.772  25.235  1.00  30.03      FRAP
ATOM   1249  OE1  GLU  2032     -4.617  27.092  24.948  1.00  31.98      FRAP
ATOM   1250  OE2  GLU  2032     -6.241  25.611  25.078  1.00  32.01      FRAP
```

Figure 4: A-26

```
ATOM   1251  C    GLU  2032       -8.629  30.210  26.154  1.00  12.81        FRAP
ATOM   1252  O    GLU  2032       -8.263  30.588  27.261  1.00  21.81        FRAP
ATOM   1253  N    GLU  2033       -8.837  31.053  25.147  1.00  11.47        FRAP
ATOM   1254  H    GLU  2033       -9.243  30.710  24.323  0.00   0.00        FRAP
ATOM   1255  CA   GLU  2033       -8.462  32.473  25.225  1.00  12.69        FRAP
ATOM   1256  CB   GLU  2033       -8.631  33.140  23.854  1.00  19.44        FRAP
ATOM   1257  CG   GLU  2033       -7.834  34.437  23.650  1.00  30.82        FRAP
ATOM   1258  CD   GLU  2033       -8.155  35.152  22.319  1.00  42.12        FRAP
ATOM   1259  OE1  GLU  2033       -7.793  36.346  22.186  1.00  44.44        FRAP
ATOM   1260  OE2  GLU  2033       -8.759  34.530  21.408  1.00  39.63        FRAP
ATOM   1261  C    GLU  2033       -9.308  33.226  26.254  1.00  10.31        FRAP
ATOM   1262  O    GLU  2033       -8.808  34.068  26.994  1.00   6.92        FRAP
ATOM   1263  N    ALA  2034      -10.600  32.933  26.275  1.00   6.18        FRAP
ATOM   1264  H    ALA  2034      -10.945  32.334  25.587  0.00   0.00        FRAP
ATOM   1265  CA   ALA  2034      -11.509  33.572  27.205  1.00   2.76        FRAP
ATOM   1266  CB   ALA  2034      -12.920  33.101  26.943  1.00   2.50        FRAP
ATOM   1267  C    ALA  2034      -11.101  33.257  28.641  1.00   6.07        FRAP
ATOM   1268  O    ALA  2034      -10.907  34.157  29.453  1.00  11.33        FRAP
ATOM   1269  N    SER  2035      -10.811  31.988  28.903  1.00   8.47        FRAP
ATOM   1270  H    SER  2035      -10.871  31.330  28.175  0.00   0.00        FRAP
ATOM   1271  CA   SER  2035      -10.482  31.543  30.250  1.00   4.56        FRAP
ATOM   1272  CB   SER  2035      -10.357  30.016  30.294  1.00   2.00        FRAP
ATOM   1273  OG   SER  2035       -9.012  29.595  30.200  1.00   7.26        FRAP
ATOM   1274  HG   SER  2035       -8.700  29.696  29.288  0.00   0.00        FRAP
ATOM   1275  C    SER  2035       -9.201  32.193  30.749  1.00   5.40        FRAP
ATOM   1276  O    SER  2035       -9.171  32.734  31.846  1.00  11.51        FRAP
ATOM   1277  N    ARG  2036       -8.195  32.265  29.886  1.00   3.96        FRAP
ATOM   1278  H    ARG  2036       -8.314  31.862  28.998  0.00   0.00        FRAP
ATOM   1279  CA   ARG  2036       -6.934  32.909  30.233  1.00   6.68        FRAP
ATOM   1280  CB   ARG  2036       -5.959  32.792  29.065  1.00   7.24        FRAP
ATOM   1281  CG   ARG  2036       -4.695  33.631  29.210  1.00  17.54        FRAP
ATOM   1282  CD   ARG  2036       -4.229  34.185  27.860  1.00  17.93        FRAP
ATOM   1283  NE   ARG  2036       -3.637  35.515  27.997  1.00  18.57        FRAP
ATOM   1284  HE   ARG  2036       -2.897  35.626  28.628  0.00   0.00        FRAP
ATOM   1285  CZ   ARG  2036       -4.055  36.595  27.344  1.00  20.32        FRAP
ATOM   1286  NH1  ARG  2036       -3.456  37.762  27.540  1.00  24.32        FRAP
ATOM   1287  HH11 ARG  2036       -2.689  37.827  28.180  0.00   0.00        FRAP
ATOM   1288  HH12 ARG  2036       -3.766  38.572  27.045  0.00   0.00        FRAP
ATOM   1289  NH2  ARG  2036       -5.080  36.518  26.505  1.00  20.76        FRAP
ATOM   1290  HH21 ARG  2036       -5.564  35.653  26.375  0.00   0.00        FRAP
ATOM   1291  HH22 ARG  2036       -5.391  37.341  26.030  0.00   0.00        FRAP
ATOM   1292  C    ARG  2036       -7.110  34.382  30.624  1.00   9.31        FRAP
ATOM   1293  O    ARG  2036       -6.463  34.872  31.548  1.00  12.91        FRAP
ATOM   1294  N    LEU  2037       -8.041  35.057  29.964  1.00  10.78        FRAP
ATOM   1295  H    LEU  2037       -8.541  34.590  29.261  0.00   0.00        FRAP
ATOM   1296  CA   LEU  2037       -8.309  36.466  30.214  1.00   8.83        FRAP
ATOM   1297  CB   LEU  2037       -9.163  37.034  29.084  1.00   9.75        FRAP
ATOM   1298  CG   LEU  2037       -8.302  37.375  27.873  1.00   8.95        FRAP
ATOM   1299  CD1  LEU  2037       -9.130  37.388  26.613  1.00  11.32        FRAP
ATOM   1300  CD2  LEU  2037       -7.624  38.713  28.110  1.00   7.83        FRAP
```

Figure 4: A-27

```
ATOM   1301  C    LEU  2037      -9.004  36.692  31.543  1.00 12.66      FRAP
ATOM   1302  O    LEU  2037      -8.626  37.583  32.295  1.00 17.85      FRAP
ATOM   1303  N    TYR  2038     -10.020  35.886  31.832  1.00 11.90      FRAP
ATOM   1304  H    TYR  2038     -10.327  35.266  31.130  0.00  0.00      FRAP
ATOM   1305  CA   TYR  2038     -10.693  35.930  33.132  1.00 11.68      FRAP
ATOM   1306  CB   TYR  2038     -12.006  35.138  33.071  1.00  9.29      FRAP
ATOM   1307  CG   TYR  2038     -12.761  35.090  34.375  1.00 12.17      FRAP
ATOM   1308  CD1  TYR  2038     -12.942  36.239  35.143  1.00 10.58      FRAP
ATOM   1309  CE1  TYR  2038     -13.555  36.181  36.391  1.00 17.63      FRAP
ATOM   1310  CD2  TYR  2038     -13.230  33.880  34.884  1.00 17.46      FRAP
ATOM   1311  CE2  TYR  2038     -13.850  33.810  36.131  1.00 17.47      FRAP
ATOM   1312  CZ   TYR  2038     -14.006  34.962  36.880  1.00 18.99      FRAP
ATOM   1313  OH   TYR  2038     -14.596  34.893  38.123  1.00 22.39      FRAP
ATOM   1314  HH   TYR  2038     -15.321  34.267  38.078  0.00  0.00      FRAP
ATOM   1315  C    TYR  2038      -9.811  35.403  34.277  1.00 13.86      FRAP
ATOM   1316  O    TYR  2038      -9.408  36.164  35.158  1.00 17.65      FRAP
ATOM   1317  N    PHE  2039      -9.481  34.113  34.235  1.00 13.85      FRAP
ATOM   1318  H    PHE  2039      -9.764  33.595  33.452  0.00  0.00      FRAP
ATOM   1319  CA   PHE  2039      -8.717  33.455  35.299  1.00 10.83      FRAP
ATOM   1320  CB   PHE  2039      -8.665  31.950  35.054  1.00  2.58      FRAP
ATOM   1321  CG   PHE  2039      -9.988  31.281  35.235  1.00  6.64      FRAP
ATOM   1322  CD1  PHE  2039     -10.540  31.147  36.510  1.00  4.84      FRAP
ATOM   1323  CD2  PHE  2039     -10.745  30.902  34.131  1.00  2.79      FRAP
ATOM   1324  CE1  PHE  2039     -11.828  30.656  36.680  1.00  5.26      FRAP
ATOM   1325  CE2  PHE  2039     -12.039  30.408  34.292  1.00  2.18      FRAP
ATOM   1326  CZ   PHE  2039     -12.581  30.287  35.563  1.00  4.94      FRAP
ATOM   1327  C    PHE  2039      -7.306  33.980  35.460  1.00 14.37      FRAP
ATOM   1328  O    PHE  2039      -6.861  34.248  36.579  1.00 15.23      FRAP
ATOM   1329  N    GLY  2040      -6.619  34.155  34.336  1.00 17.70      FRAP
ATOM   1330  H    GLY  2040      -7.060  34.013  33.471  0.00  0.00      FRAP
ATOM   1331  CA   GLY  2040      -5.221  34.544  34.369  1.00 19.07      FRAP
ATOM   1332  C    GLY  2040      -4.954  36.026  34.561  1.00 19.43      FRAP
ATOM   1333  O    GLY  2040      -3.957  36.384  35.180  1.00 24.65      FRAP
ATOM   1334  N    GLU  2041      -5.815  36.881  34.012  1.00 17.18      FRAP
ATOM   1335  H    GLU  2041      -6.555  36.502  33.494  0.00  0.00      FRAP
ATOM   1336  CA   GLU  2041      -5.590  38.328  34.019  1.00 16.74      FRAP
ATOM   1337  CB   GLU  2041      -5.476  38.867  32.589  1.00 21.26      FRAP
ATOM   1338  CG   GLU  2041      -5.030  37.856  31.544  1.00 34.57      FRAP
ATOM   1339  CD   GLU  2041      -3.792  38.302  30.785  1.00 39.88      FRAP
ATOM   1340  OE1  GLU  2041      -3.772  39.459  30.303  1.00 41.61      FRAP
ATOM   1341  OE2  GLU  2041      -2.844  37.489  30.664  1.00 43.16      FRAP
ATOM   1342  C    GLU  2041      -6.689  39.108  34.733  1.00 16.00      FRAP
ATOM   1343  O    GLU  2041      -6.754  40.330  34.629  1.00 16.19      FRAP
ATOM   1344  N    ARG  2042      -7.626  38.392  35.340  1.00 16.54      FRAP
ATOM   1345  H    ARG  2042      -7.540  37.419  35.364  0.00  0.00      FRAP
ATOM   1346  CA   ARG  2042      -8.785  39.011  35.974  1.00 17.30      FRAP
ATOM   1347  CB   ARG  2042      -8.389  39.691  37.283  1.00 21.74      FRAP
ATOM   1348  CG   ARG  2042      -8.704  38.869  38.515  1.00 29.43      FRAP
ATOM   1349  CD   ARG  2042      -7.650  37.815  38.736  1.00 31.60      FRAP
ATOM   1350  NE   ARG  2042      -6.318  38.396  38.627  1.00 34.93      FRAP
```

Figure 4: A-28

```
ATOM   1351  HE   ARG  2042      -6.148  39.074  37.940  0.00   0.00      FRAP
ATOM   1352  CZ   ARG  2042      -5.273  38.026  39.358  1.00  41.93      FRAP
ATOM   1353  NH1  ARG  2042      -4.097  38.606  39.146  1.00  43.89      FRAP
ATOM   1354  HH11 ARG  2042      -4.011  39.312  38.444  0.00   0.00      FRAP
ATOM   1355  HH12 ARG  2042      -3.309  38.359  39.710  0.00   0.00      FRAP
ATOM   1356  NH2  ARG  2042      -5.398  37.089  40.296  1.00  42.95      FRAP
ATOM   1357  HH21 ARG  2042      -6.289  36.673  40.485  0.00   0.00      FRAP
ATOM   1358  HH22 ARG  2042      -4.609  36.857  40.865  0.00   0.00      FRAP
ATOM   1359  C    ARG  2042      -9.485  40.015  35.074  1.00  15.46      FRAP
ATOM   1360  O    ARG  2042     -10.031  41.009  35.550  1.00  17.81      FRAP
ATOM   1361  N    ASN  2043      -9.560  39.689  33.789  1.00  13.57      FRAP
ATOM   1362  H    ASN  2043      -9.152  38.845  33.525  0.00   0.00      FRAP
ATOM   1363  CA   ASN  2043     -10.219  40.545  32.805  1.00  12.63      FRAP
ATOM   1364  CB   ASN  2043      -9.322  40.702  31.567  1.00   9.40      FRAP
ATOM   1365  CG   ASN  2043      -9.673  41.928  30.734  1.00  13.89      FRAP
ATOM   1366  OD1  ASN  2043     -10.778  42.457  30.805  1.00  13.79      FRAP
ATOM   1367  ND2  ASN  2043      -8.725  42.382  29.941  1.00  19.98      FRAP
ATOM   1368  HD21 ASN  2043      -7.861  41.929  29.933  0.00   0.00      FRAP
ATOM   1369  HD22 ASN  2043      -8.951  43.171  29.415  0.00   0.00      FRAP
ATOM   1370  C    ASN  2043     -11.589  39.985  32.399  1.00  11.08      FRAP
ATOM   1371  O    ASN  2043     -11.704  39.254  31.410  1.00  15.73      FRAP
ATOM   1372  N    VAL  2044     -12.622  40.329  33.164  1.00   7.83      FRAP
ATOM   1373  H    VAL  2044     -12.407  40.817  33.986  0.00   0.00      FRAP
ATOM   1374  CA   VAL  2044     -13.996  39.930  32.841  1.00   8.89      FRAP
ATOM   1375  CB   VAL  2044     -14.942  40.079  34.049  1.00   4.93      FRAP
ATOM   1376  CG1  VAL  2044     -16.254  39.343  33.783  1.00   2.00      FRAP
ATOM   1377  CG2  VAL  2044     -14.280  39.541  35.300  1.00   6.55      FRAP
ATOM   1378  C    VAL  2044     -14.599  40.724  31.680  1.00  12.31      FRAP
ATOM   1379  O    VAL  2044     -15.607  40.328  31.111  1.00  16.97      FRAP
ATOM   1380  N    LYS  2045     -14.013  41.873  31.366  1.00  15.26      FRAP
ATOM   1381  H    LYS  2045     -13.326  42.230  31.961  0.00   0.00      FRAP
ATOM   1382  CA   LYS  2045     -14.387  42.614  30.158  1.00  18.66      FRAP
ATOM   1383  CB   LYS  2045     -13.791  44.027  30.205  1.00  20.39      FRAP
ATOM   1384  CG   LYS  2045     -13.868  44.787  28.894  1.00  27.87      FRAP
ATOM   1385  CD   LYS  2045     -12.848  45.913  28.846  1.00  36.04      FRAP
ATOM   1386  CE   LYS  2045     -13.013  46.763  27.592  1.00  39.79      FRAP
ATOM   1387  NZ   LYS  2045     -12.203  48.015  27.646  1.00  42.34      FRAP
ATOM   1388  HZ1  LYS  2045     -11.194  47.773  27.696  0.00   0.00      FRAP
ATOM   1389  HZ2  LYS  2045     -12.477  48.555  28.491  0.00   0.00      FRAP
ATOM   1390  HZ3  LYS  2045     -12.387  48.579  26.791  0.00   0.00      FRAP
ATOM   1391  C    LYS  2045     -13.912  41.880  28.890  1.00  15.74      FRAP
ATOM   1392  O    LYS  2045     -14.697  41.616  27.982  1.00  15.10      FRAP
ATOM   1393  N    GLY  2046     -12.640  41.493  28.885  1.00  13.71      FRAP
ATOM   1394  H    GLY  2046     -12.091  41.759  29.647  0.00   0.00      FRAP
ATOM   1395  CA   GLY  2046     -12.063  40.767  27.768  1.00  11.16      FRAP
ATOM   1396  C    GLY  2046     -12.716  39.427  27.486  1.00  11.68      FRAP
ATOM   1397  O    GLY  2046     -13.079  39.138  26.350  1.00  12.25      FRAP
ATOM   1398  N    MET  2047     -12.944  38.632  28.522  1.00  14.02      FRAP
ATOM   1399  H    MET  2047     -12.639  38.911  29.412  0.00   0.00      FRAP
ATOM   1400  CA   MET  2047     -13.555  37.327  28.317  1.00  12.90      FRAP
```

Figure 4: A-29

```
ATOM   1401  CB   MET  2047   -13.571  36.520  29.625  1.00   9.26      FRAP
ATOM   1402  CG   MET  2047   -14.762  36.725  30.521  1.00   6.02      FRAP
ATOM   1403  SD   MET  2047   -15.175  35.189  31.335  1.00   6.46      FRAP
ATOM   1404  CE   MET  2047   -16.865  35.461  31.714  1.00   4.80      FRAP
ATOM   1405  C    MET  2047   -14.954  37.413  27.691  1.00  14.99      FRAP
ATOM   1406  O    MET  2047   -15.275  36.624  26.816  1.00  20.34      FRAP
ATOM   1407  N    PHE  2048   -15.710  38.465  28.001  1.00  13.61      FRAP
ATOM   1408  H    PHE  2048   -15.410  39.078  28.703  0.00   0.00      FRAP
ATOM   1409  CA   PHE  2048   -16.992  38.707  27.324  1.00  12.00      FRAP
ATOM   1410  CB   PHE  2048   -17.754  39.849  28.012  1.00  15.37      FRAP
ATOM   1411  CG   PHE  2048   -18.356  39.479  29.357  1.00  19.64      FRAP
ATOM   1412  CD1  PHE  2048   -18.849  38.201  29.600  1.00  20.36      FRAP
ATOM   1413  CD2  PHE  2048   -18.506  40.442  30.352  1.00  17.04      FRAP
ATOM   1414  CE1  PHE  2048   -19.481  37.901  30.806  1.00  12.14      FRAP
ATOM   1415  CE2  PHE  2048   -19.137  40.138  31.552  1.00   7.86      FRAP
ATOM   1416  CZ   PHE  2048   -19.623  38.875  31.774  1.00   2.66      FRAP
ATOM   1417  C    PHE  2048   -16.785  39.054  25.839  1.00  11.47      FRAP
ATOM   1418  O    PHE  2048   -17.540  38.619  24.968  1.00   9.57      FRAP
ATOM   1419  N    GLU  2049   -15.754  39.843  25.558  1.00  10.97      FRAP
ATOM   1420  H    GLU  2049   -15.274  40.244  26.315  0.00   0.00      FRAP
ATOM   1421  CA   GLU  2049   -15.368  40.161  24.189  1.00  12.08      FRAP
ATOM   1422  CB   GLU  2049   -14.144  41.090  24.187  1.00  18.49      FRAP
ATOM   1423  CG   GLU  2049   -14.432  42.512  24.700  1.00  28.61      FRAP
ATOM   1424  CD   GLU  2049   -13.244  43.464  24.566  1.00  32.92      FRAP
ATOM   1425  OE1  GLU  2049   -13.006  44.240  25.521  1.00  34.23      FRAP
ATOM   1426  OE2  GLU  2049   -12.598  43.492  23.489  1.00  32.94      FRAP
ATOM   1427  C    GLU  2049   -15.072  38.890  23.387  1.00  10.88      FRAP
ATOM   1428  O    GLU  2049   -15.771  38.579  22.427  1.00  12.08      FRAP
ATOM   1429  N    VAL  2050   -14.120  38.096  23.862  1.00  10.17      FRAP
ATOM   1430  H    VAL  2050   -13.667  38.388  24.675  0.00   0.00      FRAP
ATOM   1431  CA   VAL  2050   -13.800  36.807  23.247  1.00  10.01      FRAP
ATOM   1432  CB   VAL  2050   -12.318  36.446  23.457  1.00   6.62      FRAP
ATOM   1433  CG1  VAL  2050   -11.942  36.639  24.901  1.00  11.08      FRAP
ATOM   1434  CG2  VAL  2050   -12.039  35.006  22.995  1.00  11.04      FRAP
ATOM   1435  C    VAL  2050   -14.693  35.680  23.781  1.00  14.92      FRAP
ATOM   1436  O    VAL  2050   -14.244  34.799  24.529  1.00  20.63      FRAP
ATOM   1437  N    LEU  2051   -15.981  35.775  23.454  1.00  12.19      FRAP
ATOM   1438  H    LEU  2051   -16.263  36.655  23.111  0.00   0.00      FRAP
ATOM   1439  CA   LEU  2051   -16.971  34.764  23.816  1.00   9.54      FRAP
ATOM   1440  CB   LEU  2051   -17.122  34.686  25.336  1.00   8.37      FRAP
ATOM   1441  CG   LEU  2051   -17.216  33.329  26.046  1.00   8.86      FRAP
ATOM   1442  CD1  LEU  2051   -16.110  32.395  25.592  1.00   5.79      FRAP
ATOM   1443  CD2  LEU  2051   -17.118  33.550  27.538  1.00   2.00      FRAP
ATOM   1444  C    LEU  2051   -18.310  35.117  23.188  1.00  10.79      FRAP
ATOM   1445  O    LEU  2051   -19.052  34.237  22.752  1.00  14.03      FRAP
ATOM   1446  N    GLU  2052   -18.562  36.413  23.042  1.00  11.63      FRAP
ATOM   1447  H    GLU  2052   -17.932  37.078  23.408  0.00   0.00      FRAP
ATOM   1448  CA   GLU  2052   -19.837  36.897  22.525  1.00  13.53      FRAP
ATOM   1449  CB   GLU  2052   -19.980  38.399  22.792  1.00  18.53      FRAP
ATOM   1450  CG   GLU  2052   -21.396  38.835  23.103  1.00  29.17      FRAP
```

Figure 4: A-30

| | | | | | | | | | | |
|---|---|---|---|---|---|---|---|---|---|---|
| ATOM | 1451 | CD  | GLU | 2052 | -21.530 | 40.343 | 23.220 | 1.00 | 34.41 | FRAP |
| ATOM | 1452 | OE1 | GLU | 2052 | -22.567 | 40.884 | 22.772 | 1.00 | 39.61 | FRAP |
| ATOM | 1453 | OE2 | GLU | 2052 | -20.605 | 40.987 | 23.766 | 1.00 | 36.83 | FRAP |
| ATOM | 1454 | C   | GLU | 2052 | -20.059 | 36.587 | 21.044 | 1.00 | 9.88  | FRAP |
| ATOM | 1455 | O   | GLU | 2052 | -21.045 | 35.948 | 20.693 | 1.00 | 11.10 | FRAP |
| ATOM | 1456 | N   | PRO | 2053 | -19.085 | 36.922 | 20.175 | 1.00 | 9.83  | FRAP |
| ATOM | 1457 | CD  | PRO | 2053 | -18.104 | 38.004 | 20.386 | 1.00 | 7.70  | FRAP |
| ATOM | 1458 | CA  | PRO | 2053 | -18.978 | 36.374 | 18.814 | 1.00 | 9.97  | FRAP |
| ATOM | 1459 | CB  | PRO | 2053 | -17.537 | 36.674 | 18.444 | 1.00 | 12.18 | FRAP |
| ATOM | 1460 | CG  | PRO | 2053 | -17.265 | 37.981 | 19.139 | 1.00 | 11.41 | FRAP |
| ATOM | 1461 | C   | PRO | 2053 | -19.301 | 34.882 | 18.639 | 1.00 | 11.69 | FRAP |
| ATOM | 1462 | O   | PRO | 2053 | -20.157 | 34.520 | 17.837 | 1.00 | 15.54 | FRAP |
| ATOM | 1463 | N   | LEU | 2054 | -18.588 | 34.021 | 19.362 | 1.00 | 12.26 | FRAP |
| ATOM | 1464 | H   | LEU | 2054 | -17.894 | 34.386 | 19.944 | 0.00 | 0.00  | FRAP |
| ATOM | 1465 | CA  | LEU | 2054 | -18.813 | 32.574 | 19.304 | 1.00 | 7.01  | FRAP |
| ATOM | 1466 | CB  | LEU | 2054 | -17.897 | 31.859 | 20.296 | 1.00 | 2.00  | FRAP |
| ATOM | 1467 | CG  | LEU | 2054 | -16.431 | 32.303 | 20.307 | 1.00 | 2.00  | FRAP |
| ATOM | 1468 | CD1 | LEU | 2054 | -15.603 | 31.503 | 21.299 | 1.00 | 2.00  | FRAP |
| ATOM | 1469 | CD2 | LEU | 2054 | -15.873 | 32.146 | 18.921 | 1.00 | 12.00 | FRAP |
| ATOM | 1470 | C   | LEU | 2054 | -20.267 | 32.247 | 19.621 | 1.00 | 6.82  | FRAP |
| ATOM | 1471 | O   | LEU | 2054 | -20.928 | 31.510 | 18.895 | 1.00 | 7.84  | FRAP |
| ATOM | 1472 | N   | HIS | 2055 | -20.805 | 32.908 | 20.632 | 1.00 | 4.28  | FRAP |
| ATOM | 1473 | H   | HIS | 2055 | -20.241 | 33.532 | 21.142 | 0.00 | 0.00  | FRAP |
| ATOM | 1474 | CA  | HIS | 2055 | -22.205 | 32.716 | 20.965 | 1.00 | 5.58  | FRAP |
| ATOM | 1475 | CB  | HIS | 2055 | -22.533 | 33.366 | 22.310 | 1.00 | 5.95  | FRAP |
| ATOM | 1476 | CG  | HIS | 2055 | -22.237 | 32.495 | 23.491 | 1.00 | 2.00  | FRAP |
| ATOM | 1477 | CD2 | HIS | 2055 | -21.136 | 32.399 | 24.270 | 1.00 | 2.00  | FRAP |
| ATOM | 1478 | ND1 | HIS | 2055 | -23.118 | 31.542 | 23.952 | 1.00 | 2.00  | FRAP |
| ATOM | 1479 | HD1 | HIS | 2055 | -24.025 | 31.364 | 23.581 | 0.00 | 0.00  | FRAP |
| ATOM | 1480 | CE1 | HIS | 2055 | -22.569 | 30.891 | 24.960 | 1.00 | 2.00  | FRAP |
| ATOM | 1481 | NE2 | HIS | 2055 | -21.362 | 31.384 | 25.166 | 1.00 | 3.10  | FRAP |
| ATOM | 1482 | HE2 | HIS | 2055 | -20.608 | 30.877 | 25.532 | 0.00 | 0.00  | FRAP |
| ATOM | 1483 | C   | HIS | 2055 | -23.118 | 33.276 | 19.884 | 1.00 | 8.31  | FRAP |
| ATOM | 1484 | O   | HIS | 2055 | -24.215 | 32.765 | 19.667 | 1.00 | 14.91 | FRAP |
| ATOM | 1485 | N   | ALA | 2056 | -22.644 | 34.290 | 19.170 | 1.00 | 10.33 | FRAP |
| ATOM | 1486 | H   | ALA | 2056 | -21.767 | 34.651 | 19.397 | 0.00 | 0.00  | FRAP |
| ATOM | 1487 | CA  | ALA | 2056 | -23.442 | 34.935 | 18.130 | 1.00 | 10.51 | FRAP |
| ATOM | 1488 | CB  | ALA | 2056 | -22.729 | 36.161 | 17.619 | 1.00 | 9.92  | FRAP |
| ATOM | 1489 | C   | ALA | 2056 | -23.731 | 33.985 | 16.974 | 1.00 | 14.24 | FRAP |
| ATOM | 1490 | O   | ALA | 2056 | -24.885 | 33.829 | 16.556 | 1.00 | 17.21 | FRAP |
| ATOM | 1491 | N   | MET | 2057 | -22.680 | 33.340 | 16.476 | 1.00 | 11.79 | FRAP |
| ATOM | 1492 | H   | MET | 2057 | -21.792 | 33.596 | 16.814 | 0.00 | 0.00  | FRAP |
| ATOM | 1493 | CA  | MET | 2057 | -22.810 | 32.294 | 15.469 | 1.00 | 15.13 | FRAP |
| ATOM | 1494 | CB  | MET | 2057 | -21.452 | 31.642 | 15.231 | 1.00 | 17.94 | FRAP |
| ATOM | 1495 | CG  | MET | 2057 | -20.692 | 32.266 | 14.087 | 1.00 | 27.92 | FRAP |
| ATOM | 1496 | SD  | MET | 2057 | -18.979 | 31.767 | 14.037 | 1.00 | 39.79 | FRAP |
| ATOM | 1497 | CE  | MET | 2057 | -18.164 | 33.353 | 14.482 | 1.00 | 41.99 | FRAP |
| ATOM | 1498 | C   | MET | 2057 | -23.842 | 31.222 | 15.834 | 1.00 | 17.76 | FRAP |
| ATOM | 1499 | O   | MET | 2057 | -24.808 | 31.000 | 15.100 | 1.00 | 16.63 | FRAP |
| ATOM | 1500 | N   | MET | 2058 | -23.679 | 30.615 | 17.005 | 1.00 | 20.22 | FRAP |

Figure 4: A-31

```
ATOM   1501  H    MET  2058    -22.898  30.870  17.543  0.00   0.00        FRAP
ATOM   1502  CA   MET  2058    -24.617  29.603  17.489  1.00  21.71        FRAP
ATOM   1503  CB   MET  2058    -24.359  29.323  18.969  1.00  20.36        FRAP
ATOM   1504  CG   MET  2058    -22.991  28.760  19.256  1.00  15.47        FRAP
ATOM   1505  SD   MET  2058    -22.714  27.281  18.302  1.00  20.16        FRAP
ATOM   1506  CE   MET  2058    -23.353  26.049  19.380  1.00  12.03        FRAP
ATOM   1507  C    MET  2058    -26.074  30.032  17.295  1.00  25.10        FRAP
ATOM   1508  O    MET  2058    -26.865  29.330  16.659  1.00  28.18        FRAP
ATOM   1509  N    GLU  2059    -26.375  31.246  17.742  1.00  25.58        FRAP
ATOM   1510  H    GLU  2059    -25.654  31.794  18.125  0.00   0.00        FRAP
ATOM   1511  CA   GLU  2059    -27.725  31.798  17.694  1.00  26.53        FRAP
ATOM   1512  CB   GLU  2059    -27.759  33.099  18.504  1.00  26.67        FRAP
ATOM   1513  CG   GLU  2059    -29.007  33.941  18.330  1.00  28.36        FRAP
ATOM   1514  CD   GLU  2059    -28.701  35.344  17.828  1.00  34.40        FRAP
ATOM   1515  OE1  GLU  2059    -27.515  35.648  17.560  1.00  37.80        FRAP
ATOM   1516  OE2  GLU  2059    -29.653  36.146  17.699  1.00  36.02        FRAP
ATOM   1517  C    GLU  2059    -28.224  32.039  16.261  1.00  24.75        FRAP
ATOM   1518  O    GLU  2059    -29.425  32.148  16.022  1.00  24.66        FRAP
ATOM   1519  N    ARG  2060    -27.303  32.057  15.307  1.00  23.58        FRAP
ATOM   1520  H    ARG  2060    -26.365  31.985  15.562  0.00   0.00        FRAP
ATOM   1521  CA   ARG  2060    -27.660  32.296  13.914  1.00  27.89        FRAP
ATOM   1522  CB   ARG  2060    -26.547  33.091  13.224  1.00  31.68        FRAP
ATOM   1523  CG   ARG  2060    -26.338  34.497  13.808  1.00  33.63        FRAP
ATOM   1524  CD   ARG  2060    -27.275  35.527  13.173  1.00  36.15        FRAP
ATOM   1525  NE   ARG  2060    -28.381  35.927  14.046  1.00  35.55        FRAP
ATOM   1526  HE   ARG  2060    -28.189  36.558  14.770  0.00   0.00        FRAP
ATOM   1527  CZ   ARG  2060    -29.635  35.492  13.924  1.00  37.00        FRAP
ATOM   1528  NH1  ARG  2060    -30.590  35.982  14.704  1.00  38.84        FRAP
ATOM   1529  HH11 ARG  2060    -30.376  36.677  15.389  0.00   0.00        FRAP
ATOM   1530  HH12 ARG  2060    -31.526  35.646  14.601  0.00   0.00        FRAP
ATOM   1531  NH2  ARG  2060    -29.933  34.533  13.057  1.00  33.57        FRAP
ATOM   1532  HH21 ARG  2060    -29.220  34.125  12.486  0.00   0.00        FRAP
ATOM   1533  HH22 ARG  2060    -30.874  34.210  12.967  0.00   0.00        FRAP
ATOM   1534  C    ARG  2060    -27.992  31.021  13.117  1.00  26.90        FRAP
ATOM   1535  O    ARG  2060    -28.925  31.013  12.317  1.00  26.30        FRAP
ATOM   1536  N    GLY  2061    -27.246  29.945  13.351  1.00  27.44        FRAP
ATOM   1537  H    GLY  2061    -26.500  30.030  13.976  0.00   0.00        FRAP
ATOM   1538  CA   GLY  2061    -27.597  28.662  12.758  1.00  23.84        FRAP
ATOM   1539  C    GLY  2061    -26.442  27.751  12.361  1.00  25.08        FRAP
ATOM   1540  O    GLY  2061    -25.500  28.198  11.690  1.00  29.79        FRAP
ATOM   1541  N    PRO  2062    -26.516  26.448  12.695  1.00  21.10        FRAP
ATOM   1542  CD   PRO  2062    -27.590  25.836  13.489  1.00  18.97        FRAP
ATOM   1543  CA   PRO  2062    -25.740  25.433  11.976  1.00  19.45        FRAP
ATOM   1544  CB   PRO  2062    -26.204  24.110  12.585  1.00  14.25        FRAP
ATOM   1545  CG   PRO  2062    -27.072  24.467  13.734  1.00  14.98        FRAP
ATOM   1546  C    PRO  2062    -26.051  25.463  10.487  1.00  21.95        FRAP
ATOM   1547  O    PRO  2062    -27.208  25.349  10.085  1.00  26.38        FRAP
ATOM   1548  N    GLN  2063    -25.048  25.729   9.670  1.00  21.33        FRAP
ATOM   1549  H    GLN  2063    -24.240  26.065  10.056  0.00   0.00        FRAP
ATOM   1550  CA   GLN  2063    -25.258  25.668   8.224  1.00  22.88        FRAP
```

Figure 4: A-32

```
ATOM   1551  CB   GLN  2063     -24.384  26.700   7.510  1.00 25.75      FRAP
ATOM   1552  CG   GLN  2063     -25.131  27.922   7.002  1.00 30.23      FRAP
ATOM   1553  CD   GLN  2063     -24.186  29.035   6.545  1.00 37.47      FRAP
ATOM   1554  OE1  GLN  2063     -23.139  28.776   5.945  1.00 42.91      FRAP
ATOM   1555  NE2  GLN  2063     -24.556  30.280   6.822  1.00 34.40      FRAP
ATOM   1556  HE21 GLN  2063     -25.396  30.488   7.270  0.00  0.00      FRAP
ATOM   1557  HE22 GLN  2063     -23.899  30.917   6.484  0.00  0.00      FRAP
ATOM   1558  C    GLN  2063     -24.930  24.278   7.701  1.00 19.53      FRAP
ATOM   1559  O    GLN  2063     -25.781  23.568   7.181  1.00 22.10      FRAP
ATOM   1560  N    THR  2064     -23.685  23.880   7.897  1.00 16.77      FRAP
ATOM   1561  H    THR  2064     -23.114  24.477   8.406  0.00  0.00      FRAP
ATOM   1562  CA   THR  2064     -23.220  22.593   7.423  1.00 17.61      FRAP
ATOM   1563  CB   THR  2064     -21.689  22.551   7.414  1.00 18.02      FRAP
ATOM   1564  OG1  THR  2064     -21.213  22.465   8.763  1.00 16.37      FRAP
ATOM   1565  HG1  THR  2064     -21.145  21.529   8.956  0.00  0.00      FRAP
ATOM   1566  CG2  THR  2064     -21.128  23.812   6.763  1.00 19.18      FRAP
ATOM   1567  C    THR  2064     -23.743  21.471   8.322  1.00 17.50      FRAP
ATOM   1568  O    THR  2064     -24.272  21.725   9.402  1.00 19.82      FRAP
ATOM   1569  N    LEU  2065     -23.481  20.231   7.922  1.00 17.20      FRAP
ATOM   1570  H    LEU  2065     -23.146  20.079   7.018  0.00  0.00      FRAP
ATOM   1571  CA   LEU  2065     -23.813  19.063   8.731  1.00 13.79      FRAP
ATOM   1572  CB   LEU  2065     -23.667  17.808   7.879  1.00 17.73      FRAP
ATOM   1573  CG   LEU  2065     -24.909  16.954   7.614  1.00 18.83      FRAP
ATOM   1574  CD1  LEU  2065     -26.158  17.819   7.466  1.00 19.10      FRAP
ATOM   1575  CD2  LEU  2065     -24.658  16.129   6.365  1.00 14.71      FRAP
ATOM   1576  C    LEU  2065     -22.940  18.949   9.988  1.00 13.22      FRAP
ATOM   1577  O    LEU  2065     -23.445  18.670  11.070  1.00 12.57      FRAP
ATOM   1578  N    LYS  2066     -21.649  19.264   9.848  1.00  9.29      FRAP
ATOM   1579  H    LYS  2066     -21.297  19.271   8.935  0.00  0.00      FRAP
ATOM   1580  CA   LYS  2066     -20.707  19.308  10.976  1.00  8.13      FRAP
ATOM   1581  CB   LYS  2066     -19.297  19.636  10.475  1.00  2.00      FRAP
ATOM   1582  CG   LYS  2066     -18.442  18.438  10.157  1.00  2.00      FRAP
ATOM   1583  CD   LYS  2066     -17.028  18.870   9.846  1.00  2.00      FRAP
ATOM   1584  CE   LYS  2066     -16.122  17.672   9.553  1.00  9.62      FRAP
ATOM   1585  NZ   LYS  2066     -16.549  16.861   8.378  1.00  5.28      FRAP
ATOM   1586  HZ1  LYS  2066     -16.491  17.449   7.520  0.00  0.00      FRAP
ATOM   1587  HZ2  LYS  2066     -17.527  16.533   8.514  0.00  0.00      FRAP
ATOM   1588  HZ3  LYS  2066     -15.912  16.043   8.283  0.00  0.00      FRAP
ATOM   1589  C    LYS  2066     -21.072  20.317  12.070  1.00 11.53      FRAP
ATOM   1590  O    LYS  2066     -20.704  20.148  13.226  1.00 16.33      FRAP
ATOM   1591  N    GLU  2067     -21.548  21.479  11.646  1.00 14.92      FRAP
ATOM   1592  H    GLU  2067     -21.556  21.672  10.692  0.00  0.00      FRAP
ATOM   1593  CA   GLU  2067     -21.998  22.508  12.569  1.00 15.78      FRAP
ATOM   1594  CB   GLU  2067     -22.143  23.842  11.835  1.00 22.50      FRAP
ATOM   1595  CG   GLU  2067     -20.877  24.292  11.105  1.00 25.09      FRAP
ATOM   1596  CD   GLU  2067     -21.032  25.619  10.365  1.00 25.97      FRAP
ATOM   1597  OE1  GLU  2067     -22.161  26.174  10.309  1.00 16.81      FRAP
ATOM   1598  OE2  GLU  2067     -20.002  26.108   9.844  1.00 26.65      FRAP
ATOM   1599  C    GLU  2067     -23.336  22.108  13.173  1.00 19.42      FRAP
ATOM   1600  O    GLU  2067     -23.693  22.562  14.260  1.00 22.50      FRAP
```

Figure 4: A-33

```
ATOM   1601  N    THR  2068     -24.096  21.300  12.435  1.00 19.36      FRAP
ATOM   1602  H    THR  2068     -23.847  21.150  11.501  0.00  0.00      FRAP
ATOM   1603  CA   THR  2068     -25.345  20.731  12.940  1.00 18.73      FRAP
ATOM   1604  CB   THR  2068     -26.140  20.025  11.809  1.00 14.88      FRAP
ATOM   1605  OG1  THR  2068     -26.656  21.013  10.912  1.00 16.48      FRAP
ATOM   1606  HG1  THR  2068     -25.961  21.423  10.376  0.00  0.00      FRAP
ATOM   1607  CG2  THR  2068     -27.317  19.239  12.370  1.00 13.69      FRAP
ATOM   1608  C    THR  2068     -25.120  19.751  14.100  1.00 20.11      FRAP
ATOM   1609  O    THR  2068     -25.625  19.971  15.204  1.00 24.18      FRAP
ATOM   1610  N    SER  2069     -24.303  18.724  13.879  1.00 15.42      FRAP
ATOM   1611  H    SER  2069     -23.872  18.626  13.000  0.00  0.00      FRAP
ATOM   1612  CA   SER  2069     -24.066  17.701  14.898  1.00 11.92      FRAP
ATOM   1613  CB   SER  2069     -23.234  16.555  14.315  1.00  3.97      FRAP
ATOM   1614  OG   SER  2069     -21.951  16.993  13.917  1.00  2.00      FRAP
ATOM   1615  HG   SER  2069     -21.427  16.200  13.756  0.00  0.00      FRAP
ATOM   1616  C    SER  2069     -23.404  18.243  16.180  1.00 14.81      FRAP
ATOM   1617  O    SER  2069     -23.865  17.962  17.295  1.00 17.69      FRAP
ATOM   1618  N    PHE  2070     -22.371  19.070  16.018  1.00 12.68      FRAP
ATOM   1619  H    PHE  2070     -21.960  19.083  15.126  0.00  0.00      FRAP
ATOM   1620  CA   PHE  2070     -21.786  19.831  17.132  1.00  6.20      FRAP
ATOM   1621  CB   PHE  2070     -20.732  20.811  16.607  1.00  5.44      FRAP
ATOM   1622  CG   PHE  2070     -20.154  21.726  17.656  1.00  2.00      FRAP
ATOM   1623  CD1  PHE  2070     -18.861  21.521  18.130  1.00  2.00      FRAP
ATOM   1624  CD2  PHE  2070     -20.857  22.848  18.092  1.00  2.00      FRAP
ATOM   1625  CE1  PHE  2070     -18.272  22.419  19.016  1.00  2.00      FRAP
ATOM   1626  CE2  PHE  2070     -20.283  23.748  18.980  1.00  2.00      FRAP
ATOM   1627  CZ   PHE  2070     -18.985  23.534  19.441  1.00  2.00      FRAP
ATOM   1628  C    PHE  2070     -22.856  20.601  17.888  1.00  2.60      FRAP
ATOM   1629  O    PHE  2070     -22.752  20.790  19.082  1.00  7.27      FRAP
ATOM   1630  N    ASN  2071     -23.836  21.135  17.182  1.00  2.01      FRAP
ATOM   1631  H    ASN  2071     -23.831  21.076  16.202  0.00  0.00      FRAP
ATOM   1632  CA   ASN  2071     -24.876  21.880  17.851  1.00  2.00      FRAP
ATOM   1633  CB   ASN  2071     -25.689  22.675  16.841  1.00  7.02      FRAP
ATOM   1634  CG   ASN  2071     -26.604  23.677  17.501  1.00  8.30      FRAP
ATOM   1635  OD1  ASN  2071     -27.805  23.463  17.602  1.00 11.66      FRAP
ATOM   1636  ND2  ASN  2071     -26.035  24.766  17.987  1.00 12.66      FRAP
ATOM   1637  HD21 ASN  2071     -25.081  24.904  17.878  0.00  0.00      FRAP
ATOM   1638  HD22 ASN  2071     -26.665  25.370  18.419  0.00  0.00      FRAP
ATOM   1639  C    ASN  2071     -25.784  20.959  18.646  1.00  4.16      FRAP
ATOM   1640  O    ASN  2071     -26.258  21.328  19.711  1.00 10.87      FRAP
ATOM   1641  N    GLN  2072     -25.998  19.747  18.143  1.00  8.02      FRAP
ATOM   1642  H    GLN  2072     -25.642  19.564  17.247  0.00  0.00      FRAP
ATOM   1643  CA   GLN  2072     -26.801  18.741  18.845  1.00  8.00      FRAP
ATOM   1644  CB   GLN  2072     -27.061  17.554  17.934  1.00  2.00      FRAP
ATOM   1645  CG   GLN  2072     -28.010  17.884  16.798  1.00  6.79      FRAP
ATOM   1646  CD   GLN  2072     -27.941  16.881  15.665  1.00  8.96      FRAP
ATOM   1647  OE1  GLN  2072     -27.006  16.088  15.570  1.00  4.92      FRAP
ATOM   1648  NE2  GLN  2072     -28.940  16.908  14.798  1.00  6.99      FRAP
ATOM   1649  HE21 GLN  2072     -29.659  17.557  14.919  0.00  0.00      FRAP
ATOM   1650  HE22 GLN  2072     -28.875  16.258  14.072  0.00  0.00      FRAP
```

Figure 4: A-34

```
ATOM   1651  C    GLN  2072   -26.101  18.262  20.103  1.00  12.51      FRAP
ATOM   1652  O    GLN  2072   -26.693  18.224  21.178  1.00  19.60      FRAP
ATOM   1653  N    ALA  2073   -24.795  18.054  19.978  1.00  14.16      FRAP
ATOM   1654  H    ALA  2073   -24.426  18.142  19.081  0.00   0.00      FRAP
ATOM   1655  CA   ALA  2073   -23.940  17.625  21.077  1.00  14.24      FRAP
ATOM   1656  CB   ALA  2073   -22.583  17.223  20.518  1.00  15.34      FRAP
ATOM   1657  C    ALA  2073   -23.756  18.666  22.196  1.00  15.13      FRAP
ATOM   1658  O    ALA  2073   -24.013  18.383  23.369  1.00  18.26      FRAP
ATOM   1659  N    TYR  2074   -23.228  19.834  21.832  1.00  12.69      FRAP
ATOM   1660  H    TYR  2074   -23.091  19.988  20.874  0.00   0.00      FRAP
ATOM   1661  CA   TYR  2074   -22.791  20.842  22.796  1.00   8.11      FRAP
ATOM   1662  CB   TYR  2074   -21.330  21.206  22.547  1.00   3.13      FRAP
ATOM   1663  CG   TYR  2074   -20.444  20.034  22.216  1.00   8.31      FRAP
ATOM   1664  CD1  TYR  2074   -19.990  19.839  20.918  1.00  10.92      FRAP
ATOM   1665  CE1  TYR  2074   -19.160  18.772  20.591  1.00  12.41      FRAP
ATOM   1666  CD2  TYR  2074   -20.045  19.124  23.197  1.00  11.16      FRAP
ATOM   1667  CE2  TYR  2074   -19.205  18.050  22.882  1.00  12.75      FRAP
ATOM   1668  CZ   TYR  2074   -18.771  17.886  21.569  1.00  12.54      FRAP
ATOM   1669  OH   TYR  2074   -17.960  16.836  21.215  1.00  21.64      FRAP
ATOM   1670  HH   TYR  2074   -17.868  16.773  20.266  0.00   0.00      FRAP
ATOM   1671  C    TYR  2074   -23.618  22.128  22.804  1.00   8.66      FRAP
ATOM   1672  O    TYR  2074   -23.291  23.074  23.509  1.00   9.77      FRAP
ATOM   1673  N    GLY  2075   -24.714  22.153  22.063  1.00  10.37      FRAP
ATOM   1674  H    GLY  2075   -24.997  21.355  21.565  0.00   0.00      FRAP
ATOM   1675  CA   GLY  2075   -25.478  23.380  21.946  1.00  12.34      FRAP
ATOM   1676  C    GLY  2075   -26.130  23.796  23.246  1.00  17.07      FRAP
ATOM   1677  O    GLY  2075   -26.010  24.946  23.660  1.00  24.52      FRAP
ATOM   1678  N    ARG  2076   -26.770  22.843  23.921  1.00  19.49      FRAP
ATOM   1679  H    ARG  2076   -26.782  21.950  23.516  0.00   0.00      FRAP
ATOM   1680  CA   ARG  2076   -27.476  23.089  25.187  1.00  16.21      FRAP
ATOM   1681  CB   ARG  2076   -28.162  21.794  25.651  1.00  17.61      FRAP
ATOM   1682  CG   ARG  2076   -28.703  21.826  27.072  1.00  25.98      FRAP
ATOM   1683  CD   ARG  2076   -29.913  20.929  27.228  1.00  33.40      FRAP
ATOM   1684  NE   ARG  2076   -31.135  21.578  26.754  1.00  44.19      FRAP
ATOM   1685  HE   ARG  2076   -31.060  22.233  26.029  0.00   0.00      FRAP
ATOM   1686  CZ   ARG  2076   -32.351  21.341  27.241  1.00  50.69      FRAP
ATOM   1687  NH1  ARG  2076   -33.396  22.014  26.769  1.00  53.46      FRAP
ATOM   1688  HH11 ARG  2076   -33.274  22.698  26.051  0.00   0.00      FRAP
ATOM   1689  HH12 ARG  2076   -34.308  21.839  27.144  0.00   0.00      FRAP
ATOM   1690  NH2  ARG  2076   -32.532  20.415  28.180  1.00  51.70      FRAP
ATOM   1691  HH21 ARG  2076   -31.750  19.895  28.525  0.00   0.00      FRAP
ATOM   1692  HH22 ARG  2076   -33.446  20.249  28.551  0.00   0.00      FRAP
ATOM   1693  C    ARG  2076   -26.574  23.640  26.305  1.00  11.79      FRAP
ATOM   1694  O    ARG  2076   -26.861  24.680  26.885  1.00  11.52      FRAP
ATOM   1695  N    ASP  2077   -25.490  22.936  26.604  1.00   8.15      FRAP
ATOM   1696  H    ASP  2077   -25.346  22.086  26.144  0.00   0.00      FRAP
ATOM   1697  CA   ASP  2077   -24.526  23.394  27.594  1.00   6.48      FRAP
ATOM   1698  CB   ASP  2077   -23.332  22.448  27.637  1.00   5.61      FRAP
ATOM   1699  CG   ASP  2077   -23.615  21.196  28.425  1.00  10.00      FRAP
ATOM   1700  OD1  ASP  2077   -24.726  21.096  28.999  1.00   9.97      FRAP
```

Figure 4: A-35

```
ATOM   1701  OD2 ASP  2077     -22.724  20.317  28.479  1.00 12.06      FRAP
ATOM   1702  C   ASP  2077     -24.035  24.809  27.331  1.00  8.55      FRAP
ATOM   1703  O   ASP  2077     -24.126  25.669  28.201  1.00 13.05      FRAP
ATOM   1704  N   LEU  2078     -23.544  25.058  26.123  1.00  6.49      FRAP
ATOM   1705  H   LEU  2078     -23.477  24.330  25.469  0.00  0.00      FRAP
ATOM   1706  CA  LEU  2078     -23.064  26.386  25.752  1.00  4.74      FRAP
ATOM   1707  CB  LEU  2078     -22.495  26.364  24.333  1.00  3.18      FRAP
ATOM   1708  CG  LEU  2078     -21.161  25.653  24.084  1.00  2.91      FRAP
ATOM   1709  CD1 LEU  2078     -20.928  25.574  22.593  1.00  2.37      FRAP
ATOM   1710  CD2 LEU  2078     -20.010  26.387  24.764  1.00  2.00      FRAP
ATOM   1711  C   LEU  2078     -24.146  27.466  25.862  1.00  4.72      FRAP
ATOM   1712  O   LEU  2078     -23.847  28.626  26.118  1.00  2.64      FRAP
ATOM   1713  N   MET  2079     -25.401  27.091  25.651  1.00  7.76      FRAP
ATOM   1714  H   MET  2079     -25.579  26.181  25.326  0.00  0.00      FRAP
ATOM   1715  CA  MET  2079     -26.507  28.022  25.850  1.00 14.65      FRAP
ATOM   1716  CB  MET  2079     -27.803  27.434  25.295  1.00 18.67      FRAP
ATOM   1717  CG  MET  2079     -28.999  28.367  25.363  1.00 25.96      FRAP
ATOM   1718  SD  MET  2079     -29.718  28.677  23.724  1.00 40.57      FRAP
ATOM   1719  CE  MET  2079     -30.358  27.004  23.294  1.00 36.64      FRAP
ATOM   1720  C   MET  2079     -26.686  28.344  27.330  1.00 17.59      FRAP
ATOM   1721  O   MET  2079     -26.714  29.505  27.716  1.00 21.68      FRAP
ATOM   1722  N   GLU  2080     -26.769  27.308  28.158  1.00 18.54      FRAP
ATOM   1723  H   GLU  2080     -26.733  26.408  27.770  0.00  0.00      FRAP
ATOM   1724  CA  GLU  2080     -26.928  27.477  29.599  1.00 18.17      FRAP
ATOM   1725  CB  GLU  2080     -27.006  26.111  30.286  1.00 24.46      FRAP
ATOM   1726  CG  GLU  2080     -27.581  26.144  31.708  1.00 33.04      FRAP
ATOM   1727  CD  GLU  2080     -27.199  24.914  32.530  1.00 37.28      FRAP
ATOM   1728  OE1 GLU  2080     -26.827  25.080  33.714  1.00 39.48      FRAP
ATOM   1729  OE2 GLU  2080     -27.253  23.783  31.991  1.00 40.40      FRAP
ATOM   1730  C   GLU  2080     -25.773  28.284  30.191  1.00 16.44      FRAP
ATOM   1731  O   GLU  2080     -25.995  29.230  30.940  1.00 17.68      FRAP
ATOM   1732  N   ALA  2081     -24.555  27.981  29.756  1.00 15.30      FRAP
ATOM   1733  H   ALA  2081     -24.449  27.180  29.211  0.00  0.00      FRAP
ATOM   1734  CA  ALA  2081     -23.375  28.743  30.149  1.00 12.75      FRAP
ATOM   1735  CB  ALA  2081     -22.163  28.263  29.373  1.00  8.47      FRAP
ATOM   1736  C   ALA  2081     -23.591  30.233  29.912  1.00 14.17      FRAP
ATOM   1737  O   ALA  2081     -23.284  31.057  30.767  1.00 17.02      FRAP
ATOM   1738  N   GLN  2082     -24.253  30.560  28.809  1.00 16.91      FRAP
ATOM   1739  H   GLN  2082     -24.566  29.833  28.233  0.00  0.00      FRAP
ATOM   1740  CA  GLN  2082     -24.557  31.948  28.477  1.00 18.00      FRAP
ATOM   1741  CB  GLN  2082     -25.085  32.032  27.048  1.00 22.74      FRAP
ATOM   1742  CG  GLN  2082     -25.879  33.280  26.739  1.00 26.79      FRAP
ATOM   1743  CD  GLN  2082     -26.176  33.408  25.268  1.00 31.68      FRAP
ATOM   1744  OE1 GLN  2082     -25.360  33.930  24.509  1.00 29.64      FRAP
ATOM   1745  NE2 GLN  2082     -27.299  32.846  24.838  1.00 31.52      FRAP
ATOM   1746  HE21 GLN 2082     -27.890  32.386  25.460  0.00  0.00      FRAP
ATOM   1747  HE22 GLN 2082     -27.467  32.967  23.886  0.00  0.00      FRAP
ATOM   1748  C   GLN  2082     -25.558  32.584  29.439  1.00 17.54      FRAP
ATOM   1749  O   GLN  2082     -25.442  33.759  29.768  1.00 19.50      FRAP
ATOM   1750  N   GLU  2083     -26.551  31.819  29.875  1.00 18.34      FRAP
```

Figure 4: A-36

```
ATOM   1751   H     GLU  2083    -26.603  30.892  29.552  0.00   0.00   FRAP
ATOM   1752   CA    GLU  2083    -27.523  32.342  30.826  1.00  19.36   FRAP
ATOM   1753   CB    GLU  2083    -28.680  31.362  31.021  1.00  26.08   FRAP
ATOM   1754   CG    GLU  2083    -29.802  31.897  31.915  1.00  40.13   FRAP
ATOM   1755   CD    GLU  2083    -30.388  33.226  31.428  1.00  46.90   FRAP
ATOM   1756   OE1   GLU  2083    -30.392  34.207  32.209  1.00  48.07   FRAP
ATOM   1757   OE2   GLU  2083    -30.878  33.280  30.279  1.00  52.86   FRAP
ATOM   1758   C     GLU  2083    -26.863  32.651  32.166  1.00  13.37   FRAP
ATOM   1759   O     GLU  2083    -27.102  33.701  32.747  1.00  17.15   FRAP
ATOM   1760   N     TRP  2084    -25.915  31.817  32.563  1.00   6.62   FRAP
ATOM   1761   H     TRP  2084    -25.769  30.992  32.047  0.00   0.00   FRAP
ATOM   1762   CA    TRP  2084    -25.139  32.069  33.761  1.00   3.33   FRAP
ATOM   1763   CB    TRP  2084    -24.190  30.914  34.037  1.00   5.07   FRAP
ATOM   1764   CG    TRP  2084    -24.879  29.734  34.575  1.00   6.00   FRAP
ATOM   1765   CD2   TRP  2084    -25.606  29.664  35.801  1.00  10.76   FRAP
ATOM   1766   CE2   TRP  2084    -26.292  28.433  35.807  1.00  14.65   FRAP
ATOM   1767   CE3   TRP  2084    -25.765  30.533  36.887  1.00   9.81   FRAP
ATOM   1768   CD1   TRP  2084    -25.110  28.564  33.924  1.00  10.88   FRAP
ATOM   1769   NE1   TRP  2084    -25.972  27.781  34.646  1.00  17.13   FRAP
ATOM   1770   HE1   TRP  2084    -26.397  26.972  34.309  0.00   0.00   FRAP
ATOM   1771   CZ2   TRP  2084    -27.129  28.050  36.853  1.00  14.61   FRAP
ATOM   1772   CZ3   TRP  2084    -26.597  30.156  37.923  1.00  11.54   FRAP
ATOM   1773   CH2   TRP  2084    -27.272  28.924  37.899  1.00  16.36   FRAP
ATOM   1774   C     TRP  2084    -24.348  33.355  33.677  1.00   4.82   FRAP
ATOM   1775   O     TRP  2084    -24.240  34.076  34.665  1.00  10.80   FRAP
ATOM   1776   N     CYS  2085    -23.760  33.625  32.514  1.00   7.15   FRAP
ATOM   1777   H     CYS  2085    -23.725  32.895  31.856  0.00   0.00   FRAP
ATOM   1778   CA    CYS  2085    -23.062  34.894  32.274  1.00   7.94   FRAP
ATOM   1779   CB    CYS  2085    -22.329  34.868  30.935  1.00   2.21   FRAP
ATOM   1780   SG    CYS  2085    -20.748  34.024  30.993  1.00  14.42   FRAP
ATOM   1781   C     CYS  2085    -24.030  36.070  32.284  1.00  11.28   FRAP
ATOM   1782   O     CYS  2085    -23.718  37.138  32.813  1.00  13.68   FRAP
ATOM   1783   N     ARG  2086    -25.214  35.864  31.718  1.00  10.58   FRAP
ATOM   1784   H     ARG  2086    -25.382  35.014  31.259  0.00   0.00   FRAP
ATOM   1785   CA    ARG  2086    -26.250  36.878  31.749  1.00  11.82   FRAP
ATOM   1786   CB    ARG  2086    -27.476  36.405  30.970  1.00  16.71   FRAP
ATOM   1787   CG    ARG  2086    -27.279  36.429  29.458  1.00  22.27   FRAP
ATOM   1788   CD    ARG  2086    -28.160  35.398  28.768  1.00  36.61   FRAP
ATOM   1789   NE    ARG  2086    -29.300  35.986  28.060  1.00  45.02   FRAP
ATOM   1790   HE    ARG  2086    -29.553  36.906  28.280  0.00   0.00   FRAP
ATOM   1791   CZ    ARG  2086    -30.003  35.357  27.118  1.00  49.39   FRAP
ATOM   1792   NH1   ARG  2086    -31.021  35.971  26.523  1.00  48.26   FRAP
ATOM   1793   HH11  ARG  2086    -31.246  36.916  26.762  0.00   0.00   FRAP
ATOM   1794   HH12  ARG  2086    -31.538  35.499  25.809  0.00   0.00   FRAP
ATOM   1795   NH2   ARG  2086    -29.673  34.120  26.747  1.00  49.75   FRAP
ATOM   1796   HH21  ARG  2086    -28.913  33.645  27.190  0.00   0.00   FRAP
ATOM   1797   HH22  ARG  2086    -30.218  33.649  26.053  0.00   0.00   FRAP
ATOM   1798   C     ARG  2086    -26.618  37.180  33.193  1.00  11.93   FRAP
ATOM   1799   O     ARG  2086    -26.536  38.325  33.629  1.00  14.05   FRAP
ATOM   1800   N     LYS  2087    -26.792  36.120  33.976  1.00  14.39   FRAP
```

Figure 4: A-37

| | | | | | | | | | | |
|---|---|---|---|---|---|---|---|---|---|---|
| ATOM | 1801 | H | LYS | 2087 | -26.697 | 35.240 | 33.583 | 0.00 | 0.00 | FRAP |
| ATOM | 1802 | CA | LYS | 2087 | -27.104 | 36.240 | 35.401 | 1.00 | 11.99 | FRAP |
| ATOM | 1803 | CB | LYS | 2087 | -27.217 | 34.858 | 36.040 | 1.00 | 12.74 | FRAP |
| ATOM | 1804 | CG | LYS | 2087 | -28.510 | 34.139 | 35.778 | 1.00 | 13.98 | FRAP |
| ATOM | 1805 | CD | LYS | 2087 | -28.412 | 32.700 | 36.270 | 1.00 | 17.19 | FRAP |
| ATOM | 1806 | CE | LYS | 2087 | -29.760 | 31.998 | 36.220 | 1.00 | 26.67 | FRAP |
| ATOM | 1807 | NZ | LYS | 2087 | -29.640 | 30.517 | 36.341 | 1.00 | 33.46 | FRAP |
| ATOM | 1808 | HZ1 | LYS | 2087 | -29.184 | 30.284 | 37.245 | 0.00 | 0.00 | FRAP |
| ATOM | 1809 | HZ2 | LYS | 2087 | -29.051 | 30.158 | 35.561 | 0.00 | 0.00 | FRAP |
| ATOM | 1810 | HZ3 | LYS | 2087 | -30.581 | 30.076 | 36.301 | 0.00 | 0.00 | FRAP |
| ATOM | 1811 | C | LYS | 2087 | -26.038 | 37.041 | 36.144 | 1.00 | 9.73 | FRAP |
| ATOM | 1812 | O | LYS | 2087 | -26.356 | 37.859 | 37.000 | 1.00 | 12.76 | FRAP |
| ATOM | 1813 | N | TYR | 2088 | -24.771 | 36.803 | 35.821 | 1.00 | 7.02 | FRAP |
| ATOM | 1814 | H | TYR | 2088 | -24.578 | 36.057 | 35.209 | 0.00 | 0.00 | FRAP |
| ATOM | 1815 | CA | TYR | 2088 | -23.693 | 37.592 | 36.407 | 1.00 | 12.48 | FRAP |
| ATOM | 1816 | CB | TYR | 2088 | -22.327 | 37.135 | 35.892 | 1.00 | 9.00 | FRAP |
| ATOM | 1817 | CG | TYR | 2088 | -21.194 | 38.013 | 36.386 | 1.00 | 11.53 | FRAP |
| ATOM | 1818 | CD1 | TYR | 2088 | -20.780 | 37.953 | 37.712 | 1.00 | 13.53 | FRAP |
| ATOM | 1819 | CE1 | TYR | 2088 | -19.817 | 38.822 | 38.205 | 1.00 | 13.24 | FRAP |
| ATOM | 1820 | CD2 | TYR | 2088 | -20.603 | 38.967 | 35.553 | 1.00 | 9.73 | FRAP |
| ATOM | 1821 | CE2 | TYR | 2088 | -19.631 | 39.835 | 36.032 | 1.00 | 8.20 | FRAP |
| ATOM | 1822 | CZ | TYR | 2088 | -19.248 | 39.758 | 37.364 | 1.00 | 14.19 | FRAP |
| ATOM | 1823 | OH | TYR | 2088 | -18.308 | 40.621 | 37.881 | 1.00 | 21.06 | FRAP |
| ATOM | 1824 | HH | TYR | 2088 | -17.982 | 41.148 | 37.148 | 0.00 | 0.00 | FRAP |
| ATOM | 1825 | C | TYR | 2088 | -23.872 | 39.079 | 36.109 | 1.00 | 15.40 | FRAP |
| ATOM | 1826 | O | TYR | 2088 | -23.750 | 39.921 | 37.000 | 1.00 | 21.76 | FRAP |
| ATOM | 1827 | N | MET | 2089 | -24.238 | 39.383 | 34.870 | 1.00 | 14.77 | FRAP |
| ATOM | 1828 | H | MET | 2089 | -24.371 | 38.652 | 34.223 | 0.00 | 0.00 | FRAP |
| ATOM | 1829 | CA | MET | 2089 | -24.442 | 40.757 | 34.446 | 1.00 | 13.39 | FRAP |
| ATOM | 1830 | CB | MET | 2089 | -24.813 | 40.789 | 32.962 | 1.00 | 11.91 | FRAP |
| ATOM | 1831 | CG | MET | 2089 | -23.637 | 40.488 | 32.049 | 1.00 | 11.63 | FRAP |
| ATOM | 1832 | SD | MET | 2089 | -24.124 | 40.080 | 30.365 | 1.00 | 13.84 | FRAP |
| ATOM | 1833 | CE | MET | 2089 | -22.620 | 39.331 | 29.759 | 1.00 | 2.00 | FRAP |
| ATOM | 1834 | C | MET | 2089 | -25.500 | 41.475 | 35.272 | 1.00 | 11.34 | FRAP |
| ATOM | 1835 | O | MET | 2089 | -25.392 | 42.669 | 35.511 | 1.00 | 16.85 | FRAP |
| ATOM | 1836 | N | LYS | 2090 | -26.475 | 40.728 | 35.775 | 1.00 | 13.58 | FRAP |
| ATOM | 1837 | H | LYS | 2090 | -26.475 | 39.771 | 35.559 | 0.00 | 0.00 | FRAP |
| ATOM | 1838 | CA | LYS | 2090 | -27.591 | 41.322 | 36.506 | 1.00 | 17.01 | FRAP |
| ATOM | 1839 | CB | LYS | 2090 | -28.886 | 40.552 | 36.209 | 1.00 | 17.48 | FRAP |
| ATOM | 1840 | CG | LYS | 2090 | -29.218 | 39.436 | 37.207 | 1.00 | 30.54 | FRAP |
| ATOM | 1841 | CD | LYS | 2090 | -30.240 | 39.892 | 38.254 | 1.00 | 39.03 | FRAP |
| ATOM | 1842 | CE | LYS | 2090 | -30.140 | 39.078 | 39.545 | 1.00 | 40.52 | FRAP |
| ATOM | 1843 | NZ | LYS | 2090 | -30.477 | 39.893 | 40.756 | 1.00 | 38.43 | FRAP |
| ATOM | 1844 | HZ1 | LYS | 2090 | -31.451 | 40.248 | 40.672 | 0.00 | 0.00 | FRAP |
| ATOM | 1845 | HZ2 | LYS | 2090 | -29.826 | 40.700 | 40.829 | 0.00 | 0.00 | FRAP |
| ATOM | 1846 | HZ3 | LYS | 2090 | -30.396 | 39.308 | 41.612 | 0.00 | 0.00 | FRAP |
| ATOM | 1847 | C | LYS | 2090 | -27.371 | 41.420 | 38.023 | 1.00 | 18.18 | FRAP |
| ATOM | 1848 | O | LYS | 2090 | -28.022 | 42.230 | 38.695 | 1.00 | 16.27 | FRAP |
| ATOM | 1849 | N | SER | 2091 | -26.466 | 40.597 | 38.554 | 1.00 | 18.19 | FRAP |
| ATOM | 1850 | H | SER | 2091 | -25.955 | 40.047 | 37.923 | 0.00 | 0.00 | FRAP |

Figure 4: A-38

```
ATOM   1851  CA   SER  2091     -26.302  40.464  40.008  1.00  16.08      FRAP
ATOM   1852  CB   SER  2091     -26.662  39.051  40.465  1.00  15.61      FRAP
ATOM   1853  OG   SER  2091     -25.722  38.108  39.982  1.00  18.00      FRAP
ATOM   1854  HG   SER  2091     -26.010  37.832  39.096  0.00   0.00      FRAP
ATOM   1855  C    SER  2091     -24.917  40.794  40.537  1.00  14.61      FRAP
ATOM   1856  O    SER  2091     -24.761  41.071  41.724  1.00  16.95      FRAP
ATOM   1857  N    GLY  2092     -23.903  40.637  39.691  1.00  10.93      FRAP
ATOM   1858  H    GLY  2092     -24.107  40.356  38.784  0.00   0.00      FRAP
ATOM   1859  CA   GLY  2092     -22.536  40.883  40.117  1.00  12.47      FRAP
ATOM   1860  C    GLY  2092     -22.009  39.837  41.083  1.00  13.42      FRAP
ATOM   1861  O    GLY  2092     -20.913  39.974  41.622  1.00  11.96      FRAP
ATOM   1862  N    ASN  2093     -22.701  38.704  41.127  1.00  14.42      FRAP
ATOM   1863  H    ASN  2093     -23.481  38.626  40.514  0.00   0.00      FRAP
ATOM   1864  CA   ASN  2093     -22.465  37.664  42.114  1.00  15.72      FRAP
ATOM   1865  CB   ASN  2093     -23.572  36.626  42.021  1.00  15.84      FRAP
ATOM   1866  CG   ASN  2093     -23.884  35.977  43.353  1.00  16.87      FRAP
ATOM   1867  OD1  ASN  2093     -25.031  35.976  43.798  1.00  23.23      FRAP
ATOM   1868  ND2  ASN  2093     -22.879  35.381  43.975  1.00   9.23      FRAP
ATOM   1869  HD21 ASN  2093     -21.955  35.362  43.700  0.00   0.00      FRAP
ATOM   1870  HD22 ASN  2093     -23.187  35.027  44.822  0.00   0.00      FRAP
ATOM   1871  C    ASN  2093     -21.112  36.959  42.015  1.00  20.92      FRAP
ATOM   1872  O    ASN  2093     -20.599  36.466  43.015  1.00  28.74      FRAP
ATOM   1873  N    VAL  2094     -20.653  36.711  40.797  1.00  18.46      FRAP
ATOM   1874  H    VAL  2094     -21.105  37.113  40.045  0.00   0.00      FRAP
ATOM   1875  CA   VAL  2094     -19.386  36.003  40.528  1.00  19.15      FRAP
ATOM   1876  CB   VAL  2094     -18.134  36.636  41.223  1.00  17.65      FRAP
ATOM   1877  CG1  VAL  2094     -17.885  36.035  42.612  1.00  19.24      FRAP
ATOM   1878  CG2  VAL  2094     -16.911  36.422  40.333  1.00  22.37      FRAP
ATOM   1879  C    VAL  2094     -19.390  34.508  40.807  1.00  17.55      FRAP
ATOM   1880  O    VAL  2094     -18.534  33.779  40.311  1.00  20.43      FRAP
ATOM   1881  N    LYS  2095     -20.415  34.016  41.485  1.00  16.99      FRAP
ATOM   1882  H    LYS  2095     -20.859  34.593  42.164  0.00   0.00      FRAP
ATOM   1883  CA   LYS  2095     -20.615  32.570  41.511  1.00  19.09      FRAP
ATOM   1884  CB   LYS  2095     -21.166  32.125  42.869  1.00  24.46      FRAP
ATOM   1885  CG   LYS  2095     -20.193  31.221  43.633  1.00  33.72      FRAP
ATOM   1886  CD   LYS  2095     -18.736  31.682  43.507  1.00  32.25      FRAP
ATOM   1887  CE   LYS  2095     -17.771  30.625  44.033  1.00  37.61      FRAP
ATOM   1888  NZ   LYS  2095     -17.512  29.527  43.054  1.00  34.92      FRAP
ATOM   1889  HZ1  LYS  2095     -17.131  29.930  42.177  0.00   0.00      FRAP
ATOM   1890  HZ2  LYS  2095     -18.395  29.025  42.842  0.00   0.00      FRAP
ATOM   1891  HZ3  LYS  2095     -16.816  28.873  43.458  0.00   0.00      FRAP
ATOM   1892  C    LYS  2095     -21.515  32.087  40.378  1.00  16.91      FRAP
ATOM   1893  O    LYS  2095     -21.621  30.893  40.110  1.00  15.63      FRAP
ATOM   1894  N    ASP  2096     -22.168  33.029  39.710  1.00  14.55      FRAP
ATOM   1895  H    ASP  2096     -22.269  33.893  40.141  0.00   0.00      FRAP
ATOM   1896  CA   ASP  2096     -22.850  32.737  38.459  1.00  11.12      FRAP
ATOM   1897  CB   ASP  2096     -23.799  33.868  38.099  1.00  12.16      FRAP
ATOM   1898  CG   ASP  2096     -24.973  33.956  39.042  1.00  14.76      FRAP
ATOM   1899  OD1  ASP  2096     -25.630  32.925  39.259  1.00  18.49      FRAP
ATOM   1900  OD2  ASP  2096     -25.238  35.055  39.567  1.00  24.14      FRAP
```

Figure 4: A-39

```
ATOM   1901  C    ASP  2096    -21.837  32.538  37.339  1.00  10.59      FRAP
ATOM   1902  O    ASP  2096    -21.903  31.563  36.590  1.00  13.81      FRAP
ATOM   1903  N    LEU  2097    -20.816  33.386  37.326  1.00   7.24      FRAP
ATOM   1904  H    LEU  2097    -20.814  34.129  37.956  0.00   0.00      FRAP
ATOM   1905  CA   LEU  2097    -19.723  33.244  36.383  1.00   7.03      FRAP
ATOM   1906  CB   LEU  2097    -18.701  34.357  36.591  1.00   2.85      FRAP
ATOM   1907  CG   LEU  2097    -18.252  35.073  35.317  1.00   7.43      FRAP
ATOM   1908  CD1  LEU  2097    -19.451  35.345  34.428  1.00   2.68      FRAP
ATOM   1909  CD2  LEU  2097    -17.543  36.371  35.661  1.00   6.68      FRAP
ATOM   1910  C    LEU  2097    -19.056  31.873  36.504  1.00  12.75      FRAP
ATOM   1911  O    LEU  2097    -18.854  31.190  35.499  1.00  17.71      FRAP
ATOM   1912  N    THR  2098    -18.847  31.410  37.735  1.00  13.89      FRAP
ATOM   1913  H    THR  2098    -19.017  31.985  38.512  0.00   0.00      FRAP
ATOM   1914  CA   THR  2098    -18.266  30.082  37.954  1.00  14.50      FRAP
ATOM   1915  CB   THR  2098    -17.866  29.853  39.429  1.00  18.86      FRAP
ATOM   1916  OG1  THR  2098    -18.952  30.231  40.288  1.00  27.76      FRAP
ATOM   1917  HG1  THR  2098    -19.663  29.576  40.325  0.00   0.00      FRAP
ATOM   1918  CG2  THR  2098    -16.624  30.666  39.781  1.00  14.88      FRAP
ATOM   1919  C    THR  2098    -19.187  28.940  37.521  1.00  14.65      FRAP
ATOM   1920  O    THR  2098    -18.733  27.967  36.924  1.00  20.42      FRAP
ATOM   1921  N    GLN  2099    -20.486  29.070  37.772  1.00  13.41      FRAP
ATOM   1922  H    GLN  2099    -20.807  29.834  38.297  0.00   0.00      FRAP
ATOM   1923  CA   GLN  2099    -21.443  28.076  37.293  1.00  10.97      FRAP
ATOM   1924  CB   GLN  2099    -22.843  28.371  37.838  1.00  19.13      FRAP
ATOM   1925  CG   GLN  2099    -23.423  27.264  38.720  1.00  26.63      FRAP
ATOM   1926  CD   GLN  2099    -23.315  25.887  38.084  1.00  33.37      FRAP
ATOM   1927  OE1  GLN  2099    -22.604  25.017  38.580  1.00  35.83      FRAP
ATOM   1928  NE2  GLN  2099    -23.989  25.697  36.959  1.00  38.47      FRAP
ATOM   1929  HE21 GLN  2099    -24.521  26.407  36.558  0.00   0.00      FRAP
ATOM   1930  HE22 GLN  2099    -23.848  24.808  36.587  0.00   0.00      FRAP
ATOM   1931  C    GLN  2099    -21.478  28.072  35.768  1.00   9.33      FRAP
ATOM   1932  O    GLN  2099    -21.842  27.085  35.147  1.00  13.05      FRAP
ATOM   1933  N    ALA  2100    -21.146  29.211  35.178  1.00   9.52      FRAP
ATOM   1934  H    ALA  2100    -21.074  30.018  35.723  0.00   0.00      FRAP
ATOM   1935  CA   ALA  2100    -21.016  29.323  33.738  1.00   3.77      FRAP
ATOM   1936  CB   ALA  2100    -20.953  30.796  33.348  1.00   2.00      FRAP
ATOM   1937  C    ALA  2100    -19.760  28.586  33.277  1.00   2.86      FRAP
ATOM   1938  O    ALA  2100    -19.823  27.736  32.394  1.00   2.63      FRAP
ATOM   1939  N    TRP  2101    -18.659  28.801  33.988  1.00   2.00      FRAP
ATOM   1940  H    TRP  2101    -18.717  29.421  34.743  0.00   0.00      FRAP
ATOM   1941  CA   TRP  2101    -17.367  28.222  33.627  1.00   3.21      FRAP
ATOM   1942  CB   TRP  2101    -16.263  29.010  34.300  1.00   3.18      FRAP
ATOM   1943  CG   TRP  2101    -15.704  30.029  33.420  1.00   4.37      FRAP
ATOM   1944  CD2  TRP  2101    -15.003  29.798  32.198  1.00   5.80      FRAP
ATOM   1945  CE2  TRP  2101    -14.676  31.057  31.662  1.00   7.80      FRAP
ATOM   1946  CE3  TRP  2101    -14.625  28.646  31.500  1.00   5.41      FRAP
ATOM   1947  CD1  TRP  2101    -15.775  31.378  33.581  1.00   5.99      FRAP
ATOM   1948  NE1  TRP  2101    -15.158  32.008  32.525  1.00  13.05      FRAP
ATOM   1949  HE1  TRP  2101    -15.113  32.979  32.395  0.00   0.00      FRAP
ATOM   1950  CZ2  TRP  2101    -13.993  31.197  30.456  1.00   6.76      FRAP
```

Figure 4: A-40

```
ATOM   1951  CZ3 TRP  2101     -13.951  28.786  30.301  1.00  3.13      FRAP
ATOM   1952  CH2 TRP  2101     -13.644  30.052  29.791  1.00  6.31      FRAP
ATOM   1953  C   TRP  2101     -17.206  26.736  33.960  1.00  8.69      FRAP
ATOM   1954  O   TRP  2101     -16.274  26.065  33.501  1.00 10.67      FRAP
ATOM   1955  N   ASP  2102     -18.091  26.240  34.807  1.00  8.35      FRAP
ATOM   1956  H   ASP  2102     -18.571  26.864  35.388  0.00  0.00      FRAP
ATOM   1957  CA  ASP  2102     -18.235  24.815  35.005  1.00  9.05      FRAP
ATOM   1958  CB  ASP  2102     -19.277  24.564  36.099  1.00 13.12      FRAP
ATOM   1959  CG  ASP  2102     -19.127  23.207  36.759  1.00 16.43      FRAP
ATOM   1960  OD1 ASP  2102     -20.084  22.779  37.436  1.00 23.14      FRAP
ATOM   1961  OD2 ASP  2102     -18.048  22.585  36.637  1.00 18.55      FRAP
ATOM   1962  C   ASP  2102     -18.688  24.180  33.686  1.00 10.27      FRAP
ATOM   1963  O   ASP  2102     -18.144  23.158  33.248  1.00 11.33      FRAP
ATOM   1964  N   LEU  2103     -19.646  24.828  33.029  1.00  8.01      FRAP
ATOM   1965  H   LEU  2103     -19.988  25.662  33.421  0.00  0.00      FRAP
ATOM   1966  CA  LEU  2103     -20.230  24.302  31.794  1.00  7.80      FRAP
ATOM   1967  CB  LEU  2103     -21.589  24.951  31.537  1.00  2.00      FRAP
ATOM   1968  CG  LEU  2103     -22.694  24.551  32.512  1.00  2.00      FRAP
ATOM   1969  CD1 LEU  2103     -23.659  25.697  32.675  1.00  2.04      FRAP
ATOM   1970  CD2 LEU  2103     -23.417  23.318  32.012  1.00  2.00      FRAP
ATOM   1971  C   LEU  2103     -19.314  24.486  30.577  1.00  7.45      FRAP
ATOM   1972  O   LEU  2103     -19.177  23.580  29.756  1.00  5.72      FRAP
ATOM   1973  N   TYR  2104     -18.594  25.602  30.530  1.00  6.39      FRAP
ATOM   1974  H   TYR  2104     -18.814  26.319  31.162  0.00  0.00      FRAP
ATOM   1975  CA  TYR  2104     -17.605  25.821  29.482  1.00  7.03      FRAP
ATOM   1976  CB  TYR  2104     -16.987  27.215  29.602  1.00  7.14      FRAP
ATOM   1977  CG  TYR  2104     -17.865  28.342  29.108  1.00  4.21      FRAP
ATOM   1978  CD1 TYR  2104     -18.003  29.508  29.852  1.00  7.88      FRAP
ATOM   1979  CE1 TYR  2104     -18.772  30.564  29.400  1.00  5.53      FRAP
ATOM   1980  CD2 TYR  2104     -18.535  28.256  27.888  1.00  2.00      FRAP
ATOM   1981  CE2 TYR  2104     -19.316  29.308  27.423  1.00  3.76      FRAP
ATOM   1982  CZ  TYR  2104     -19.419  30.462  28.187  1.00  8.86      FRAP
ATOM   1983  OH  TYR  2104     -20.122  31.548  27.727  1.00 12.11      FRAP
ATOM   1984  HH  TYR  2104     -20.693  31.333  27.011  0.00  0.00      FRAP
ATOM   1985  C   TYR  2104     -16.506  24.771  29.555  1.00  9.25      FRAP
ATOM   1986  O   TYR  2104     -16.102  24.216  28.536  1.00 12.91      FRAP
ATOM   1987  N   TYR  2105     -16.054  24.475  30.771  1.00 12.79      FRAP
ATOM   1988  H   TYR  2105     -16.371  25.002  31.536  0.00  0.00      FRAP
ATOM   1989  CA  TYR  2105     -15.030  23.452  30.996  1.00 10.70      FRAP
ATOM   1990  CB  TYR  2105     -14.680  23.376  32.481  1.00  7.06      FRAP
ATOM   1991  CG  TYR  2105     -13.496  22.488  32.765  1.00  4.50      FRAP
ATOM   1992  CD1 TYR  2105     -12.288  22.693  32.111  1.00  8.17      FRAP
ATOM   1993  CE1 TYR  2105     -11.184  21.892  32.360  1.00 12.33      FRAP
ATOM   1994  CD2 TYR  2105     -13.579  21.446  33.684  1.00  6.11      FRAP
ATOM   1995  CE2 TYR  2105     -12.472  20.629  33.946  1.00 12.32      FRAP
ATOM   1996  CZ  TYR  2105     -11.276  20.866  33.279  1.00 15.17      FRAP
ATOM   1997  OH  TYR  2105     -10.155  20.113  33.542  1.00 21.26      FRAP
ATOM   1998  HH  TYR  2105      -9.397  20.447  33.059  0.00  0.00      FRAP
ATOM   1999  C   TYR  2105     -15.479  22.070  30.515  1.00 10.02      FRAP
ATOM   2000  O   TYR  2105     -14.702  21.307  29.942  1.00 11.77      FRAP
```

Figure 4: A-41

```
ATOM   2001  N    HIS  2106    -16.746  21.759  30.737  1.00   9.87      FRAP
ATOM   2002  H    HIS  2106    -17.288  22.402  31.250  0.00   0.00      FRAP
ATOM   2003  CA   HIS  2106    -17.298  20.488  30.314  1.00  11.64      FRAP
ATOM   2004  CB   HIS  2106    -18.705  20.326  30.881  1.00  15.15      FRAP
ATOM   2005  CG   HIS  2106    -19.294  18.971  30.664  1.00  24.44      FRAP
ATOM   2006  CD2  HIS  2106    -20.529  18.588  30.259  1.00  25.83      FRAP
ATOM   2007  ND1  HIS  2106    -18.578  17.808  30.865  1.00  28.70      FRAP
ATOM   2008  HD1  HIS  2106    -17.628  17.736  31.114  0.00   0.00      FRAP
ATOM   2009  CE1  HIS  2106    -19.346  16.767  30.595  1.00  28.91      FRAP
ATOM   2010  NE2  HIS  2106    -20.535  17.214  30.226  1.00  31.03      FRAP
ATOM   2011  HE2  HIS  2106    -21.295  16.644  29.972  0.00   0.00      FRAP
ATOM   2012  C    HIS  2106    -17.315  20.332  28.787  1.00  14.72      FRAP
ATOM   2013  O    HIS  2106    -16.928  19.284  28.273  1.00  17.34      FRAP
ATOM   2014  N    VAL  2107    -17.768  21.355  28.062  1.00  13.33      FRAP
ATOM   2015  H    VAL  2107    -18.077  22.171  28.519  0.00   0.00      FRAP
ATOM   2016  CA   VAL  2107    -17.797  21.281  26.599  1.00  10.31      FRAP
ATOM   2017  CB   VAL  2107    -18.640  22.425  25.963  1.00   9.70      FRAP
ATOM   2018  CG1  VAL  2107    -20.082  22.296  26.372  1.00  11.91      FRAP
ATOM   2019  CG2  VAL  2107    -18.116  23.780  26.371  1.00  15.79      FRAP
ATOM   2020  C    VAL  2107    -16.384  21.294  26.009  1.00  10.92      FRAP
ATOM   2021  O    VAL  2107    -16.047  20.456  25.172  1.00  11.27      FRAP
ATOM   2022  N    PHE  2108    -15.518  22.127  26.576  1.00   9.62      FRAP
ATOM   2023  H    PHE  2108    -15.849  22.771  27.234  0.00   0.00      FRAP
ATOM   2024  CA   PHE  2108    -14.109  22.164  26.187  1.00   8.05      FRAP
ATOM   2025  CB   PHE  2108    -13.371  23.223  27.007  1.00   4.20      FRAP
ATOM   2026  CG   PHE  2108    -11.923  23.366  26.651  1.00   2.00      FRAP
ATOM   2027  CD1  PHE  2108    -11.519  24.292  25.702  1.00   4.15      FRAP
ATOM   2028  CD2  PHE  2108    -10.961  22.606  27.295  1.00   3.42      FRAP
ATOM   2029  CE1  PHE  2108    -10.170  24.461  25.396  1.00   8.79      FRAP
ATOM   2030  CE2  PHE  2108     -9.613  22.760  27.000  1.00   9.05      FRAP
ATOM   2031  CZ   PHE  2108     -9.214  23.692  26.045  1.00  12.56      FRAP
ATOM   2032  C    PHE  2108    -13.423  20.810  26.364  1.00   9.13      FRAP
ATOM   2033  O    PHE  2108    -12.685  20.368  25.493  1.00  10.33      FRAP
ATOM   2034  N    ARG  2109    -13.609  20.198  27.528  1.00  11.74      FRAP
ATOM   2035  H    ARG  2109    -14.125  20.671  28.212  0.00   0.00      FRAP
ATOM   2036  CA   ARG  2109    -13.001  18.905  27.832  1.00  12.27      FRAP
ATOM   2037  CB   ARG  2109    -13.358  18.476  29.256  1.00  18.36      FRAP
ATOM   2038  CG   ARG  2109    -12.193  18.477  30.239  1.00  32.13      FRAP
ATOM   2039  CD   ARG  2109    -11.939  17.082  30.819  1.00  43.37      FRAP
ATOM   2040  NE   ARG  2109    -13.169  16.442  31.297  1.00  53.59      FRAP
ATOM   2041  HE   ARG  2109    -13.738  16.951  31.910  0.00   0.00      FRAP
ATOM   2042  CZ   ARG  2109    -13.573  15.218  30.956  1.00  54.76      FRAP
ATOM   2043  NH1  ARG  2109    -14.732  14.754  31.413  1.00  54.90      FRAP
ATOM   2044 HH11  ARG  2109    -15.288  15.321  32.021  0.00   0.00      FRAP
ATOM   2045 HH12  ARG  2109    -15.033  13.832  31.173  0.00   0.00      FRAP
ATOM   2046  NH2  ARG  2109    -12.812  14.444  30.188  1.00  53.94      FRAP
ATOM   2047 HH21  ARG  2109    -11.931  14.776  29.851  0.00   0.00      FRAP
ATOM   2048 HH22  ARG  2109    -13.130  13.529  29.944  0.00   0.00      FRAP
ATOM   2049  C    ARG  2109    -13.454  17.829  26.849  1.00  11.58      FRAP
ATOM   2050  O    ARG  2109    -12.682  16.939  26.509  1.00  11.33      FRAP
```

Figure 4: A-42

```
ATOM   2051  N    ARG   2110    -14.710  17.911  26.412  1.00 10.43      FRAP
ATOM   2052  H    ARG   2110    -15.280  18.632  26.748  0.00  0.00      FRAP
ATOM   2053  CA   ARG   2110    -15.260  16.952  25.455  1.00 10.64      FRAP
ATOM   2054  CB   ARG   2110    -16.795  16.947  25.499  1.00 12.47      FRAP
ATOM   2055  CG   ARG   2110    -17.418  16.320  26.743  1.00 19.35      FRAP
ATOM   2056  CD   ARG   2110    -17.423  14.786  26.714  1.00 31.28      FRAP
ATOM   2057  NE   ARG   2110    -16.091  14.194  26.900  1.00 41.95      FRAP
ATOM   2058  HE   ARG   2110    -15.389  14.432  26.260  0.00  0.00      FRAP
ATOM   2059  CZ   ARG   2110    -15.762  13.332  27.865  1.00 41.41      FRAP
ATOM   2060  NH1  ARG   2110    -14.534  12.815  27.899  1.00 36.39      FRAP
ATOM   2061 HH11  ARG   2110    -13.866  13.068  27.201  0.00  0.00      FRAP
ATOM   2062 HH12  ARG   2110    -14.282  12.171  28.621  0.00  0.00      FRAP
ATOM   2063  NH2  ARG   2110    -16.633  13.017  28.820  1.00 36.79      FRAP
ATOM   2064 HH21  ARG   2110    -17.547  13.422  28.830  0.00  0.00      FRAP
ATOM   2065 HH22  ARG   2110    -16.368  12.373  29.538  0.00  0.00      FRAP
ATOM   2066  C    ARG   2110    -14.810  17.200  24.014  1.00 12.51      FRAP
ATOM   2067  O    ARG   2110    -14.818  16.280  23.209  1.00 15.19      FRAP
ATOM   2068  N    ILE   2111    -14.494  18.447  23.670  1.00 14.35      FRAP
ATOM   2069  H    ILE   2111    -14.598  19.149  24.342  0.00  0.00      FRAP
ATOM   2070  CA   ILE   2111    -14.033  18.769  22.314  1.00 18.50      FRAP
ATOM   2071  CB   ILE   2111    -14.644  20.117  21.784  1.00 14.09      FRAP
ATOM   2072  CG2  ILE   2111    -16.148  20.108  21.982  1.00 19.97      FRAP
ATOM   2073  CG1  ILE   2111    -14.044  21.333  22.500  1.00 13.58      FRAP
ATOM   2074  CD1  ILE   2111    -14.821  22.615  22.301  1.00  2.00      FRAP
ATOM   2075  C    ILE   2111    -12.510  18.791  22.163  1.00 22.21      FRAP
ATOM   2076  O    ILE   2111    -11.963  19.586  21.395  1.00 27.42      FRAP
ATOM   2077  N    SER   2112    -11.840  17.887  22.870  1.00 27.11      FRAP
ATOM   2078  H    SER   2112    -12.312  17.230  23.418  0.00  0.00      FRAP
ATOM   2079  CA   SER   2112    -10.410  17.634  22.673  1.00 32.50      FRAP
ATOM   2080  CB   SER   2112     -9.590  18.179  23.852  1.00 31.61      FRAP
ATOM   2081  OG   SER   2112     -9.589  19.601  23.899  1.00 28.34      FRAP
ATOM   2082  HG   SER   2112     -9.617  19.750  24.846  0.00  0.00      FRAP
ATOM   2083  C    SER   2112    -10.155  16.126  22.525  1.00 35.63      FRAP
ATOM   2084  O    SER   2112    -10.552  15.361  23.432  1.00 36.42      FRAP
ATOM   2085  OT   SER   2112     -9.613  15.712  21.474  1.00 41.38      FRAP
ATOM   2086  OH2  WATR   301    -13.963  32.282  39.005  1.00 20.07      WATR
ATOM   2087  H1   WATR   301    -14.436  33.059  39.326  0.00 20.00      WATR
ATOM   2088  H2   WATR   301    -13.909  31.701  39.771  0.00 20.00      WATR
ATOM   2089  OH2  WATR   302     -0.900  21.657  34.783  1.00 23.80      WATR
ATOM   2090  H1   WATR   302     -1.021  21.041  35.510  0.00 20.00      WATR
ATOM   2091  H2   WATR   302     -1.478  21.246  34.123  0.00 20.00      WATR
ATOM   2092  OH2  WATR   303     -6.938  34.185  40.131  1.00 41.17      WATR
ATOM   2093  H1   WATR   303     -6.199  34.542  39.638  0.00 20.00      WATR
ATOM   2094  H2   WATR   303     -6.527  33.918  40.941  0.00 20.00      WATR
ATOM   2095  OH2  WATR   304    -10.919  15.222  48.819  1.00 28.06      WATR
ATOM   2096  H1   WATR   304    -10.331  15.994  48.864  0.00 20.00      WATR
ATOM   2097  H2   WATR   304    -10.602  14.763  48.037  0.00 20.00      WATR
ATOM   2098  OH2  WATR   305    -21.400  35.769  26.707  1.00 26.77      WATR
ATOM   2099  H1   WATR   305    -21.139  35.329  27.513  0.00 20.00      WATR
ATOM   2100  H2   WATR   305    -22.356  35.778  26.710  0.00 20.00      WATR
```

Figure 4: A-43

```
ATOM   2101  OH2  WATR  306     0.813   27.087   37.460  1.00 15.38      WATR
ATOM   2102  H1   WATR  306     0.278   27.451   36.742  0.00 20.00      WATR
ATOM   2103  H2   WATR  306     0.156   26.516   37.895  0.00 20.00      WATR
ATOM   2104  OH2  WATR  307   -30.428   31.660   28.013  1.00 46.41      WATR
ATOM   2105  H1   WATR  307   -30.299   30.737   27.805  0.00 20.00      WATR
ATOM   2106  H2   WATR  307   -30.248   31.722   28.946  0.00 20.00      WATR
ATOM   2107  OH2  WATR  308    -4.519   32.837   47.558  1.00 15.92      WATR
ATOM   2108  H1   WATR  308    -4.435   32.964   48.515  0.00 20.00      WATR
ATOM   2109  H2   WATR  308    -4.287   31.920   47.465  0.00 20.00      WATR
ATOM   2110  OH2  WATR  309   -18.089   22.614   12.803  1.00 25.97      WATR
ATOM   2111  H1   WATR  309   -17.511   23.005   12.138  0.00 20.00      WATR
ATOM   2112  H2   WATR  309   -18.955   22.733   12.394  0.00 20.00      WATR
ATOM   2113  OH2  WATR  310   -22.152   21.619   36.180  1.00 41.59      WATR
ATOM   2114  H1   WATR  310   -22.437   22.341   36.738  0.00 20.00      WATR
ATOM   2115  H2   WATR  310   -22.872   21.464   35.569  0.00 20.00      WATR
ATOM   2116  OH2  WATR  311    -6.459    3.543   52.877  1.00 32.94      WATR
ATOM   2117  H1   WATR  311    -6.280    2.752   52.368  0.00 20.00      WATR
ATOM   2118  H2   WATR  311    -5.832    4.191   52.543  0.00 20.00      WATR
ATOM   2119  OH2  WATR  312    -5.993   11.471   28.804  1.00 18.59      WATR
ATOM   2120  H1   WATR  312    -6.909   11.725   28.881  0.00 20.00      WATR
ATOM   2121  H2   WATR  312    -5.782   11.031   29.653  0.00 20.00      WATR
ATOM   2122  OH2  WATR  313    -0.619   20.784   55.049  1.00 19.50      WATR
ATOM   2123  H1   WATR  313    -0.854   20.074   55.637  0.00 20.00      WATR
ATOM   2124  H2   WATR  313    -1.113   21.551   55.388  0.00 20.00      WATR
ATOM   2125  OH2  WATR  314    -5.598   26.321   58.876  1.00 36.20      WATR
ATOM   2126  H1   WATR  314    -6.497   26.108   58.602  0.00 20.00      WATR
ATOM   2127  H2   WATR  314    -5.118   25.491   58.861  0.00 20.00      WATR
ATOM   2128  OH2  WATR  315    -3.023   33.604   37.769  1.00 26.43      WATR
ATOM   2129  H1   WATR  315    -2.394   34.283   37.516  0.00 20.00      WATR
ATOM   2130  H2   WATR  315    -3.855   33.984   37.469  0.00 20.00      WATR
ATOM   2131  OH2  WATR  316   -25.006   29.561   22.950  1.00 41.75      WATR
ATOM   2132  H1   WATR  316   -24.532   29.047   23.605  0.00 20.00      WATR
ATOM   2133  H2   WATR  316   -25.677   28.934   22.652  0.00 20.00      WATR
ATOM   2134  OH2  WATR  317   -23.638   29.893   10.609  1.00 16.55      WATR
ATOM   2135  H1   WATR  317   -23.016   29.169   10.621  0.00 20.00      WATR
ATOM   2136  H2   WATR  317   -24.395   29.529   11.101  0.00 20.00      WATR
ATOM   2137  OH2  WATR  318    -7.744    6.880   50.272  1.00 20.83      WATR
ATOM   2138  H1   WATR  318    -7.080    6.901   49.564  0.00 20.00      WATR
ATOM   2139  H2   WATR  318    -7.480    6.116   50.785  0.00 20.00      WATR
ATOM   2140  OH2  WATR  319    -2.748    2.703   46.777  1.00 31.05      WATR
ATOM   2141  H1   WATR  319    -3.202    3.462   46.395  0.00 20.00      WATR
ATOM   2142  H2   WATR  319    -3.353    2.352   47.432  0.00 20.00      WATR
ATOM   2143  OH2  WATR  320   -19.295   42.654   40.303  1.00 39.42      WATR
ATOM   2144  H1   WATR  320   -19.042   41.825   39.876  0.00 20.00      WATR
ATOM   2145  H2   WATR  320   -18.638   43.269   39.991  0.00 20.00      WATR
ATOM   2146  OH2  WATR  321     0.583   32.369   55.901  1.00 39.29      WATR
ATOM   2147  H1   WATR  321    -0.191   32.008   55.428  0.00 20.00      WATR
ATOM   2148  H2   WATR  321     1.272   31.719   55.776  0.00 20.00      WATR
ATOM   2149  OH2  WATR  322   -16.781   17.874   51.246  1.00 33.48      WATR
ATOM   2150  H1   WATR  322   -17.172   18.545   50.688  0.00 20.00      WATR
```

Figure 4: A-44

```
ATOM   2151  H2   WATR  322    -15.838  18.064  51.228  0.00 20.00     WATR
ATOM   2152  OH2  WATR  323    -19.829  12.916  46.549  1.00 26.46     WATR
ATOM   2153  H1   WATR  323    -19.808  13.873  46.697  0.00 20.00     WATR
ATOM   2154  H2   WATR  323    -19.224  12.538  47.193  0.00 20.00     WATR
```

CRYSTALLINE FRAP COMPLEX

A portion of the disclosure of this patent document contains material which is subject to copyright protection. The copyright owner has no objection to the facsimile reproduction by anyone of the patent document or patent disclosure, as it appears in the Patent and Trademark Office patent file or records, but otherwise reserves all copyright rights whatsoever.

FIELD OF THE INVENTION

The invention relates to a complex, in crystalline form, of two proteins, FKBP12 and the FRB domain of FRAP, in association with rapamycin, a small organic molecule to which the proteins bind. The crystalline form of this ternary complex is particularly useful for the determination of the three-dimensional structure of the complex at the atomic level. The three dimensional structure provides information useful for the design of pharmaceutical compositions which inhibit the biological function of proteins such as FRAP which contain an FRB domain, particularly those biological functions mediated by molecular interactions involving rapamycin or other compounds capable of binding to an FRB domain.

BACKGROUND

Rapamycin (sometimes called sirolimus) was first described in 1975 as an antifungal agent isolated from Streptomyces hygroscopicus (Vezina, 1975; Sehgal, 1975). In 1987, the structurally related compound FK506 (sometimes called tacrolimus) was characterized as a potent immunosuppressive agent (Tanaka, 1987), and shortly thereafter, rapamycin was also shown to have potent immunosuppressive activity. In spite of rapamycin's immunosuppressive activity and structural similarity to FK506, the two compounds suppress the immune response in completely different ways (Schreiber, 1992). FK506 inhibits the T cell receptor (TCR) signal and prevents activation of a resting helper T cell. Rapamycin inhibits the autocrine signaling pathway involving interleukin-2 (IL-2) and the IL-2 receptor (IL-2R). These latter signals commit the cell to a program of cell division by communicating with the components of the cell cycle machinery necessary for DNA replication.

Both FK506 and rapamycin are potentially useful in the treatment of human disease. FK506 has been approved by the FDA for use in treating the rejection of transplanted organs. A similar use has been envisioned for rapamycin, and its demonstrated activity in organ transplantation and autoimmune animal models indicate a high clinical potential. Rapamycin has been shown to have antitumor activity against B16 melanocarcinoma, colon 26 tumor, EM ependymoblastoma, CD8F1 mammary and colon 38 murine tumors (Sehgal, 1993). Rapamycin has also shown immunosuppressive activity in assays to measure prevention of development of autoimmune adjuvant arthritis, experimental allergic encephalomyelitis and autoimmune uveoretinitis in the rat (Sehgal, 1993).

The biological activity and structural novelty of both rapamycin and FK506 led to a search for their cellular target(s), and the target of both compounds was identified as the plentiful cytoplasmic protein FKBP12 (for FK506 binding protein) of 12 kDa molecular mass. Since FK506 and rapamycin bound to the same target (Kd of 0.4 and 0.2 nM, respectively) and affected different pathways, a new function was attributed to the FKBP12-ligand complex. This new function arises from the ability of FKBP12-FK506 and FKBP12-rapamycin complexes, but not the individual components, to bind to and inhibit still other protein targets. The FKBP12-FK506 complex inhibits the phosphatase activity of calcineurin, a crucial component of the TCR pathway. Calcineurin is a serine/threonine phosphatase also called PP2B. The FKBP12-rapamycin complex inhibits the IL-2R signal by binding to a large (289kDa) protein named FRAP in humans (Brown et al, 1994) or RAFT in rats (Sabatini et al, 1994; Chiu et al, 1994).

The structural basis for the tight binding of FK506 and rapamycin by FKBP12 has been investigated by both X-ray diffraction and NMR techniques (Clardy, 1995). In particular, high resolution X-ray structures are available for FKBP12-FK506 (1.4 Å resolution) and FKBP12-rapamycin (1.7 Å resolution) (Van Duyne et al, 1991; Van Duyne et al, 1991a; Van Duyne et al, 1993). These structures reveal, among other things, the fold of FKBP12, the atomic details of the hydrophobic binding pocket, and the details of how FK506 and rapamycin interact with the binding pocket. A structural analysis of the complex formed between FKBP12-FK506-calcineurin is also available (Griffith et al, 1995). That structure reveals how the portion of FK506 not involved in binding FKBP12 interacts with calcineurin and inhibits its phosphatase activity.

The biochemical characterization of FRAP, the target of the FKBP12-rapamycin complex, remains incomplete. The C-terminal domain resembles a phosphatidylinositol (PI) kinase, but to date no PI or protein kinase activity has been convincingly demonstrated. FRAP (RAFT, TOR) are members of a rapidly growing and important family of proteins that have been identified only recently (Zakian, 1995). ATM, TEL1, DNA-PK and MEC1 are some of the recently characterized members of this family of PIK-related kinases. (See e.g., Keith, 1995). ATM (for ataxia telngiectasia mutant) is responsible for a human autosomal hereditary disease characterized by cerebellar degeneration, progressive mental retardation, uneven gait, dilation of blood vessels, immune deficiencies, premature aging and a hundredfold increase in cancer susceptibility (Zakian, 1995). Persons who are heterozygous in ATM are believed to be at elevated risk for cancer. Mutations to TEL1 lead to abnormally short telomeres, and in conjunction with other mutations can lead to sensitivity to X-rays, UV radiation and hydroxyurea. DNA-PK is, as the name suggests, a DNA-dependent protein kinase that recognizes damaged DNA, and human cells without DNA-PK activity are radiation sensitive and repair deficient. MEC1 is required for both S-M and G2-M checkpoint progression as well as for meiotic recombination in yeast. Thus MEC1 is arguably the master checkpoint gene in yeast.

FRAP is a large protein (2549 amino acid residues), and only a small fraction can be involved in recognizing the FKBP12-rapamycin complex. Fortunately all of these residues are in one domain, and this domain, which is called the FKBP12-rapamycin binding (FRB) domain, is the protein used in this invention. It was identified through tryptic digests of FRAP and independently produced as an 11 kDa soluble protein (Chen et al, 1995)

Unfortunately, until now, three-dimensional structural details of the association of FKBP12-rapamycin with the FRB domain of FRAP have remained completely unknown. In the absence of such three-dimensional structural details, it has been impossible to design compounds based on that structure which would be capable of mimicking rapamycin's binding to the FRB domain. We have now obtained crystals of that ternary complex and have determined its three dimensional structure. With this information, it is now possible for the first time to rationally design compounds capable of binding to an FRB domain and mimicking the pharmacological activity of rapamycin. Such mimics may be used in place of rapamycin as immunosuppressive agents or in other pharmacological applications.

SUMMMARY OF THE INVENTION

This invention centers on the FRB domain of human FRAP and begins with obtaining crystals of human FKBP12-rapamycin-FRB of sufficient quality to determine the three dimensional (tertiary) structure of the complex by X-ray diffraction methods.

In considering our work, it should be appreciated that obtaining protein crystals in any case is a somewhat unpredictable art, especially in cases in which the practitioner lacks the guidance of prior successes in preparing and/or crystalizing any closely related proteins. Obtaining our first crystals of the ternary complex was therefore itself an unexpected result. In addition, our data represents the first detailed information available on the three dimensional structure of FRAP or of any of the PIK-related kinases and revealed an unpredicted array of surface features.

Our results are useful in a number of applications. As previously mentioned, the atomic details of how the FKBP12-rapamycin complex interacts with the FRB domain is essential for the structure-based design of rapamycin analogs. As noted above, rapamycin has several promising clinical indications, and improved rapamycin analogs would be useful therapeutic agents. This structure can be used as an essential starting point in predicting, via homology modeling, the structures of related proteins which contain homologous FRB domains, including other members of the PIK-related kinase family.

Furthermore, the structure shows—in atomic detail—how a small organic molecule, rapamycin, can be used to hold two proteins, FKBP12 and FRB, in close proximity. As such, this structure contains important lessons for the design of heterodimerizing agents.

Thus, the knowledge obtained concerning the FRB of FRAP can be used to model the tertiary structure of related proteins. By way of example, the structure of renin has been modeled using the tertiary structure of endothiapepsin as a starting point for the derivation. Model building of cercarial elastase and tophozoite cysteine protease were each built from known serine and cysteine proteases that have less than 35% sequence identity. The resultant models were used to design inhibitors in the low micromolar range. (*Proc. Natl. Acad. Sci.* 1993, 90, 3583). Furthermore, alternative methods of tertiary structure determination that do not rely on X-ray diffraction techniques and thus do not require crystallization of the protein, such as NMR techniques, are simplified if a model of the structure is available for refinement using the additional data gathered by the alternative technique. Thus, knowledge of the tertiary structure of the FRB region of FRAP provides a significant window to the structure of other proteins containing a homologous FRB domain, including the other PIK-related kinases.

Accordingly, one object of this invention is to provide a composition, in crystalline form, comprising a protein containing an FRB domain. The protein may have a bound ligand or may be part of a complex with a second protein molecule and a shared ligand. For instance, the crystalline composition may contain a complex containing a first protein having a peptide sequence derived or selected from that of an FKBP12 protein, e.g., human FKBP12; a second protein having a peptide sequence derived or selected from that of an FRB domain of a PIK-related kinase family member, e.g. the FRB domain of human FRAP; and a ligand such as rapamycin which is capable of binding to both proteins to form a ternary complex. Such a crystalline composition may contain one or more heavy atoms, e.g., one or more lead, mercury, gold and/or selenium atoms. Such a heavy atom derivative may be obtained, for example, by expressing a gene encoding the protein of interest under conditions permitting the incorporation of one or more heavy atom labels (e.g. as in the incorporation of selenomethionine), reacting the protein with a reagent capable of linking a heavy atom to the protein (e.g. trimethyl lead acetate) or soaking a substance containing a heavy atom into the crystals.

Preferred crystalline compositions of this invention are capable of diffracting x-rays to a resolution of better than about 3.5 Å, and more preferably to a resolution of 2.7 Å or better, and are useful for determining the three-dimensional structure of the material. (The smaller the number of angstroms, the better the resolution.)

Crystalline compositions of this invention specifically include those in which the crystals are characterized by the structural coordinates of the FRB protein set forth in the accompanying FIG. 4 or characterized by coordinates having a root mean square deviation therefrom, with respect to backbone atoms of amino acids listed in FIG. 4, of 1.5 Å or less. Furthermore, our crystalline compositions include crystals characterized by the structural coordinates of both the FRB and FKBP12 proteins set forth in FIG. 4, optionally including a molecule of rapamycin as defined structurally by the accompanying coordinates therefor.

Structural coordinates of a crystalline composition of this invention may be stored in a machine-readable form on a machine-readable storage medium, e.g. a computer hard drive, diskette, DAT tape, etc., for display as a three-dimensional shape or for other uses involving computer-assisted manipulation of, or computation based on, the structural coordinates or the three-dimensional structures they define. For example, data defining the three dimensional structure of a composition of this invention or a portion thereof containing an FRB domain-containing protein of the PIK-related kinase family, or portions or structurally similar homologues of such proteins, may be stored in a machine-readable storage medium, and may be displayed as a graphical three-dimensional representation of the protein structure, typically using a computer capable of reading the data from said storage medium and programmed with instructions for creating the representation from such data. This invention thus encompasses a machine, such as a computer, having a memory which contains data representing the structural coordinates of a crystalline composition of this invention, e.g. the coordinates set forth in FIG. 4, together with additional optional data and instructions for manipulating such data. Such data may be used for a variety of purposes, such as the elucidation of other related structures and drug discovery.

A first set of such machine readable data may be combined with a second set of machine-readable data using a machine programmed with instructions for using the first data set and the second data set to determine at least a portion of the coordinates corresponding to the second set of machine-readable data. For instance, the first set of data may comprise a Fourier transform of at least a portion of the coordinates for the complex set forth in FIG. 4, while the second data set may comprise X-ray diffraction data of a molecule or molecular complex.

More specifically, one of the objects of this invention is to provide three-dimensional structural information on the FRB domain of FRAP, of other members of the PIK-related kinase family which containg homologous FRB domains, and of homologs or variants thereof, preferably in association with a bound ligand or bound ligand:protein complex (such as FKBP12-rapamycin). To that end, we provide for the use of the structural coordinates of a crystalline composition of this invention, or portions thereof, to solve, e.g. by molecular replacement, the three dimensional structure of a crystalline form of another such protein, protein:ligand complex, or protein:ligand:protein complex. Doing so involves obtaining x-ray diffraction data for crystals of the protein or complex for which one wishes to determine the three dimensional structure. Then, one determines the three-dimensional structure of that protein or complex by analyzing the x-ray diffraction data using molecular replacement techniques with reference to the previous structural coordinates. As described in U.S. Pat. No. 5,353,236, for instance, molecular replacement uses a molecule having a known structure as a starting point to model the structure of an unknown crystalline sample. This technique is based on the principle that two molecules which have similar structures, orientations and positions in the unit cell diffract similarly. Molecular replacement involves positioning the known structure in the unit cell in the same location and orientation as the unknown structure. Once positioned, the atoms of the known structure in the unit cell are used to calculate the structure factors that would result from a hypothetical diffraction experiment. This involves rotating the known structure in the six dimensions (three angular and three spatial dimensions) until alignment of the known structure with the experimental data is achieved. This approximate structure can be fine-tuned to yield a more accurate and often higher resolution structure using various refinement techniques. For instance, the resultant model for the structure defined by the experimental data may be subjected to rigid body refinement in which the model is subjected to limited additional rotation in the six dimensions yielding positioning shifts of under about 5%. The refined model may then be further refined using other known refinement methods.

For example, one may use molecular replacement to exploit a set of coordinates such as set forth in FIG. 4 to determine the structure of a crystalline co-complex of the FRB domain, FKBP12 and a ligand other than rapamycin. Likewise one may use that same approach to determine the three dimensional structure of a complex of FKBP12, rapamycin and a protein containing a modified FRAP FRB domain or an FRB domain from a homolog of FRAP.

Another object of the invention is to provide a method for determining the three-dimensional structure of a protein containing an FRB domain, or a complex of the protein with a ligand therefor, using homology modeling techniques and structural coordinates for a composition of this invention. Homology modeling involves constructing a model of an unknown structure using structural coordinates of one or more related proteins, protein domains and/or subdomains. Homology modeling may be conducted by fitting common or homologous portions of the protein or peptide whose three dimensional structure is to be solved to the three dimensional structure of homologous structural elements. Homology modeling can include rebuilding part or all of a three dimensional structure with replacement of amino acids (or other components) by those of the related structure to be solved. The structural coordinates obtained for the related protein or complex may be stored, displayed, manipulated and otherwise used in like fashion as those for the ternary complex of FKBP12-rapamycin-FRB set forth in FIG. 4.

Crystalline compositions of this invention thus provide a starting material, and their three dimensional structure coordinates a point of reference, for use in solving the three-dimensional structure of other proteins containing an FRB domain homologous to that of FRAP, as well as complexes containing such a protein. Sequence similarity may be determined using any conventional similarity matrix. (See e.g. Dayhoff,1979; Greer, 1981; and Gonnet, 1992). Proteins containing at least one FRB domain having at least 15% peptide sequence identity or similarity with respect to our FRB, as determined by any of the approaches described above, are considered FRAP homologs for the purpose of this disclosure.

By way of further example, the three dimensional structure defined by the machine readable data for the FRB domain (with or without the FKBP12 component) may be computationally evaluated for its ability to associate with various chemical entities. The term "chemical entity", as used herein, refers to chemical compounds, complexes of at least two chemical compounds, and fragments of such compounds or complexes.

For instance, a first set of machine-readable data defining the 3-D structure of FRAP or a FRAP homolog, or a portion or complex thereof, is combined with a second set of machine-readable data defining the structure of a chemical entity or moiety of interest using a machine programmed with instructions for evaluating the ability of the chemical entity or moiety to associate with the FRAP or FRAP homolog protein or portion or complex thereof and/or the location and/or orientation of such association. Such methods provide insight into the location, orientation and energetics of association of protein surfaces with such chemical entities.

Chemical entities that are capable of mimicking rapamycin's ability to associate with FRAP or a FRAP homolog should share part or all of rapamycin's pharmacologic activities, e.g. immunosuppressive activity, but may be designed for more convenient or economical preparation, improved pharmacokinetics, reduced side effects, etc. Such chemical entities therefore include potential drug candidates.

The three dimensional structure defined by the data may be displayed in a graphical format permitting visual inspection of the structure, as well as visual inspection of the association of the protein component(s) with rapamycin or other chemical entities. Alternatively, more quantitative or computational methods may be used. For example, one method of this invention for evaluating the ability of a chemical entity to associate with any of the molecules or molecular complexes set forth herein comprises the steps of: (a) employing computational means to perform a fitting operation between the chemical entity and a binding pocket or other surface feature of the molecule or molecular complex; and (b) analyzing the results of said fitting operation to quantify the association between the chemical entity and the binding pocket.

This invention further provides for the use of the structural coordinates of a crystalline composition of this invention, or portions thereof, to identify reactive amino acids, such as cysteine residues, within the three-dimensional structure, preferably within or adjacent to a ligand binding site; to generate and visualize a molecular surface, such as a water-accessible surface or a surface comprising the space-filling van der Waals surface of all atoms; to calculate and visualize the size and shape of surface features of the protein or complex, e.g., ligand binding pockets; to locate potential H-bond donors and acceptors within the three-dimensional structure, preferably within or adjacent to a ligand binding site; to calculate regions of hydrophobicity and hydrophilicity within the three-dimensional structure, preferably within or adjacent to a ligand binding site; and to calculate and visualize regions on or adjacent to the protein surface of favorable interaction energies with respect to selected functional groups of interest (e.g. amino, hydroxyl, carboxyl, methylene, alkyl, alkenyl, aromatic carbon, aromatic rings, heteroaromatic rings, etc.). One may use the foregoing approaches for characterizing the FRB domain-containing protein and its interactions with moieties of potential ligands to design or select compounds capable of specific covalent attachment to reactive amino acids (e.g., cysteine) and to design or select compounds of complementary characteristics (e.g., size, shape, charge, hydrophobicity/hydrophilicity, ability to participate in hydrogen bonding, etc.) to surface features of the protein, a set of which may be preselected. Using the structural coordinates, one may also predict or calculate the orientation, binding constant or relative affinity of a given ligand to the protein in the complexed state, and use that information to design or select compounds of improved affinity.

In such cases, the structural coordinates of the FRAP or FRAP homolog protein, or portion or complex thereof, are entered in machine readable form into a machine programmed with instructions for carrying out the desired operation and containing any necessary additional data, e.g. data defining structural and/or functional characteristics of a potential ligand or moiety thereof, defining molecular characteristics of the various amino acids, etc.

One method of this invention provides for selecting from a database of chemical structures a compound capable of binding to FRAP or a FRAP homolog. The method starts with structural coordinates of a crystalline composition of the invention, e.g., coordinates defining the three dimensional structure of FRAP or a FRAP homolog or a portion thereof or a complex thereof. Points associated with that three dimensional structure are characterized with respect to the favorability of interactions with one or more functional groups. A database of chemical structures is then searched for candidate compounds containing one or more functional groups disposed for favorable interaction with the protein based on the prior characterization. Compounds having structures which best fit the points of favorable interaction with the three dimensional structure are thus identified.

It is often preferred, although not required, that such searching be conducted with the aid of a computer. In that case a first set of machine-readable data defining the 3D structure of a FRAP or FRAP homolog protein, or a portion or protein-ligand complex thereof, is combined with a second set of machine readable data defining one or more moieties or functional groups of interest, using a machine programmed with instructions for identifying preferred locations for favorable interaction between the functional group(s) and atoms of the protein. A third set of data, i.e. data defining the location(s) of favorable interaction between protein and functional group(s) is so generated. That third set of data is then combined with a fourth set of data defining the 3D structures of one or more chemical entities using a machine programmed with instructions for identifying chemical entities containing functional groups so disposed as to best fit the locations of their respective favorable interaction with the protein.

Compounds having the structures selected or designed by any of the foregoing means may be tested for their ability to bind to FRAP or a FRAP homolog, inhibit the binding of FRAP or a FRAP homolog to a natural or non-natural ligand therefor (e.g. FKBP12-rapamycin, in the case of FRAP), and/or inhibit a biological function mediated by FRAP or the FRAP homolog.

This invention also permits methods for designing a compound capable of binding to a FRAP or FRAP homolog based on the three dimensional structure of bound rapamycin. One such method involves graphically displaying a three-dimensional representation based on coordinates defining the three-dimensional structure of a FRAP or FRAP homolog protein or a portion thereof complexed with a ligand such as the FKBP12:rapamycin complex. Interactions between portions of ligand and protein are characterized in order to identify candidate moieties of the ligand for replacement. One or more portions of the ligand which interact with the protein may be replaced with substitute moieties selected from a knowledge base of one or more candidate substitute moieties, and/or moieties may be added to the ligand to permit additional interactions with the protein. Compounds first identified by any of the methods described herein are also encompassed by this invention.

BRIEF DESCRIPTION OF THE DRAWINGS

FIG. 4 are structural coordinates set forth in Protein Databank formate.

DETAILED DESCRIPTION OF THE INVENTION

Figure 1:
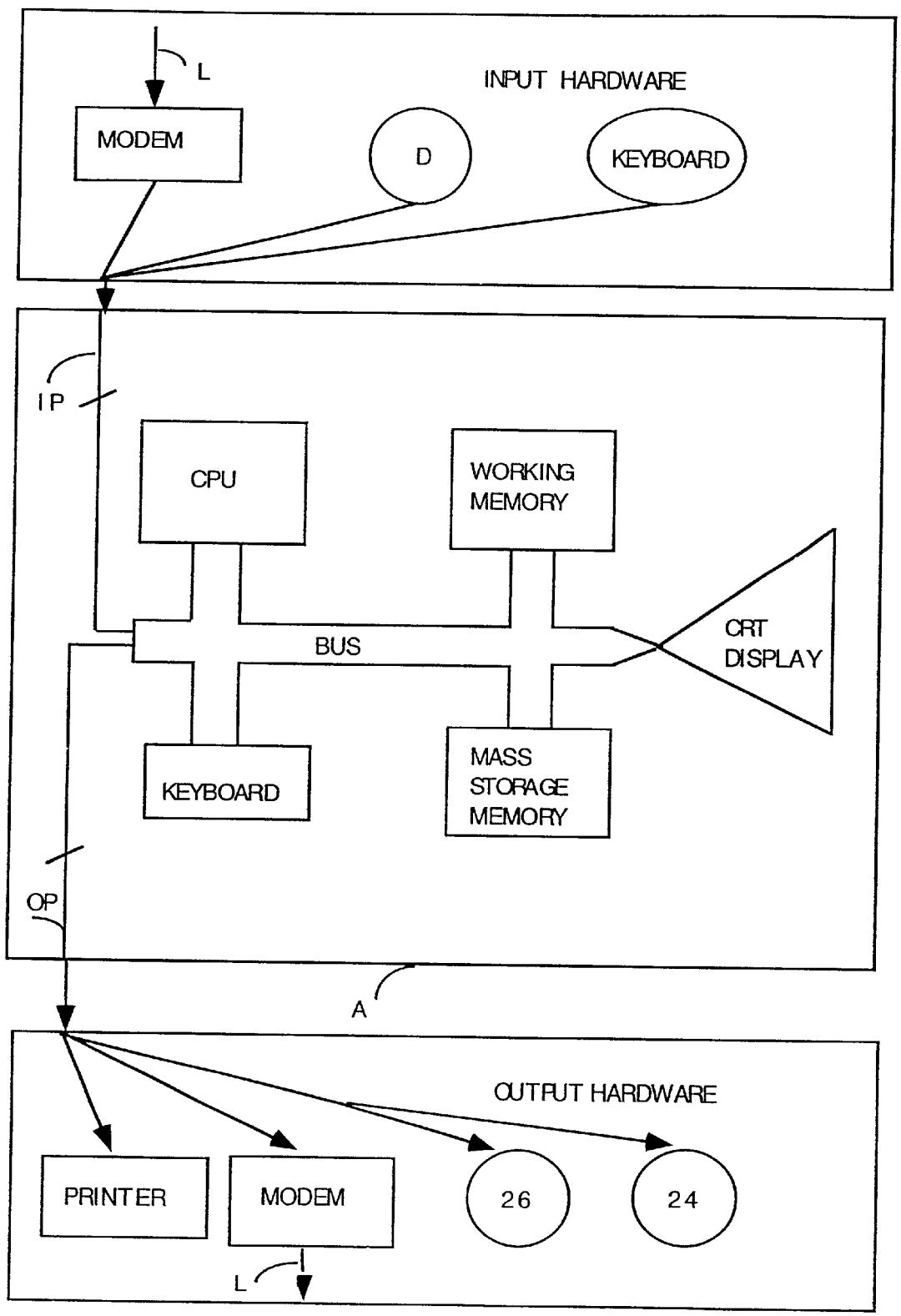
FIG. 1 depicts a computer system.

Despite the key role played by the FKBP12:rapamycin:FRAP complex in the IL-2/IL-2R signaling pathway, and despite the growing appreciation of the biological importance of the PIK-related kinase family, nothing was known of the three-dimensional architecture by which the FRB domain of FRAP (or of any FRAP homolog) engages the FKBP12:rapamycin complex required for its biological activity. X-ray crystallographic techniques could in principle address such issues. However, notwithstanding the key biological functions mediated by FRAP, there have been no reports disclosing that suitable crystals had been or could be obtained, let alone reports disclosing any x-ray crystallographic data or other information concerning the three-dimensional structure of any FRB domain. Even in the event that crystals had been obtained, then-available three-dimensional structural data relating to the FKBP12:rapamycin complex would not have been been sufficient for solving the ternary complex structure, at least in part, because the initial electron density maps wouldn't have permitted the chain of FRB to be traced. Even if parts of the chain could have been traced, they would not have refined under least-squares minimization techniques.

Nonetheless, we have succeeded in producing FKBP12 and FRAP FRB proteins, and have obtained crystals of their ternary complex with rapamycin. We have solved the three-dimensional structure of the crystalline complex using x-ray diffraction techniques. In view of our successes as disclosed herein, it can now be said that proteins comprising FRB domains can be produced in stable form, purified, and crystallized, and that their three-dimensional structures can be determined, all using materials and methods such as disclosed herein.

As mentioned elsewhere, FRAP is one of a number of PIK-related kinase family members that contain an FRB domain. PIK-related kinase family members share regions of homology including lipid kinase homologous regions, kinase domains and, in at least a number of cases, FRB domains. The presence and boundaries of homologous regions in a protein sequence can be identified by using a computer alignment program that identifies amino acid sequence homology to a known sequence or domain. For example, the FRB domain (amino acids 2015–2114) of FRAP may be used for such analysis, but FRB domains from other proteins such as RAPT or TOR1 or TOR2 can be used as well. The alignment method typically used by such programs is the Needleman-Wunch alignment. See e.g., "A General Method Applicable to the Search for Similarities in the Amino Acid Sequence of Two Proteins." Needlman, S. B.; Wunch, C. D. *J. Mol. Biol.* 1970, 48, 443–453.

We expressed the FRAP FRB domain as a glutathione-S-transferase (GST) fusion protein. The cDNA encoding residues 2015–2114 from human FRAP (Chen et al, 1995) was cloned into a pGEX vector and expressed in *E coli*, the resulting fusion protein was recovered and cleaved to yield the FRB protein which was then purified, all as described in detail below. FKBP12 protein was similarly obtained using a cDNA encoding residues 1-107 from human FKBP12 (Standaert et al, 1990, Nature 346: 671–674.

Other proteins containing an FRB domain may also be used, including larger FRAP fragments containing the FRB and flanking peptide sequence, including up to the entire FRAP protein. Additionally, FRB proteins can be prepared by analogous means containing homologous FRB regions from other proteins, including RAPT, TOR1, TOR2 or other members of the PIK-related kinase family. It should further be appreciated that other expression systems may be readily employed., including, e.g., materials and methods for expression in *E. coli* using T7, maltose-binding protein fusion (MBP), with epitope tags (His6, HA, myc, Flag) included or cleaved off. Baculoviral expression may be used, e.g. using pVL1393 or derivatives, for tFRB domain, fused (or not) to epitope tag or fusion partner such as GST. Conventional materials and methods for expression in mammalian, yeast or other cells may aiso be used.

Rapamycin may be prepared by known methods or may be obtained from commercial sources. Rapamycin analogs such as disclosed, e.g., in Luengo et al, 1995, Chemistry & Biology 2(7):471–481, may be used in place of rapamycin, in forming complexes of this invention.

Complex formation, crystallization, X ray diffraction experiments and interpretation of the diffraction data were conducted as described in detail in the Experimental Examples below. The resulting structural coordinates for a crystalline composition comprising FKBP12:rapamycin:FRB of FRAP (one molecule of complex per asymmetric unit) are set forth in Protein Database format in FIG. 4. Solving the X-ray crystal structure of the ternary complex allowed us to conduct the first three dimensional characterization of an FRB:ligand complex (viewing FKBP12:rapamycin as the "ligand"). The complex, depicted in schematic form in FIG. 3, involves an elaborate array of contacts between the two protein domains and their mutual small molecule ligand. This work reveals the first structural insights into an FRB domain-containing protein.

Structure of the Ternary Complex

The ternary complex of FKBP12-rapamycin-FRB has overall dimensions of 60 Å×45 Å×35 Å with the rapamycin sandwiched between FKBP12 and FRB. The FKBP12 structure is basically the same as in previously reported binary structures, with a five stranded anti parallel β-sheet and a short α-helix. This binary structure was originally determined in the FKBP12-FK506 complex and later in the FKBP12-rapamycin complex (Van Duyne et al, 1993). The four helix bundle of FRB does not wrap around the effector site of FKBP12-rapamycin; it just touches the effector (i.e., FRB-binding) interface of the binary complex with few protein-protein interactions. All of the interactions between rapamycin and FRB are hydrophobic interactions, and protein-protein interactions between FKBP12 and FRB are limited to the 80s loop and one side chain of the 40s loop of FKBP12 (Table 2). The solvent accessible surface areas of FKBP12 and FRB are 5348 Å$^2$ and 5711 Å$^2$, respectively. Since the solvent accessible surface area of the FKBP12-FRB complex (protein only) is 10342 Å$^2$, binding results in a very modest 6% reduction of solvent accessible surface area. Two long side chains in the 40s loop (Lys44 and Lys47) and three residues in the 80s loop (Thr85, Gly86 and His87) of FKBP12 appear to make crucial contact in the ternary complex. In the FRB site, two residues at the end of α1 and the α1–α2 loop (Arg2042 and Tyr2038) contact the 80s loop of FKBP12, and two residues in helix α4 (Tyr2105 and Asp2102) form direct or water-mediated hydrogen bonds to the 40s loop of FKBP12. The loop-loop interaction between 80s loop (FKBP12) and the α1–α2 loop (FRB) and the loop-helix interaction between 40s loop (FKBP12) and helix α4 are the main protein-protein interactions in this ternary complex and thus contribute all of the protein-protein binding force forming the ternary complex.

Structure of FRB domain of FRAP

The FRB domain of the FRAP forms a typical four helix bundle, which is one of the most common structural motifs in globular proteins. The overall dimensions of this domain are 45 Å×30 Å×30 Å. All four helices (termed α1–α4) are connected with short underhand loops. The longest helix α3 (residues 2065–2091) has a bend at residue 2074 of 59°. Except for a small bent part of α3 (residues 1065–2073), all four helices have similar lengths (16–19 residues, about 30 Å in length). The α2 helix also has a small bend around residues Glu2049, Val2050 and Leu2051 to form a $3_{10}$-helical turn rather than a normal α-helix. The angle between α1 and α2 is 22° and the angle between α3 and α4 is 20°. The angles between these pairs are in the range of 40–60°, which indicates that this four helix bundle is close to the 'X' type interhelical

TABLE 2

Intra-molecular hydrogen bonds and close contacts in the ternary complex

| Inter-helical interactions in the FRB domain of FRAP | | | | |
|---|---|---|---|---|
| | | | | Distance (Å) |
| His 2055 (α2) | Nε2 | Tyr 2104 (α4) | OH | 2.85 |
| His 2028 (α1) | Nε2 | Ser 2112 (C terminal) | Oγ | 3.23 |

| Close contacts of rapamycin and FRB domain of FRAP | | | |
|---|---|---|---|
| Rapamycin | FRB domain of FRAP | | Distance (Å) |
| C50 | Thr 2098 | O | 3.13 |
| C27 | Ser 2035 | Oγ | 3.39 |
| C51 | Ser 2035 | Oγ | 3.38 |

| Interactions of FKBP12 and FRB domain of FRAP | | | | |
|---|---|---|---|---|
| FKBP12 | | FRB domain of FRAP | | Distance (Å) |
| Lys 47 | O | Tyr 2105 | OH | 2.56 |
| Thr 85 | Oγ1 | Arg 2042 | NH1 | 3.10 |
| Thr 85 | Oγ1 | Arg 2042 | NH2 | 2.88 |

TABLE 2-continued

Intra-molecular hydrogen bonds and close contacts in the ternary complex

| Gly 86 | O | Arg 2042 | NH2 | 2.79 |
| His 87 | Nε2 | Tyr 2038 | OH | via H$_2$O 301 |
| His 87 | Nδ1 | Arg 2042 | NH2 | via H$_2$O 303 |
| Lys 44 | Nζ | Asp 2102 | Oδ1 | via H$_2$O 310 | pattern which is the alternating pattern of parallel and perpendicular helix-helix interactions (Harris et al, 1994). As usual, most of the hydrophobic and aromatic residues are located in the inter-helical interface and most of the hydrophilic residues are in the outside of the bundle, which is exposed to the solvent. Only two strong hydrogen bonds were found for the inter-helical interactions (Table 2) and could be key interactions maintaining the overall conformation of the four helix bundle. Helices α1 and α4, which have an interhelical angle of 44°, form a deep cleft on the molecular surface of this domain. This cleft is surrounded by six aromatic side chains forming the 'aromatic pocket' which has exquisite steric complementary for the rapamycin effector domain binding.

Structure of FKBP12-Rapamycin

The structure of FKBP12 in the ternary complex is basically the same as that in the binary complex of FKBP12-rapamycin or FKBP12-FK506. The protein fold and the architecture of the secondary structure are exactly the same as in the binary complex, and the interaction with rapamycin is also the same as that of the binary complex. The overall r.m.s. deviation between the FKBP12 in the ternary complex and that in the FKBP12-rapamycin complex is 1.14 Å (0.49 Å for the main chain), and the deviation between FKBP12 in the ternary complex and that in the FKBP12-FK506 complex is 1.11 Å (0.48 Å for the main chain), which implies that binding of FKBP12:rapamycin to the FRAP FRB domain is not accompanied by significant changes in the conformation of the FRB binding site on FKBP12 or of the effector domain of rapamycin. Even the 40s loop and 80s loop regions in the FKBP12, that have direct interaction to the FRB domain, are not significantly different in 3D structure from that seen in the binary complexes. These r.m.s. values were calculated by the rigid-body fitting on the main chain atoms in the FKBP12 using QUANTA. The overlay of FKBP12-FK506 to the ternary complex clearly confirmed the fact that FKBP12-FK506 complex can't bind FRAP as FK506's effector region does not extend enough. The protein-protein interactions by themselves between FKBP12 and FRB are not enough for the formation of a binary complex; rapamycin is essential to mediate the interaction of the two proteins.

FKBP12-Rapamycin binding to FRAP

While the interactions of rapamycin with FRB are all hydrophobic, rapamycin-FKBP12 interactions employ five hydrogen bonds which are the same found in the binary complex of FKBP12-rapamycin, to govern this interaction. Rapamycin is surrounded by five conserved aromatic residues in FKBP12, which makes the binding pocket for the rapamycin a complete 'aromatic pocket' along with six aromatic residues in FRB domain. Comparing the sequence of these aromatic residues of FRB domain with other FKBP-rapamycin target proteins, these six aromatic residues are all conserved in RAFT (Sabatini et al, 1994), TOR1, and TOR2 (Stan, et al, 1994)—suggesting that these structural results will be applicable to other members of the PIK-related kinase family. It is expected that binding domains of these other proteins have a similar structure with FRB domain. For the interaction between rapamycin and FRB domain, two major sites on FRB are considered crucial for rapamycin binding. Ser2035, which is also conserved in other FKBP12-rapamycin target proteins, has close contact with C27 and C51 of rapamycin (Table 2). The other site is Thr2098 which has a close contact with C50 of rapamycin. C50 of the rapamycin is at the end of C16 methoxy group, which has been a key target for substituted analogs. All of the hydrophobic interactions between rapamycin and FRB including Ser2035 and Thr2098 can be considered as the main force contributing to complete ternary complex.

Mutational Studies

Ser2035 in FRB has been the major site for the site-directed mutation studies of FRAP (Chen et al, 1995). Those studies revealed that the substitution of this residue to other residues larger than alanine abolish binding affinity toward FKBP12-rapamycin. The crystal structure of the ternary complex shows the direct effect of steric hindrance when this position is substituted by longer side chains. It has been suggested that this conserved serine site is a phosphorylation site, and phosphorylation would abrogate binding. By the binding of FKBP12-rapamycin, this serine site, which is open to the solvent when unbound, is protected from phosphorylation and this probably causes the inhibition of the downstream of the signaling pathway.

For rapamycin, C16 has been the main site for substitution in published structure-activity studies (Luengo et al, 1995). The studies of C16 analogs of rapamycin showed that the bulky group substitutions on this position have lower affinity for the FKBP12 binding and lower activity. However some analogs with different stereochemistry or different groups showed retained activity and affinity to FKBP12. Such C16 substituted analogs could be of therapeutic use.

Applications of the Invention

This invention encompasses crystalline compositions containing FRAP or a FRAP homolog protein or portion thereof, having a region characterized by structural coordinates of the FRB domain set forth in FIG. 4, or by coordinates having a root mean square deviation therefrom of less than about 1.5 Å, preferably less than about 1 Å, and even more preferably less than about 0.5 Å, with respect to backbone atoms of amino acid residues listed there.

As practitioners in this art will appreciate, various computational analyses may be used to determine the degree of similarity between the three dimensional structure of a given protein (or a portion or complex thereof) and FRAP or a FRAP homolog protein or portion (e.g. the FRB domain) or complex thereof such as are described herein. Such analyses may be carried out with commercially available software applications, such as the Molecular Similarity application of QUANTA (Molecular Simulations Inc., Waltham, Mass.) version 3.3, and as described in the accompanying User's Guide, Volume 3 pgs. 134–135.

The Molecular Similarity application permits comparisons between different structures, different conformations of the same structure, and different parts of the same structure. The procedure used in Molecular Similarity to compare structures is divided into four steps: (1) load the structures to be compared; (2) define the atom equivalences in these structures; (3) perform a fitting operation; and (4) analyze the results.

Each structure is identified by a name. One structure is identified as the target (i.e., the fixed structure); all remaining structures are working structures (i.e., moving structures). Since atom equivalency within QUANTA is defined by user input, for the purpose of this invention we define equivalent atoms as protein backbone atoms (N, Cα, C and O) for all conserved residues between the two structures being compared and consider only rigid fitting operations.

When a rigid fitting method is used, the working structure is translated and rotated to obtain an optimum fit with the target structure. The fitting operation uses a least squares fitting algorithm that computes the optimum translation and rotation to be applied to the moving structure, such that the root mean square difference of the fit over the specified pairs of equivalent atom is an absolute minimum. This number, given in angstroms, is reported by QUANTA.

For the purpose of this invention, any set of structural coordinates of a FRAP or FRAP homolog protein, portion of a FRAP or FRAP homolog protein or molecular complex thereof that has a root mean square deviation of conserved residue backbone atoms (N, Cα, C, O) of less than 1.5 Å when superimposed—using backbone atoms—on the relevant structural coordinates of a protein or complex of this invention, e.g. the coordinates listed in FIG. 4, are considered identical. More preferably, the root mean square deviation is less than 1.0 Å. Most preferably, the root mean square deviation is less than 0.5 Å.

The term "root mean square deviation" means the square root of the arithmetic mean of the squares of the deviations from the mean. It is a way to express the deviation or variation from a trend or object. For purposes of this invention, the "root mean square deviation" defines the variation in the backbone of a protein from the backbone of a protein of this invention, such as the FRB of FRAP, as defined by the structural coordinates of FIG. 4 and described herein.

The term "least squares" refers to a method based on the principle that the best estimate of a value is that in which the sum of the squares of the deviations of observed values is a minimum.

In order to use the structural coordinates generated for a crystalline substance of this invention, e.g. the structural coordinates of the FRB of FRAP set forth in FIG. 4, it is often necessary or desirable to display them as, or convert them to, a three-dimensional shape, or to otherwise manipulate them. This is typically accomplished by the use of commercially available software such as a program which is capable of generating three-dimensional graphical representations of molecules or portions thereof from a set of structural coordinates.

By way of illustration, a non-exclusive list of computer programs for viewing or otherwise manipulating protein structures include the following:
Midas (Univ. of California, San Francisco)
MidasPlus (Univ. of Cal., San Francisco)
MOIL (Univeristy of Illinois)
Yummie (Yale University)
Sybyl (Tripos, Inc.)
Insight/Discover (Biosym Technologies)
MacroModel (Columbia University)
Quanta (Molecular Simulations, Inc.)
Cerius (Molecular Simulations, Inc.)
Alchemy (Tripos, Inc.)
LabVision (Tripos, Inc.)
Rasmol (Glaxo Research and Development)
Ribbon (University of Alabama)
NAOMI (Oxford University)
Explorer Eyechem (Silicon Graphics, Inc.)
Univision (Cray Research)
Molscript (Uppsala University)
Chem-3D (Cambridge Scientific)
Chain (Baylor College of Medicine)
O (Uppsala University)
GRASP (Columbia University)
X-Plor
(Molecular Simulations, Inc.; Yale Univ.)
Spartan (Wavefunction, Inc.)
Catalyst (Molecular Simulations, Inc.)
Molcadd (Tripos, Inc.)
VMD (Univ.of Illinois/Beckman Institute)
Sculpt (Interactive Simulations, Inc.)
Procheck (Brookhaven Nat'l Laboratory)
DGEOM (QCPE)
RE_VIEW (Brunel University)
Modeller (Birbeck Col., Univ. of London)
Xmol (Minnesota Supercomputing Center)
Protein Expert (Cambridge Scientific)
HyperChem (Hypercube)
MD Display (University of Washington)
PKB
(Nat'l Center for Biotech. Info., NIH)
ChemX (Chemical Design, Ltd.)
Cameleon (Oxford Molecular, Inc.)
Iditis (Oxford Molecular, Inc.)

For storage, transfer and use with such programs of structural coordinates for a crystalline substance of this invention, a machine-readable storage medium is provided comprising a data storage material encoded with machine readable data which, when using a machine programmed with instructions for using said data, e.g. a computer loaded with one or more programs of the sort identified above, is capable of displaying a graphical three-dimensional representation of any of the molecules or molecular complexes described herein. Machine-readable storage media comprising a data storage material include conventional computer hard drives, floppy disks, DAT tape, CD-ROM, and other magnetic, magneto-optical, optical, floptical and other media which may be adapted for use with a computer.

Figure 3:
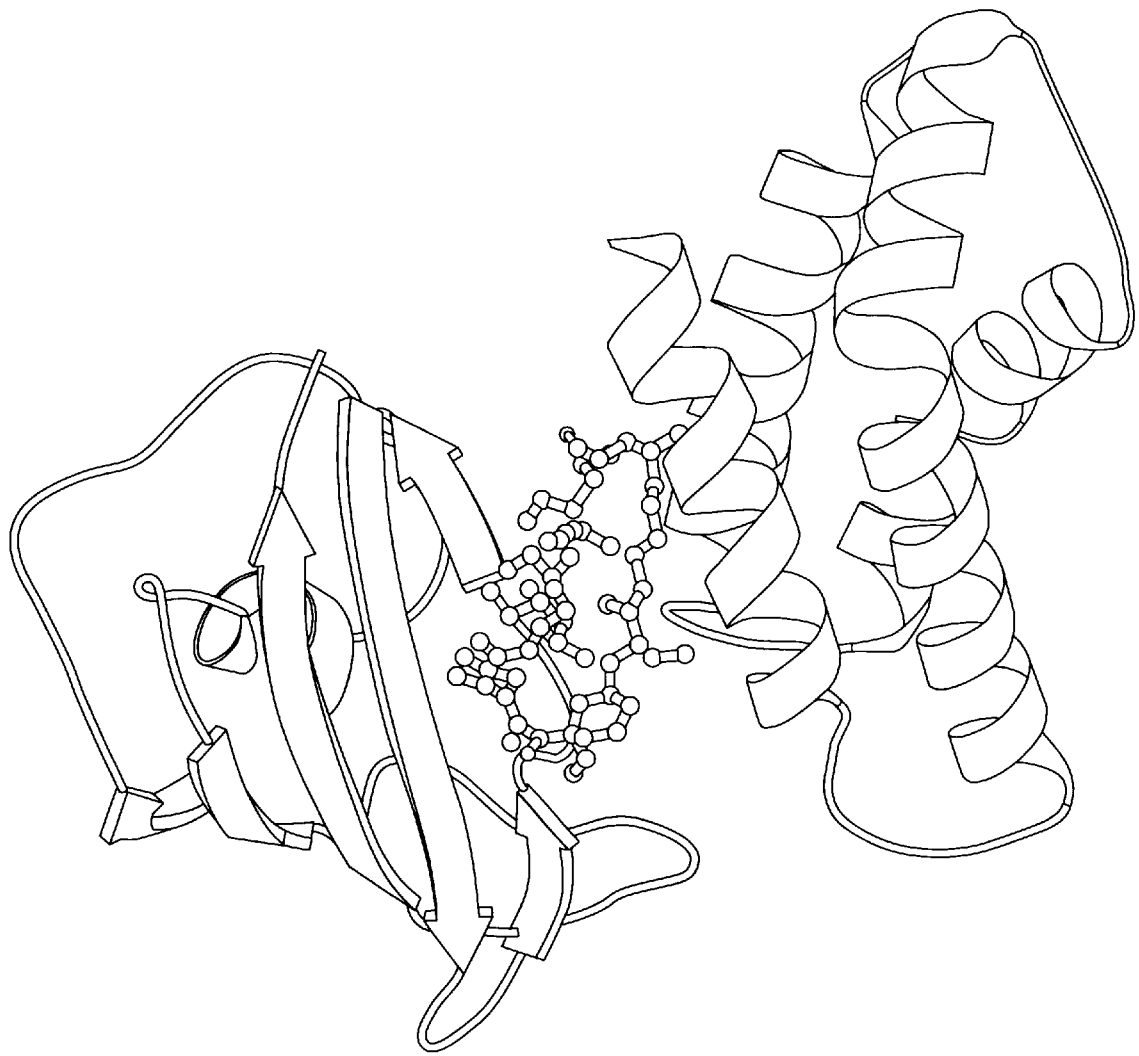
FIG. 3 depicts a ribbon diagram of the three dimensional structure of the FKBP12apamycin:FRB domain complex, as defined by the coordinates of FIG. 4.

Even more preferred is a machine-readable data storage medium that is capable of displaying a graphical three-dimensional representation of a molecule or molecular complex that is defined by the structural coordinates of a complex, FRB-containing protein component thereof, or portion thereof, comprising structural coordinates of an FRB domain such as the FRAP FRB coordinates set forth in our attached FIG. 4 ± a root mean square deviation from the conserved backbone atoms of the amino acids thereof of not more than 1.5 Å. An illustrative embodiment of this aspect of the invention is a conventional 3.5" diskette, DAT tape or hard drive encoded with a data set, preferably in PDB format, comprising the coordinates of our FIG. 4. FIG. 3 illustrates a print-out of a graphical three-dimensional representation of such a complex.

In another embodiment, the machine-readable data storage medium comprises a data storage material encoded with a first set of machine readable data which comprises the Fourier transform of the structural coordinates set forth in FIG. 4 (or again, a derivative thereof), and which, when using a machine programmed with instructions for using said data, can be combined with a second set of machine readable data comprising the X-ray diffraction pattern of a molecule or molecular complex to determine at least a portion of the structural coordinates corresponding to the second set of machine readable data.

FIG. 1 illustrates one version of these embodiments. The depicted system includes a computer A comprising a central processing unit ("CPU"), a working memory which may be, e.g., RAM (random-access memory) or "core" memory, mass storage memory (such as one or more disk drives or CD-ROM drives), one or more cathode-ray tube ("CRT") display terminals, one or more keyboards, one or more input lines (IP), and one or more output lines (OP), all of which are interconnected by a conventional bidirectional system bus.

Input hardware B, coupled to computer A by input lines, may be implemented in a variety of ways. Machine-readable data of this invention may be inputted via the use of a modem or modems connected by a telephone line or dedicated data line L. Alternatively or additionally, the input hardware may comprise CD-ROM drives or disk drives D. In conjunction with the CRT display terminal, a keyboard may also be used as an input device.

Output hardware, coupled to computer A by output lines, may similarly be implemented by conventional devices. By way of example, output hardware may include a CRT display terminal for displaying a graphical representation of a protein of this invention (or portion thereof) using a program such as QUANTA as described herein. Output hardware might also include a printer, so that hard copy output may be produced, or a disk drive, to store system output for later use.

In operation, the CPU coordinates the use of the various input and output devices, coordinates data accesses from mass storage and accesses to and from working memory, and determines the sequence of data processing steps. A number of programs may be used to process the machine-readable data of this invention. Examples of such programs are discussed in reference to the computational methods of drug discovery as described herein. Specific references to components of the hardware system of FIG. 1 are included as appropriate throughout the following description of the data storage medium.

Figure 2A:
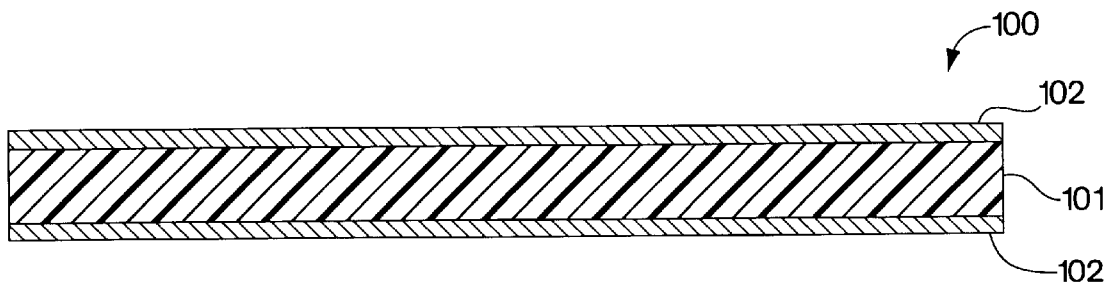
FIG. 2 depicts storage media of this invention.

FIG. 2A shows a cross section of a magnetic data storage medium 100 which can be encoded with a machine-readable data that can be carried out by a system such as a system of FIG. 1. Medium 100 can be a conventional floppy diskette or hard disk, having a suitable substrate 101, which may be conventional, and a suitable coating 102, which may be conventional, on one or both sides, containing magnetic domains (not visible) whose polarity or orientation can be altered magnetically. Medium 100 may also have an opening (not shown) for receiving the spindle of a disk drive or other data storage device 24.

The magnetic domains of coating 102 of medium 100 are polarized or oriented so as to encode in a manner which may be conventional, machine readable data such as that described herein, for execution by a system such as a system of FIG. 1.

Figure 2B:
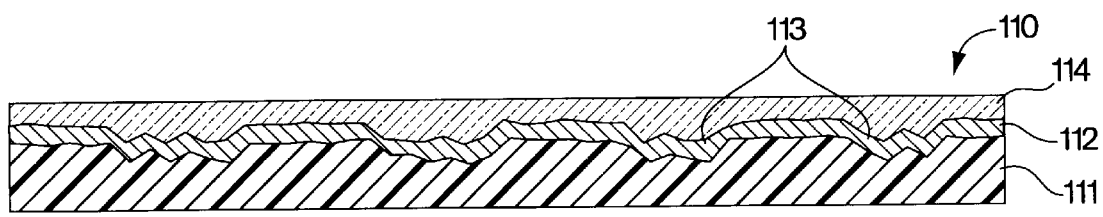

FIG. 2B shows a cross section of an optically-readable data storage medium 110 which also can be encoded with such machine-readable data, or set of instructions, which can be carried out by a system such as a system of FIG. 1. Medium 110 can be a conventional compact disk read only memory (CD-ROM) or a rewritable medium such as a magneto-optical disk which is optically readable and magneto-optically writable. Medium 100 preferably has a suitable substrate 111, which may be conventional, and a suitable coating 112, which may be conventional, usually of one side of substrate 111.

In the case of CD-ROM, coating 112 is reflective and is impressed with a plurality of pits 113 to encode the machine-readable data. The arrangement of pits is read by reflecting laser light off the surface of coating 112. A protective coating 114, which preferably is substantially transparent, is provided on top of coating 112.

In the case of a magneto-optical disk, coating 112 has no pits 113, but has a plurality of magnetic domains whose polarity or orientation can be changed magnetically when heated above a certain temperature, as by a laser (not shown). The orientation of the domains can be read by measuring the polarization of laser light reflected from coating 112. The arrangement of the domains encodes the data as described above.

Use of Structure in Drug Discovery

The availability of the three-dimensional structure of the ternary complex of FKBP12:rapamycin:FRB of FRAP makes structure-based drug discovery approaches possible. Structure-based approaches include de Novo molecular design, computer-aided optimization of lead molecules, and computer-based selection of candidate drug structures based on structural criteria.

Rapamycin mimetics may be developed from the bound conformation of rapamycin by design, by searching databases for replacements of one or more structural segments of rapamycin, or by enhancement of existing ligand-protein interactions (i.e., by replacing a component moiety of a ligand with a substitute moiety capable of greater interaction with the target protein, whether through accessible protein contact points or by extrusion of otherwise sequestered waters). Knowledge of the bound conformation of a ligand can suggest avenues for conformational restriction and replacement of atoms and/or bonds of rapamycin. A less biased approach involves computer algorithms for searching databases of three dimensional structures to identify replacements for one or more portions of the ligand. By this method, one can generate compounds for which the bioactive conformation is heavily populated, i.e., compounds which are based on particularly biologically relevant conformations of the ligand. Algorithms for this purpose are implemented in programs such as Cast-3D (Chemical Abstracts Service), 3DB Unity (Tripos, Inc.), Quest-3D (Cambridge Crystallographic Data Center), and MACCS/ISIS-3D (Molecular Design Limited). These geometric searches can be augmented by steric searching, in which the size and shape requirements of the binding site are used to weed out hits that have prohibitive dimensions. Programs that may be used to synchronize the geometric and steric requirements in a search applied to the FRB of FRAP include CAVEAT (P. Bartlett, University of California, Berkeley), HOOK (MSI), ALADDIN (Daylight Software) and DOCK (I.D. Kuntz, University of California, San Francisco; see e.g. http://www.cmpharm.ucsf.edu/kuntz-/kuntz.html and references cited therein). All of these searching protocols may be used in conjunction with existing corporate databases, the Cambridge Structural Database, or available chemical databases from chemical suppliers.

Characterization of Compounds

Compounds designed, selected and/or optimized by methods described above may be evaluated for binding activity with respect to proteins containing one or more FRB domains using various approaches, a number of which are well known in the art. For instance, compounds may be evaluated for activity as competitive inhibitors of the binding of a natural ligand for the FRB, e.g. FKBP12:rapamycin in the case of the FRAP FRB. Competitive inhibition may be determined using any of the numerous available technologies known in the art.

Such compounds may be further evaluated for activity in inhibiting cellular or other biological events mediated by a pathway involving the interaction of interest using a suitable cell-based assay or an animal model. Cell-based assays and animal models suitable for evaluating inhibitory actvity of a compound with respect to a wide variety of cellular and other biological events are known in the art. New assays and models are regularly developed and reported in the scientific literature.

For example, compounds which mimic the binding of rapamycin or FKBP12:rapamycin with respect to FRAP may be evaluated for biological activity in the mouse spelocyte mitogenesis assay or the high-flux yeast-based assay of Luengo et al, supra. A battery of in vivo models may be used to profile the breadth of the compound's immunosuppressive (or other) activity and compare the profile to those of positive controls such as rapamycin itself. Comparisons may also be made to other currently accepted immunosuppressive compounds, e.g. cyclophosphamide, and leflunomide. Initial in vivo screening models include: Delayed type hypersensitivity testing, Allogeneic skin transplantation, and Popliteal lymph node hyperplasia. Compounds demonstrating optimal profiles in the above models are advanced into more sophisticated models designed to confirm immunosuppressive activity in specific therapeutic areas including: Rheumatoid arthritis, Transplantation, Graft vs. host disease, and Asthma.

By way of further illustration, compounds may be evaluated in relevant conventional in vitro and in vivo assays for inhibition of the initiation, maintenance or spread of cancerous growth. See e.g., Ishii et al., J. Antibiot. XLII:1877–1878 (1989) (in vitro evaluation of cytotoxic/ antitumor activity); Sun et al, U.S. Pat. No. 5,206,249 (issued Apr. 27, 1993)(in vitro evaluation of growth inhibitory activity on cultured leukemia cells); and Sun et al, supra (xenograft models using various human tumor cell lines xenografted into mice, as well as various transgenic animal models).

Single and multiple (e.g., 5 to 7 days) dose investigative toxicology studies are typically performed in the efficacy test species using the intended route of administration for the efficacy study. These investigative toxicology studies are performed to identify maximum tolerated dose, subjective bioavailability from the intraperitoneal or oral routes of administration, and estimation of an initial safety margin. Initial bioavailability and pharmacokinetics (blood clearance) of the compounds may be determined, with standard cold or radioactive assay methods, to assist in defining appropriate dosing regimens for the compounds in the animal models.

Pharmaceutical Compositions and Uses of Rapamycin Mimetics and Other FRAP-Binding Compounds Compounds which bind to an FRB domain may be used as biological reagents in binding assays as described herein for functional classification of members of the PIK-related kinase family, particularly newly discovered proteins, based on ligand specificity.

Moreover, compounds identified as described above can be used for their immunosuppressive or other pharmacologic activity in place of rapamycin.

A compound selected or identified in accordance with this invention can be formulated into a pharmaceutical composition containing a pharmaceutically acceptable carrier and/ or other excipient(s) using conventional materials and means. Such a composition can be administered as an immunosuppresant, for example, to an animal, either human or non-human. Administration of such composition may be by any conventional route (parenteral, oral, inhalation, and the like) using appropriate formulations as are well known in this art. The compound can be employed in admixture with conventional excipients, i.e., pharmaceutically acceptable organic or inorganic carrier substances suitable for parenteral administration.

Pharmaceutical Applications

By virtue of its capacity to mimic the interaction of rapamycin with FRAP, a compound identified as described herein may be used in pharmaceutical compositions and methods for treatment or prevention of various diseases and disorders in a mammal in need thereof.

Mammals include rodents such as mice, rats and guinea pigs as well as dogs, cats, horses, cattle, sheep, non-human primates and humans.

The preferred method of such treatment or prevention is by administering to a mammal an effective amount of the compound to prevent, alleviate or cure said disease or disorder. Such effective amounts can be readily determined by evaluating the compounds of this invention in conventional assays well-known in the art, including assays described herein.

Therapeutic/Prophylactic Administration & Pharmaceutical Compositions

The invention provides methods of treating, preventing and/or alleviating the symptoms and/or severity of an untoward immune response or other disease or disorder referred to above by administration to a subject of a in an amount effective therefor. The subject will be an animal, including but not limited to animals such as cows, pigs, chickens, etc., and is preferably a mammal, and most preferably human.

Various delivery systems are known and can be used to administer the compound, e.g., encapsulation in liposomes, microparticles, microcapsules, etc. One mode of delivery of interest is via pulmonary administration, as detailed more fully infra. Other methods of introduction include but are not limited to intradermal, intramuscular, intraperitoneal, intravenous, subcutaneous, intranasal, epidural and oral routes. The compound may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. For treatment or prophylaxis of nasal, bronchial or pulmonary conditions, preferred routes of administration are oral, nasal or via a bronchial aerosol or nebulizer.

In specific embodiments, it may thus be desirable to administer the compound locally to the area in need of treatment; this may be achieved by, for example, and not by way of limitation, local infusion during surgery, topical application, by injection, by means of a catheter, by means of a suppository, or by means of a skin patch or implant, said implant being of a porous, non-porous, or gelatinous material, including membranes, such as sialastic membranes, or fibers.

This invention also provides pharmaceutical compositions. Such compositions comprise a therapeutically (or prophylactically) effective amount of the compound, and a pharmaceutically acceptable carrier or excipient. Such a carrier includes but is not limited to saline, buffered saline, dextrose, water, glycerol, ethanol, and combinations thereof. The carrier and composition can be sterile. The formulation should suit the mode of administration.

The composition, if desired, can also contain minor amounts of wetting or emulsifying agents, or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc.

In a specific embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic to ease pain at the side of the injection. Generally, the ingredients are supplied either separately or mixed together in unit dosage form, for example, as a lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

Administration to an individual of an effective amount of the compound can also be accomplished topically by administering the compound(s) directly to the affected area of the skin of the individual. For this purpose, the compound is administered or applied in a composition including a pharmacologically acceptable topical carrier, such as a gel, an ointment, a lotion, or a cream, which includes, without limitation, such carriers as water, glycerol, alcohol, propylene glycol, fatty alcohols, triglycerides, fatty acid esters, or mineral oils.

Other topical carriers include liquid petroleum, isopropyl palmitate, polyethylene glycol, ethanol (95%), polyoxyethylene monolaurate (5%) in water, or sodium lauryl sulfate (5%) in water. Other materials such as anti-oxidants, humectants, viscosity stabilizers, and similar agents may be added as necessary.

In addition, in certain instances, it is expected that the compound may be disposed within devices placed upon, in, or under the skin. Such devices include patches, implants, and injections which release the compound into the skin, by either passive or active release mechanisms. Materials and methods for producing the various formulations are well known in the art [see e.g. U.S. Pat. Nos. 5,182,293 and 4,837,311 (tablets, capsules and other oral formulations as well as intravenous formulations)].

The effective dose of the compound will typically be in the range of about 0.01 to about 50 mg/kgs, preferably about 0.1 to about 10 mg/kg of mammalian body weight, administered in single or multiple doses. Generally, the compound may be administered to patients in need of such treatment in a daily dose range of about 1 to about 2000 mg per patient.

The amount of the compound which will be effective in the treatment or prevention of a particular disorder or condition will depend on the nature of the disorder or condition, and can be determined by standard clinical techniques. In addition, in vitro or in vivo assays may optionally be employed to help identify optimal dosage ranges. Effective doses may be extrapolated from dose-response curves derived from in vitro or animal model test systems. The precise dosage level of the compound, as the active component(s), should be determined as in the case of all pharmaceutical treatments, by the attending physician or other health care provider and will depend upon well known factors, including route of administration, and the age, body weight, sex and general health of the individual; the nature, severity and clinical stage of the disease; and the use (or not) of concomitant therapies.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceutical or biological products, which notice reflects approval by the agency of manufacture, use or sale for human administration.

Pulmonary Administration

In one embodiment of this invention, the compound is administered by pulmonary administration, e.g. via aerosolization. This route of administration may be particularly useful for treatment or prophylaxis of bronchial or pulmonary infection or tumors.

Pulmonary administration can be accomplished, for example, using any of various delivery devices known in the art (see e.g., Newman, S. P., 1984, in Aerosols and the Lung, Clarke and Davia (eds.), Butterworths, London, England, pp. 197–224; PCT Publication No. WO 92/16192 dated Oct. 1, 1992; PCT Publication No. WO 91/08760 dated Jun. 27, 1991; NTIS Patent Application 7-504-047 filed Apr. 3, 1990 by Roosdorp and Crystal), including but not limited to nebulizers, metered dose inhalers, and powder inhalers. Various delivery devices are commercially available and can be employed, e.g., Ultravent nebulizer (Mallinckrodt, Inc., St. Louis, Mo.); Acorn II nebulizer (Marquest Medical Products, Englewood, Colo.), Ventolin metered dose inhaler (Glaxo Inc., Research Triangle Park, N.C.); Spinhaler powder inhaler (Fisons Corp., Bedford, Mass.) or Turbohaler (Astra). Such devices typically entail the use of formulations suitable for dispensing from such a device, in which a propellant material may be present.

Ultrasonic nebulizers tend to be more efficient than jet nebulizers in producing an aerosol of respirable size from a liquid (Smith and Spino, "Pharmacokinetics of Drugs in Cystic Fibrosis," Consensus Conference, Clinical Outcomes for Evaluation of New CF Therapies, Rockville, Md., Dec. 10–11, 1992, Cystic Fibrosis Foundation).

A nebulizer may be used to produce aerosol particles, or any of various physiologically acceptable inert gases may be used as an aerosolizing agent. Other components such as physiologically acceptable surfactants (e.g., glycerides), excipients (e.g., lactose), carriers, and diluents may also be included.

This invention is not to be limited in scope by the specific embodiments described herein. Indeed, various modifications of the invention in addition to those described herein will become apparent to those skilled in the art from the foregoing description. Such modifications are intended to fall within the the scope of the appended claims.

Various patents, patent applications and publications are cited herein, the disclosures of which are incorporated by reference in their entireties.

EXPERIMENTAL EXAMPLES

I. Protein Preparation cDNAs encoding human FKBP12 (Standaert et al, 1990) and the 12-kDa FRAP fragment containing the FRB domain (Chen et al, 1995) (FRAP12) were subcloned into pGEX-2T (Pharmacia) for the expression of GST-FKBP12 and GST-FRAP12 fusion proteins in E.coli strain BL21. Typically, a 2-liter culture was grown to $OD_{600}$~0.6 at 30° C. and induced with 0.3 mM IPTG at room temperature for 6 hours. Purification and thrombin cleavage of the fusion proteins were performed according to standard procedures (manual from Pharmacia). After removal of free GST, the samples containing FKBP12 or FRAP12 were concentrated to ~10 mL in a 50 mL stir-cell ultraconcentrator (Amicon) with a 3-kDa cutoff filter, and fractionated on a Sephacryl S-100 column (2.5 cm×85 cm) equilibrated in 10 mM phosphate buffer (pH 7.4) containing 136 mM NaCl, 3 mM KCl, 1 mM DTT. Fractions containing pure FKBP12 or FRAP12 (>95% purity judged by SDS-PAGE) were combined and concentrated to ~10 mg/mL using a stir-cell ultraconcentrator. The concentrated samples were stored in the same phosphate buffer at 4° C.

II. Crystallization & Structure Determination Crystallization

Recombinant human FKBP12 purified from *E. coli* was used at 10 mg/mL in 10 mM tris-HCl pH 8.0. Rapamycin was dissolved in methanol and mixed with FKBP12 in a 2:1 molar ratio. The mixture was lightly vortexed and stored overnight at 4° C. to insure complete complex formation. Purified 12-kDa FRB domain of FRAP at 10 mg/mL in 50 mM tris-HCl pH 8.0 was added to this mixture in a 1:1 (FKBP12-rapamycin complex:FRB domain) molar ratio. This mixture was also lightly vortexed and let sit overnight at 4° C. to insure complete complex formation. Crystallization conditions were screened using the hanging drop method, and rectangular rod-shaped crystals were obtained using: 20% PEG 8000, 10% MPD and 10 mM tris-HCl at pH 8.5. For the hanging drop method, drops of 4 $\mu$L containing 2 $\mu$L of complex solution and 2 $\mu$L of reservoir solution were equilibrated against 0.5 mL of the reservoir solution. Microseeding techniques were used to prepare additional crystals. The initial crystals were crushed and diluted to prepare a seed solution that was added to newly prepared drops. After two weeks, a shower of tiny crystals was obtained. Macroseeding techniques were then applied to get large crystals suitable for X-ray diffraction. A tiny but well-formed crystal was picked and used as a crystallization seed. After two to three weeks, rectangular rod-shaped crystals with a maximum size of 0.3×0.2×0.1 mm$^3$ were obtained, and these crystals were suitable for data collection. The Hg-derivative crystal was obtained by soaking the native crystal in 2 mM HgCl$_2$ solution overnight. All of the crystallization experiments were done at 4° C.

Data Collection

All data sets were collected at room temperature on a San Diego multiwire area detector system mounted on a Rigaku RU-200 rotating anode X-ray source operating at 50 kV and 150 mA. The detector was positioned at a 2θ-value of –30° with a 544 mm detector-crystal distance for the high resolution data and 12° with a 506 mm detector-crystal distance for the low resolution data. The data collection was performed using an ω-can with an increment of 0.10° for each frame and 40 second exposure time per frame. Crystals belong to the orthorhombic space group P2$_1$2$_1$2$_1$ with unit-cell dimension of a=44.63, b=52.14, c=102.53 Å and one FKBP12-rapamycin-FRB complex in the asymmetric unit. Hg-derivative crystal data were collected under the same conditions. For the native data set, the measured intensity data were processed using SCALEPACK (Otwinski et al, 1992) giving 6920 unique reflections out of 43447 measured reflections to 2.7 Å resolution (98.5% data coverage) with R$_{sym}$ of 7.1%. For the Hg-derivative data set, the number of unique reflection was 6884 out of 42681 measured reflections to 2.7 Å (98.0% data coverage), with R$_{sym}$ of 7.1%.

Structure Determination

The crystal structure of the ternary complex was solved using the molecular replacement (MR) method combined with the single isomorphous replacement with anomalous scattering (SIRAS) method. Initial phases were obtained from the molecular replacement search using the FKBP12-rapamycin complex structure as a search model. The cross rotation search revealed a clear peak at $\Theta_1$=10.8°, $\Theta_2$=70.0°, $\Theta_3$=309.4° with height/r.m.s. ratio of 12.9 and the translation search also showed a clear peak at x=0.000, y=0.230, z=0.417 with height/r.m.s. ratio of 10.5. Rigid body refinement resulted in an R factor of 0.449 (10–2.7 Å). All molecular replacement calculations used the X-PLOR program (Brunger, 1990). However, the resulting difference electron density map was noisy and hard to interpret. In order to improve the map quality, an Hg derivative crystal was obtained. These data were compared with the native data to give an Rdiff of 12.7%. Two heavy atom sites were found from the difference Patterson map and were refined using the program PHASES (Furey et al,1990). One Hg is bound to Cys22 of FKBP12 with full occupancy—the same Hg site seen in the FKBP12-FK506 complex. The other heavy atom site is in the middle of FRB domain where it is bound to Cys2085 of FRAP with an occupancy factor of 0.6. Both Patterson-deduced heavy atom positions were validated in the Of-Fc difference map using Of of the heavy atom derivative and Fc from the molecular replacement solution. Anomalous dispersion measurements were included in this data set and 16 cycles of a solvent flattening procedure were applied, resulting in a phasing power of 2.76 and mean figure of merit of 0.840. All of these calculations were performed using the program PHASES. The electron density map was calculated using the combined phase from the SIRAS and the molecular replacement solution, which clearly showed four helix bundle architecture of FRB domain of FRAP.

Model Building and Refinement

The FKBP12-rapamycin part was well defined in the initial electron density map; only minor changes in the backbone of 30s loop and some side chains were enough to fit the model of FKBP12-rapamycin structure to this electron density map. For the FRB domain part, most of a polyalanine chain could be traced for the helix regions in the initial map. After several cycles of the positional refinement using X-PLOR, loop regions could be traced and the amino acid sequence could be assigned. The program CHAIN (Sack, 1988) was used for the model fitting and building the ternary complex. A total of 95 residues were built for the FRB domain of FRAP; three residues in the N-terminal and two residues in the C-terminal of FRB domain had no electron density and were not included. Positional refinement was followed by simulated annealing (slow cooling from 3000K to 300K in 25 K steps, 0.0005 ps per step and 50 total steps were used in the simulation at each temperature) and restrained B-factor refinement. All refinements were done using the X-PLOR package. Solvent molecules were assigned during the iterative positional and B-factor refinement procedure, if they appeared at the 3.5 σ level of fo-Fc map, showed good hydrogen bonding geometry and had a low B-factor (less than 50 Å$^2$). The current structure includes 202 amino acids (107 for FKBP12 and 95 for FRB domain), one rapamycin, and 23 water molecules. The final R factor is 19.3% with an Rfree of 29.9%. The free R-factor is calculated with 10% of the data that were selected at the beginning of the analysis. Crystallographic statistics are summarized in Table 1.

Quality of the Coordinates

The final coordinates have good geometry and r.m.s. deviations from the ideality are 0.008 Å for bond lengths and 1.5° for bond angles. Examined by the program PROCHECK (Laskowski, 1993), the current 2.7 Å resolution structure shows that the main-chain and side-chain geometrical parameters are better than expected at this resolution with an overall G-factor of 0.0. Ramachandran plots of φ, ψ, angles showed that 86% of the nonglycine and nonproline residues are in energetically most favored regions. The average temperature factors for total atoms and main-chain atoms are 17.0 and 14.7 Å$^2$ respectively. The r.m.s. variation in the B-factor of bonded atoms is 2.5 Å². The Luzzati plot (Luzzati, 1952) indicates that the average coordinate error of this complex structure is between 0.25 and 0.30 Å.

Those structural coordinates are set forth in Protein Databank format in FIG. 4, below. Such data may be transferred to any desired medium, and formatted as desired, for the practitioner's computer.

This invention encompasses those coordinates as well as any translation or rotation or the like thereof which maintains the internal coordinates, i.e., which maintains their intrinsic, internal relationship. Those skilled in the art will appreciate that the coordinates may be subjected to other transformations including, e.g. molecular mechanics calculations such as dynamic simulation, minimization, etc. This invention further encompasses the use of coordinates of the FRB of FRAP, of the ternary complex, or of the corresponding region of FRAP homologs, and in particular, the coordinates set forth in Appendix I, in conducting such transformations (or more extensive transformations such as the generation of alternative conformations), as well as the products of such transformations (i.e., derivatives of the coordinates).

Seven days later the ears of sensitized mice are painted (challenge) with a lower concentration of the compound. Antigen processing and presentation, T lymphocyte activation, leukocyte infiltration, humoral mediator release, increased microvascular permeability, and plasma exudation all result from challenge of sensitized mice and lead to edema formation. Edema presents as a two- to three- fold increase in ear thickness within twenty-four hours.

The test compounds or standards can be applied (topical or parenteral) at various times before or after the sensitization or challenge phases. Increased ear thickness is prevented by several compounds including immunosuppressive agents and steroids. This model is a primary model for contact dermatitis.

(b) Allogeneic Skin Transplantation

An allogeneic skin transplant model is used to identify immunosuppressive activity of test compounds. In this model, donor mouse thoracic skin (Balb/c) is surgically grafted onto the thorax of recipient mice (C57b1/6). Host rejection of the graft is evidenced by erythema, drying out, and retraction of donor skin. The mean graft survival time is 10 to 11 days, with 80% of the grafts being rejected by 12 days. Active novel immunosuppressive compounds, like existing immunosuppressive compounds, will prolong graft survival.

TABLE 1

Crystallographic statistics of the ternary complex FKBP12-rapamycin-FRB domain of FRAP

| | | Data collection statistics | | | |
|---|---|---|---|---|---|
| | Resolution | No. of reflections | | Data | |
| Data Set | (Å) | Measured | Unique | coverage (%) | $R_{sym}$ (%)* |
| Native | 2.7 | 43447 | 6920 | 98.5 | 7.1 |
| $HgCl_2$ | 2.7 | 42681 | 6884 | 98.0 | 7.1 |

Molecular replacement results

Rotation function    $\Theta_1 = 10.82°$    $\Theta_2 = 70.00°$    $\Theta_3 = 309.35°$    Height/r.m.s. = 12.9σ
Translation function    x = 0.000    y = 0.230    z = 0.417    Height/r.m.s. = 10.5σ

Heavy atom data statistics (SIRAS)

| Sites | $R_{diff}$ (%)† | Phasing power ◊ | Mean figure-of-merit |
|---|---|---|---|
| 2 | 12.7 | 2.76 | 0.840 |

Refinement statistics

| Resolution | Reflections | Number of | R-factor | $R_{free}$ | R.M.S. deviation | |
|---|---|---|---|---|---|---|
| (Å) | (with \|F\| > 3σ) | atoms | (%) | (%) | Bond lengths | Bond angles |
| 8–2.7 | 6206 | 1727 | 19.3 | 29.9 | 0.008 | 1.48 |

*$R_{sym} = \Sigma|I - <I>|/\Sigma I$, where I is the observed intensity and <I> is the average intensity from multiple measurement.
†$R_{diff} = \Sigma|F_{PH} - F_p|/\Sigma F_{PH}$, where $F_p$ and $F_{PH}$ are the amplitudes of native and derivative structure factors, respectively.
◊ Phasing power = r.m.s. ($F_H/\epsilon$), where $F_H$ is heavy-atom structure fator amplitude and $\epsilon$ is residual lack of closure error.

III. Assays

Compounds which bind to the FRB of FRAP may be evaluated using materials and methods useful for testing the biological or pharmacological activity of rapamycin analogs. See e.g. Luengo et al, 1995. In addition, the following animal models may be used for further evaluation of such compounds:

(a) Delayed Type Hypersensitivity

Mouse abdomens are painted with sensitizing chemicals (sensitization) such as dinitroflourobenzene or oxazalone.

(c) Popliteal Lymph Node Hyperplasia

This model directly assesses T lymphocyte proliferation in vivo. Spleen cells, obtained from Balb/c mice, are isolated and administered into the foot pads of C3H mice. Within four days, the popliteal lymph nodes can be removed from the recipient mice and weighed. Other hematological assessments including FACS scanning for T lymphocyte subpopulations may also be performed. Active compounds, like existing immunosuppressive compounds, will inhibit the increase in node mass.

(d) Rheumatoid Arthritis

Several models are available for assessment of anti-arthritic activity, including adjuvant-induced, carageenan-induced, and collagen-induced arthritis in rats and/or mice. Paw pads are injected with one of these agents. Paws increase in volume, and measurements are made between 20 and 30 days later. The ability of test compounds to prevent the induction of paw swelling is tested with daily treatment for 12 consecutive days following the injection of inducing agent. The ability for the test compounds to reverse the progression of the paw swelling is tested by administration of the compound for 12 consecutive days beginning on the twelfth day following the injection of inducing agent. Paw swelling measurements are made by water displacement plethysmography. Histology is also an appropriate endpoint for these studies. The MRL/1pr-mouse model, described above, is required for the rheumatoid arthritis indication. This model is a spontaneous autoimmune model that develops rheumatoid arthritis resembling the human condition, including the presence of circulating rheumatoid factor, pannus formation, and bone and cartilage erosion.

(e) Systemic Lupus Erythematosus

Systemic lupus erythematosus is another autoimmune disease with several animal models. Several murine strains develop spontaneous SLE. One such strain is MRL/lpr-mice. These mice, over time (20 to 30 weeks) develop auto-antibodies against dsDNA, nuclear antigens, and renal basement membrane. This leads to complement fixation and immune complex formation. Damage to the kidney becomes apparent with the onset of proteinuria. Many of the other physiologic, hematologic, and immunologic aberrations described below for the CGVHD model are present. Immunosuppressive compounds such as cyclosporin, cydophosphamide, and leflunomide can prevent and reverse the course of disease in this model. Interestingly, these mice also develop pathologies akin to rheumatoid arthritis.

The murine chronic graft versus host disease model (CGVHD, described below) is a model of SLE that contains many of the clinical features of SLE. Activity in this model has been shown to be predictive of activity in the more clinically relevant SLE models.

(f) Transplantation

Allograft transplantation (skin graft) assay is often used as an initial test of immunosuppressive activity. While this model is useful as a screen, it may be supplemented with assays based on animal transplant models involving transplantation of internal organ (heart, liver, kidney, bone marrow) with use of "clinically acceptable" physiologic endpoints to assess graft survival. Efficacy of test compounds in only a very limited number of these rodent models is required. Following observation of activity in a rodent model, the test compounds are typically tested in further animal models (e.g., canine, porcine or non-human primate). Active compounds decrease acute and chronic rejection and prolong transplant survival.

(g) Graft vs. Host Disease

Chronic GVHD (CGVHD) can be used to model $CD4^+$-dependent humoral immunity. It is induced in $BDF_1$ mice (which are progeny of DBA/2 male x C57BL/6 female matings) by administering to them isolated spleen:lymph node cells from DBA/2 mice. This results in: a) disregulation and stimulation of $CD4^+$ T lymphocyte ($Ly1^+$; murine marker) activity due to incompatibilities at MHC II molecules, and b) abnormal T-B lymphocyte cooperation. The resulting pathological state, in many ways, mimics systemic lupus erythematosus (SLE). Several measurable endpoints develop within 14 days; including, circulating anti-host IgG and IgE antibodies, altered T and B lymphocyte proliferation activity measured in vitro, complement utilization, hemagglutination, slow progressive wasting, dermal aberrations, splenomegaly, lymphoid hyperplasia, and proteinuria. Only a few of these endpoints need to be measured. Active compounds are are those which limit T lymphocyte disregulation and abrogate changes in these variables. Many steroids (e.g., prednisolone), cyclosporine, FK-506, cyclophosphamide, and leflunomide are all active in this model and can be used as positive controls.

The acute GVHD model (AGVHD) is also produced in $BDF_1$ mice. In this case, isolated spleen:lymph node cells from C57BL/6 mice are administered. This results in disregulation and stimulation of $CD8^+$ T lymphocytes due to incompatibilities in the MHC I molecules. Elevated cytokine levels and donor clonal expansion occurs. Ultimately, donor cytotoxic T lymphocytes and NK cells rapidly reject host tissue and cause relatively rapid death of the recipient. The progression of AGVHD in this model is assessed by measurement of hematologic abnormalities (including T cell number and type), cytokine elevations (TNF, IL-1, IL-2, and/or IL-4), low body weight, hypo$\gamma$globulinemia, circulating hematologic characteristics indicative of aplastic anemia (granulocytopenia, thrombocytopenia), ex vivo NK or CTL activity, and host survival. Active compounds are those which abrogate changes in the variables, and prolong survival over 4 to 6 weeks.

(h) Astham

Asthma offers another opportunity for safe immunosuppressive therapy. Atopic asthmatics have antibody mediated hypersensitivity and the often occurring late phase reaction is likened to a DTH response. Asthma has only recently been defined as an inflammatory disease (1992). Since then, several publications from prominent asthmatologists demonstrate the presence of activated $CD4^+$ and $CD8^+$ T lymphocytes in bronchoalveolar lavage fluid and blood of atopic asthmatics. The ratios of these cells changes in asthmatic conditions. Furthermore, several of the T cell associated cytokines (IL-1, IL-2, IL-4, IL-5, and TNF) are all implicated in clinical and experimental asthma. Inflammatory events in asthma are now considered to be T lymphocyte driven. Initial clinical trials with inhaled cyclosporin suggest that local immunosuppression can ameliorate airway hyperreactivity—the underlying defect in asthma.

The guinea pig model of antigen-induced pulmonary aberrations is used as a model for asthma. These animals are actively sensitized to ovalbumin to generate high circulating titers of anti-ovalbumin antibody with seroconversion to the IgE class, as is the case with atopic asthmatics. Aerosol challenge of sensitized guinea pigs results in measurable eosinophil rich pulmonary infiltrates (approximately a 16-fold increase in eosinophils), pulmonary edema, and mucous plugging of the small airways; all culminating in the expression of the underlying defect in asthma—airway. hyperreactivity (approximately a 3 to 4-fold increase in reactivity). Acute bronchoconstriction is obviously present and points the aforementioned presence of the pathophysiologic sequelae. Active compounds are those which lessen or abrogate such symptoms.

The above description is meant to illustrate, rather than limit the scope of the invention. Given the foregoing description, numerous variations in the materials or methods employed in performing the invention will be obvious to one skilled in the art. Any such obvious variation is to be considered within the scope of the invention. Full references to literature cited above (by reference to author and year) are provided below:

References

Brown, E. J., Albers, M. W., Shin, T. B., Ichickawa, K., Keith, C. T., Lane, W. S. & Schreiber, S. L. Nature 369, 756–758 (1994).

Brunger, A. T. *X-PLOR Version 3.1 Manual* (Yale Univ. Press, New Haven, Conn., 1992)

Chen, J., Zheng, X.-F., Brown, E. J. & Schreiber, S. L. Proc. Natl. Acad. Sci. USA 92, 4947–4951 (1995).

Chiu, M. I., Katz, H & Berlin, V. Proc. Natl. Acad. Sci. USA 91, 12574–12578 (1994).

Clardy, J. . Proc. Natl. Acad. Sci. USA 92, 56–61 (1995).

Dayhoff, M. O.; Schwartz, R. M.; Orcutt, B. C., Atlas of Protein Sequence and Structure, 5, Suppl. 3,345 (1979)

Furey, W. and Swaminathan, S. *American Crystallographic Association Mtg. Abstr. Ser.* 2 18, 73 (1990)

Gonnet, G. H., Cohen, M. A., Benner, S. A. Science, 256, 1443 (1992)

Greer, J., J. Mol. Biol. , 153, 1027 (1981)

Griffith, J. P., Kim, J. L., Kim, E. E., Sintchak, M. D., Thomson, J. A., Fitzgibbon, M. J., Fleming, M. A., Caron, P. R., Hsiao, K. & Navia, M. A. Cell 82, 507–522 (1995).

Harris, N. L., Presnell, S. R., and Cohen, F. E. *J. Mol. Biol.* 236, 1356–1368 (1994)

Keith & Schreiber, 1995, Science 270:50–51.

Laskowski, R. A. *J. Appl. Cryst.* 26, 283–291 (1993)

Luengo, J. I., Yamashita, D. S., Dunnington, D., Konialian Beck, A., Rozamus, L. W., Yen, H., Bossard, M. J., Levy, M. A., Hand, A., Newman-Tarr, T., Badger, A., Faucette, L., Johnson, R. K., D'Alessio, K., Porter, T., Shu, A. Y., Heys, R., Choi, J., Kongsaeree, P., Clardy, J., and Holt, D. A. *Chemistry & Biology* 2, 471–481 (1995).

Luzzati, P. V. *Acta Cryst.* 5, 802–810 (1952)

Otwinski, Z. *The SCALEPACK Manual* (Howard Hughes Medical Institute, Yale Univ., New Haven, Conn., 1992).

Sabatini, D. M., Erdjument-Bromage, H., Lui, M., Tempst, P. & Snyder, S. H. Cell 78, 35–43 (1994).

Sack, J. S. *J. Mol. Graphics* 6, 224–225 (1988)

Schreiber, S. L. Cell 70, 365–368 (1992).

Sehgal, S. N., Baker, H. & Vezina, C. J. Antibiot. 6, 727–732 (1975).

Sehgal, S. N. Ann. N.Y. Acad. Sci. 696, 1–8 (1993).

Stan, R., McLaughlin, M. M., Cafferkey, R., Johnson, R. K., Rosenberg, M., and Livi, G. P. *J. Biol. Chem.* 269, 32027–32030 (1994)

Standaert, R. F., Galat, A., Verdine, G. L. & Schreiber, S. L. Nature 346, 671–674 (1990)

Tanaka, H., Kuroda, A., Marusawa, H., Hatanaka, H., Kino, T., Goto, T. & Hashimoto, M. J. Amer. Chem. Soc. 109, 5031–5033 (1987).

VanDuyne, G. D., Standaert, R. F., Schreiber, S. L. & Clardy, J. Science 251, 839–842 (1991).

VanDuyne, G. D., Standaert, R. F., Schreiber, S. L. & Clardy, J. J. Am. Chem. Soc. 113, 7433–7434 (1991a).

Van Duyne, G. D., Standaert, R. F., Karplus, A., Schreiber, S. L. & Clardy, J. J. Mol. Biol. 229, 105–124 (1993).

Vezina, C., Kudelski, A. & Sehgal, S. N. J. Antibiot. 28, 721–726 (1975). Zakian, V. A. Cell 82, 685–687 (1995)

---

What is claimed is:

1. A method for assessing interactions with a three dimensional representation of a molecular model including a FRB domain comprising providing a computer system for producing a three-dimensional representation of a molecule or molecular complex, wherein said computer system comprises:

a machine-readable data storage medium comprising a data storage material encoded with machine-readable data, wherein said data comprises the structure coordinates of an FRB domain;

a working memory for storing instruction for processing said machine-readable data;

a central-processing unit coupled to said working memory and to said machine-readable data storage medium for processing said machine-readable data into said three-dimensional representation; and a display coupled to said central-processing unit for displaying said three-dimensional representation; and
wherein said method further comprises executing instructions on a computer for (a) generating a three dimensional representation of a protein including an FRB domain from structural coordinates of said protein, such that the computer loads into memory thereof computer-readable data comprising structural coordinates of a molecule of molecular complex comprising an FRB domain molecular model;

(b) generating molecular models of one or more test compounds;

(c) calculating, from said molecular models, one or more possible molecular complexes which could be formed by association of said protein with said one or more test compound; and (d) generating output data indicative of the degree of interaction and/or the location and/or the orientation of such interaction, if any.

2. The computer system of claim 3 in which the coordinates for the FRB domain are set forth in FIG. 4, or coordinates having a root mean square deviation therefrom, with respect to conserved protein backbone atoms, of not more than 1.5 Å.

3. A method for assessing interactions with a three dimensional representation of a molecular model including a FRB domain comprising providing a computer system for determining at least a portion of the structure coordinates corresponding to an X-ray diffraction pattern of a molecule or molecular complex, wherein said computer comprises:

a machine-readable data storage medium comprising a data storage material encoded with machine-readable data, wherein said data comprises at least a portion of the structure coordinates of the FRB domain set forth in FIG. 4 or coordinates having a root mean square deviation therefrom, with respect to conserved protein backbone atoms, of not more than 1.5 Å;

a machine-readable data storage medium comprising a data storage material encoded with machine-readable data, wherein said data comprises an X-ray diffraction pattern of said molecule or molecular complex;

a working memory for storing instructions for processing said machine-readable data of (a) and (b);

a central-processing unit coupled to said working memory and to said machine-readable storage medium of (a) and (b) for performing a Fourier transform of the machine-readable data of (a) and for processing said machine-readable data of (b) into structure coordinates based on the Fourier transform of the machine-readable data; and a display coupled to said central-processing unit for displaying said structure coordinates of said molecule or molecular complex; and
wherein said method further comprises executing instructions on a computer for (a) generating a three dimensional representation of a protein including an FRB domain from structural coordinates of said protein, such that the computer loads into memory thereof computer-readable data comprising structural coordinates of a molecule of molecular complex comprising an FRB domain molecular model;

(b) generating molecular models of one or more test compounds;

(c) calculating, from said molecular models, one or more possible molecular complexes which could be formed by association of said protein with said one or more test compound; and (d) generating output data indicative of the degree of interaction and/or the location and/or the orientation of such interaction, if any.

4. A method for displaying a graphical three-dimensional representation of a molecular complex including an FRB domain and at least one other compound, which method comprises executing instructions on a computer for (a) generating a three-dimensional representation of a protein including an FRB domain from structural coordinates of said protein, such that the computer loads into memory thereof computer-readable data comprising structural coordinates of a molecule or molecular complex comprising an FRB domain, (b) generating molecular models of one or more test compounds, (c) calculating, from said molecular models, one or more possible molecular complexes which could be formed by association of said protein with said one or more test compound, and (d) displaying a graphical three-dimensional representation of the molecular complex including the FRB domain.

5. A method of claim 4, wherein said test compound is a rapamycin mimetic in which one or more structural segments of rapamycin is replaced.

6. A method of claim 4, wherein the three-dimensional representation of said FRB domain is based on coordinates of FIG. 4, or based on coordinates having a root mean square deviation therefrom with respect to conserved protein backbone atoms of not more than 1.5 Å.

7. A method for assessing interactions with a three dimensional representation of a molecular model of a polypeptide including an FRB domain comprising:

(a) generating a (i) molecular model of an FRB domain from structural coordinates set forth in FIG. 4, or coordinates having a root mean square deviation therefrom, with respect to conserved protein backbone atoms, of not more than 1.5 Å, and (ii) a molecular model of a test compound;

(b) calculating the ability of the FRB molecular model to associate with the test compound molecular model; and (c) generating output data indicative of the degree of interaction and/or the location and/or the orientation of such interaction, if any.

8. The method of any of claims 1, 3, 4 or 7, wherein the test compound is a protein.

9. The method of any of claims 1, 3, 4 or 7, wherein the test compound is a peptide.

10. The method of any of claims 1, 3, 4 or 7, wherein the test compound is a small organic molecule.

11. The method of any of claims 1, 3 or 7, wherein the test compound is a rapamycin mimetic in which one or more structural segments of rapamycin is replaced.

12. The method of any of claims 1, 3, 4 or 7, wherein the step of calculating the ability of the FRB molecular model to associate with the test compound molecular model synchronizes geometric and steric requirements for a molecular complex thereof.

13. The method of any of claims 1, 3, 4 or 7, wherein the step of calculating the ability of the FRB molecular model to associate with the test compound molecular model utilizes dynamic simulation of molecular complex thereof.

14. The method of any of claims 1, 3, 4 or 7, wherein the step of calculating the ability of the FRB molecular model to associate with the test compound molecular model calculates energy minimization of molecular complex thereof.

15. The method of any of claims 1, 3, 4 or 7, used for de novo molecular design of a ligand for an FRB domain.

16. The method of any of claims 1, 3, 4 or 7, used for optimization of a lead molecule for use as a ligand for an FRB domain.

17. The method of any of claims 1, 3, 4 or 7, used for selection of candidate drug structures based on structural criteria.

18. The method of any of claims 1, 3, 4 or 7, used for selection of candidate drug structures.

* * * * *

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 107 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO:1:

```
Gly Val Gln Val Glu Thr Ile Ser Pro Gly Asp Gly Arg Thr Phe Pro
1               5                   10                  15

Lys Arg Gly Gln Thr Cys Val Val His Tyr Thr Gly Met Leu Glu Asp
            20                  25                  30

Gly Lys Lys Phe Asp Ser Ser Arg Asp Arg Asn Lys Pro Phe Lys Phe
        35                  40                  45

Met Leu Gly Lys Gln Glu Val Ile Arg Gly Trp Glu Glu Gly Val Ala
    50                  55                  60

Gln Met Ser Val Gly Gln Arg Ala Lys Leu Thr Ile Ser Pro Asp Tyr
65                  70                  75                  80

Ala Tyr Gly Ala Thr Gly His Pro Gly Ile Ile Pro Pro His Ala Thr
                85                  90                  95

Leu Val Phe Asp Val Glu Leu Leu Lys Leu Glu
                100                 105
```

-continued (2) INFORMATION FOR SEQ ID NO:2:

(i) SEQUENCE CHARACTERISTICS:
        (A) LENGTH: 100 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

```
Glu Leu Ile Arg Val Ala Ile Leu Trp His Glu Met Trp His Glu Gly
1               5                   10                  15

Leu Glu Glu Ala Ser Arg Leu Tyr Phe Gly Glu Arg Asn Val Lys Gly
            20                  25                  30

Met Phe Glu Val Leu Glu Pro Leu His Ala Met Met Glu Arg Gly Pro
        35                  40                  45

Gln Thr Leu Lys Glu Thr Ser Phe Asn Gln Ala Tyr Gly Arg Asp Leu
    50                  55                  60

Met Glu Ala Gln Glu Trp Cys Arg Lys Tyr Met Lys Ser Gly Asn Val
65                  70                  75                  80

Lys Asp Leu Thr Gln Ala Trp Asp Leu Tyr Tyr His Val Phe Arg Arg
                85                  90                  95

Ile Ser Lys Gln
            100
```